(12) United States Patent
Dekel et al.

(10) Patent No.: US 7,376,279 B2
(45) Date of Patent: May 20, 2008

(54) THREE-DIMENSIONAL IMAGE STREAMING SYSTEM AND METHOD FOR MEDICAL IMAGES

(75) Inventors: Shai Dekel, Or-Yehuda (IL); Nitzan Goldberg, Jerusalem (IL); Alexander Sherman, Biet-Shemesh (IL)

(73) Assignee: IDX Investment Corporation, Burlington, VT (US)

( * ) Notice: Subject to any disclaimer, the term of this patent is extended or adjusted under 35 U.S.C. 154(b) by 912 days.

(21) Appl. No.: 10/022,122

(22) Filed: Dec. 14, 2001

(65) Prior Publication Data

US 2003/0005140 A1    Jan. 2, 2003

Related U.S. Application Data

(60) Provisional application No. 60/256,318, filed on Dec. 14, 2000.

(51) Int. Cl.
*G06K 9/36* (2006.01)
(52) U.S. Cl. .................. 382/240; 382/232; 382/302
(58) Field of Classification Search ........ 382/232–233, 382/240, 244–248, 260–263, 264; 348/399; 703/247
See application file for complete search history.

(56) References Cited

U.S. PATENT DOCUMENTS

| | | | |
|---|---|---|---|
| 3,580,655 A | 5/1971 | Leith et al. | 359/28 |
| 3,950,103 A | 4/1976 | Schmidt-Weinmar | 356/450 |
| 4,136,954 A | 1/1979 | Jamieson | 356/456 |
| 4,155,097 A | 5/1979 | Lux | 375/240.24 |
| 4,190,861 A | 2/1980 | Lux | 375/240.24 |
| 4,223,354 A | 9/1980 | Noble et al. | 348/774 |
| 4,393,456 A | 7/1983 | Marshall, Jr. | 708/316 |
| 4,569,075 A | 2/1986 | Nussbaumer | 704/203 |
| 4,599,567 A | 7/1986 | Goupillaud et al. | 324/76.33 |
| 4,652,881 A | 3/1987 | Lewis | 342/160 |
| 4,663,660 A | 5/1987 | Fedele et al. | 375/240.1 |
| 4,674,125 A | 6/1987 | Carlson et al. | 382/303 |
| 4,701,006 A | 10/1987 | Perlmutter | 359/9 |
| 4,760,563 A | 7/1988 | Beylkin | 367/73 |

(Continued)

FOREIGN PATENT DOCUMENTS

EP    0510933    10/1992

(Continued)

OTHER PUBLICATIONS

Merz et al. Iterative Transmission of Media Streams. *ACM* international conference on multimedia pp. 283-290 (1997).

(Continued)

*Primary Examiner*—Duy M Dang
(74) *Attorney, Agent, or Firm*—Zaretsky Patent Group PC; Howard Zaretsky

(57) ABSTRACT

In a system for transmitting a three-dimensional (3-D) digital image over a communication network, in response to a client computer generating a request for interaction with a 3-D image stored on an image storage device, a server computer performs two-dimensional sub-band transform decompositions in x-axis and y-axis directions upon the 3-D image, performs a one-dimensional sub-band transform decomposition in a z-axis direction upon a portion of the two-dimensionally transform-decomposed digital image, and progressively transmits to the client computer data representing a region of interest specified in the client request.

30 Claims, 33 Drawing Sheets

U.S. PATENT DOCUMENTS

| | | | |
|---|---|---|---|
| 4,785,348 A | 11/1988 | Fonsalas et al. | 375/240.21 |
| 4,785,349 A | 11/1988 | Keith et al. | 375/240.23 |
| 4,799,179 A | 1/1989 | Masson et al. | 708/312 |
| 4,805,129 A | 2/1989 | David | 708/300 |
| 4,815,023 A | 3/1989 | Arbeiter | 708/301 |
| 4,817,182 A | 3/1989 | Adelson et al. | 382/248 |
| 4,821,223 A | 4/1989 | David | 708/308 |
| 4,827,336 A | 5/1989 | Acampora et al. | 375/240.01 |
| 4,829,378 A | 5/1989 | LeGall | 375/240.11 |
| 4,837,517 A | 6/1989 | Barber | 324/339 |
| 4,839,889 A | 6/1989 | Gockler | 370/210 |
| 4,864,398 A | 9/1989 | Avis et al. | 348/443 |
| 4,868,868 A | 9/1989 | Yazu et al. | 704/205 |
| 4,894,713 A | 1/1990 | Delonge et al. | 375/240.2 |
| 4,897,717 A | 1/1990 | Hamilton et al. | 375/240.17 |
| 4,904,073 A | 2/1990 | Lawton et al. | 389/851 |
| 4,922,544 A | 5/1990 | Stansfield et al. | 382/166 |
| 4,929,223 A | 5/1990 | Walsh | 493/56 |
| 4,936,665 A | 6/1990 | Whitney | 359/565 |
| 4,974,187 A | 11/1990 | Lawton | 708/420 |
| 4,982,283 A | 1/1991 | Acampora | 375/240.12 |
| 4,985,927 A | 1/1991 | Norwood et al. | 382/149 |
| 4,987,480 A | 1/1991 | Lippman et al. | 348/396.1 |
| 4,999,705 A | 3/1991 | Puri | 348/412.1 |
| 5,000,183 A | 3/1991 | Bonnefous | 600/437 |
| 5,001,764 A | 3/1991 | Wood et al. | 382/145 |
| 5,014,134 A | 5/1991 | Lawton et al. | 382/240 |
| 5,018,210 A | 5/1991 | Merryman et al. | 382/145 |
| 5,049,992 A | 9/1991 | Citta et al. | 348/443 |
| 5,049,993 A | 9/1991 | LeGall et al. | 348/448 |
| 5,068,911 A | 11/1991 | Resnikoff et al. | 382/240 |
| 5,072,308 A | 12/1991 | Lin et al. | 358/426.02 |
| 5,073,964 A | 12/1991 | Resnikoff | 382/277 |
| 5,081,645 A | 1/1992 | Resnikoff et al. | 375/146 |
| 5,095,447 A | 3/1992 | Manns et al. | 382/144 |
| 5,097,331 A | 3/1992 | Chen et al. | 375/240.11 |
| 5,101,280 A | 3/1992 | Moronaga et al. | 382/239 |
| 5,101,446 A | 3/1992 | Resnikoff et al. | 382/246 |
| 5,103,306 A | 4/1992 | Weiman et al. | 348/400.1 |
| 5,109,451 A | 4/1992 | Aono et al. | 382/166 |
| 5,121,191 A | 6/1992 | Cassereau et al. | 348/443 |
| 5,124,930 A | 6/1992 | Nicolas et al. | 702/76 |
| 5,128,757 A | 7/1992 | Citta et al. | 375/240.01 |
| 5,128,791 A | 7/1992 | LeGall et al. | 348/369 |
| 5,148,498 A | 9/1992 | Resnikoff et al. | 382/248 |
| 5,152,953 A | 10/1992 | Ackerman | 266/252 |
| 5,156,943 A | 10/1992 | Whitney | 430/321 |
| 5,173,880 A | 12/1992 | Duren et al. | 367/73 |
| 5,182,645 A | 1/1993 | Breeuwer et al. | 348/458 |
| 5,235,434 A | 8/1993 | Wober | 358/448 |
| 5,241,395 A | 8/1993 | Chen | 328/426.4 |
| 5,262,958 A | 11/1993 | Chui et al. | 702/75 |
| 5,335,016 A | 8/1994 | Nakagawa | 375/240.03 |
| 5,347,479 A | 9/1994 | Miyazaki | 708/400 |
| 5,381,145 A | 1/1995 | Allen et al. | 341/107 |
| 5,412,741 A | 5/1995 | Shapiro | 382/232 |
| 5,420,891 A | 5/1995 | Akansu | 375/350 |
| 5,453,945 A | 9/1995 | Tucker et al. | 708/400 |
| 5,495,292 A | 2/1996 | Zhang et al. | 375/240.02 |
| 5,497,435 A | 3/1996 | Berger | 382/249 |
| 5,534,925 A | 7/1996 | Zhong | 348/384.1 |
| 5,537,493 A | 7/1996 | Wilkinson | 382/240 |
| 5,546,477 A | 8/1996 | Knowles et al. | 382/242 |
| 5,563,690 A | 10/1996 | Hasegawa et al. | 399/286 |
| 5,602,589 A | 2/1997 | Vishwanath et al. | 375/240.11 |
| 5,606,359 A | 2/1997 | Youden et al. | 725/88 |
| 5,699,458 A | 12/1997 | Sprague | 382/250 |
| 5,710,835 A | 1/1998 | Bradley | 382/233 |
| 5,832,300 A | 11/1998 | Lowthert | 710/33 |
| 5,838,377 A | 11/1998 | Greene | 375/240.11 |
| 5,850,226 A | 12/1998 | Nagasawa et al. | 345/428 |
| 5,861,920 A | 1/1999 | Mead et al. | 375/240.25 |
| 5,872,965 A | 2/1999 | Petrick | 712/236 |
| 5,886,733 A | 3/1999 | Zdepski et al. | 725/64 |
| 5,982,362 A | 11/1999 | Crater et al. | 715/719 |
| 6,009,435 A | 12/1999 | Taubin et al. | 707/101 |
| 6,038,257 A | 3/2000 | Brusewitz et al. | 375/240.21 |
| 6,049,342 A | 4/2000 | Nielsen et al. | 345/473 |
| 6,049,821 A | 4/2000 | Theriault et al. | 709/203 |
| 6,088,035 A | 7/2000 | Sudarsky et al. | 345/421 |
| 6,314,452 B1 * | 11/2001 | Dekel et al. | 709/203 |
| 6,711,297 B1 * | 3/2004 | Chang et al. | 382/240 |

FOREIGN PATENT DOCUMENTS

| | | |
|---|---|---|
| EP | 0593013 | 4/1994 |
| EP | 0611051 | 8/1994 |
| EP | 0622741 | 11/1994 |
| EP | 0701375 | 3/1996 |
| GB | 2211691 | 7/1991 |
| GB | 2284121 | 5/1995 |
| GB | 2285374 | 6/1995 |
| WO | WO 88/10049 | 12/1988 |
| WO | WO 91/03902 | 3/1991 |
| WO | WO 91/18361 | 11/1991 |
| WO | WO 94/23385 | 10/1994 |
| WO | WO 95/19683 | 7/1995 |
| WO | WO 96/09718 | 3/1996 |

OTHER PUBLICATIONS

Salous et al. Managing Bandwidth Utilisation for Image Transmission, *IEEE* International Conference on Systems, man, and Cybernetics 5:4636-4641 (1998).

To et al. A Method for Progressive and Selective Transmission of Multi-Resolution Models. *ACM* symposium on virtual reality software and technology. pp. 88-95 (1998).

Advertising brochure entitled "Portable Image Format," for Mr. Sid by Lizardteck Inc., copyright 1999.

Article entitled "Wavelet Transforms that Map Integers to Integers" by Calderbank et al., published in *J. Fourier Anal. Appl.* (1998).

Article entitled "RSNA Vendor Showcase Wealth of Web-based Teleradiology" by Michael J. Cannavo, published in *Telehealth Magazine*, 57-59 (1999).

Article entitled "Is It Safe" by Michael J. Cannavo, published in *Imaging Economics* (1999).

Article entitled "Factoring Wavelet Transforms into Lifting Steps" by Daubechies et al., published in *J. Fourier Anal. Appl.*, 4(3):247-269 (1998).

Article entitled "Nonlinear Approximation" by R. A. Devore, published in *Acta Numerica*, 51-150 (1998).

Article entitled "Compression Related Properties of Color Spaces" by A. Drukarev, published in *Proc. SPIE*, 3024:855-863 (1997).

Article entitled "Revolutionary Protocol Speeds Electronic Image Delivery" by John C. Hayes, published in *Telehealth Magazine* (1999).

Article entitled "Understanding Image Transform Codes" by Mallat et al., published in *Proc. SPIE Aerospace Conf.* (1997).

Article entitled "Arithmetic Coding Revisited" by Moffat et al., published in *Proc. DDC* (Snowbird, Utah), 202-211 (1995).

Article entitled "Color Space Selection for JPEG Image Compression" by Moroney et al., published in *J. Elec. Imaging*, 4(4):373-381 (1995).

Article entitled "Handling High-Performance Web Images for E-Commerce: Live Picture Meets Oracle" by Lee J. Nelson, published in *Advanced Imaging*, 68-70 (1999).

Article entitled "Image Compression Technology: For the Decade Ahead, Wavelet Soars!" by Lee J. Nelson, published in *Advanced Imaging*.

Article entitled "An Image Multiresolution Representation for Lossless and Lossy Compression" by Said et al., published in *IEEE. Trans. Image Proc.*, 5(9):1303-1310 (1996).

Article entitled "A New, Fast and Efficient Image Code Based on Set Partitioning in Hierarchical Trees" by Said et al., published in *IEEE Trans. Circuits and Sysytems for Video Tech.*, 6(3):243-250 (1996).

Article entitled "Embedded Image Coding Using Zerotrees of Wavelet Coefficients" by J. M. Shapiro, published in *IEEE Trans. Sig. Proc.*, 41(12):3445-3462 (1993).

Article entitled "Lossy to Lossless Image Compression Using Reversible Integer Wavelet Transform" by Sheng et al., published in *Proc. IEEE International Conf. On Image Processing* (SAIC) 876-880(1998).

Article entitled "High Performance Scalable Image Compression with EBCOT" by D. Taubman, submitted to *IEEE Transactions on Image Processing*, 344-348 (1999).

Article entitled "Overcoming Bandwidth Limitations:Professional Image Sharing" by Paul Worthington, published in *The Future Image Report*, 5(10),(1998).

Article entitled "A DCT-Based Embedded Image Coder" by Xiong et al., published in *IEEE Signal Proc. Letters,* 3(11): (1996).

Article entitled "CREW: Compression with reversible embedded wavelets" by Zandi et al., published in *Proc. Of Data Compression Conference,* 212-221 (1995).

* cited by examiner

| $\sqrt{2}$ | | | $\sqrt{2}$ |
|---|---|---|---|
| $\sqrt{2}$ | | | $\sqrt{2}$ |
| ⋮ | | | ⋮ |
| ⋮ | 1 | $\sqrt{2}$ | 1 | $\sqrt{2}$ | z

FIG. 7

```
zeroModel_16.start_model();
zeroModel_4.start_model();
zeroCoefModel.start_model();
coefSignModel.start-model();

while(encoder.getNextGroupOf16()) {
   bool isZero;

if (encoder.isGroupType16()) {
      isZero = encoder.isZeroGroupOf16();
      arithmetic_encode_symbol(ZeroModel_16,isZero);
      if (isZero)
            continue;
   } while (encoder.getNextGroupof4()) {
      if (encoder.isGroupType4()) {
         if (!encoder.mustbeNoZeroGroup()) {
            isZero = encoder.isZeroGroupOf4();
            arithmetic_encode_symbol(ZeroModel_4,isZero);
            if (isZero)
                  continue;
         }
      } while (encoder.getNext_Type1_Coef(isZero)) {
         if (!encoder.mustbeNoZeroCoef())
            arithmetic_encode_symbol(zeroCoefModel,isZero);
         if (!isZero)
            arithmetic_encode_symbol(coefSignModel,encoder.getCoefSign));
      }
   } if (!(encoder.isLastBitPlane() && equalBinSetting)) {
      bitModel.start_model();

int bit;
```

FIG. 11

```
bitModel.startModel();
zeroCoefModel.startModel();
coefSignModel.startModel();
while (encoder.moreCoef()) {        ～1210
    if (encoder.isCoefReported()) {   ～1220
        arithmetic_encode_symbol(
            bitModel,encoder.reportedCoefPrecisionBit());
    } else {
        if ( encoder.isCoefExactZero() ) ～1230
            arithmetic_encode_symbol(zeroCoefModel,true);
        else {
            arithmetic_encode_symbol(zeroCoefModel,false);
            arithmetic_encode_symbol(
                coefSignModel,encoder.getCoefSign());
        }
    }
```

FIG. 12A

```
bitModel.startModel();

for (int z = 0 ; z != HalfBitPlaneZSize;z++) {
    for (int y = 0 ; y != HalfBitPlaneYSize;y++) {
        for (int x = 0 ; x != HalfBitPlaneXSize;x++) {
            arithmetic_encode_symbol(bitModel,coefHalfBit[x][y][z]);
        }
    }
}
```

FIG. 12B

```
zeroModel_16.start_model();
zeroModel_4.start_model();
zeroCoefModel.start_model();
coefSignModel.start_model();

while(decoder.getNextGroupOf16()) {
    if (decoder.isGroupType16()) {
        if (arithmetic_decode_symbol(zeroModel_16)) {
            decoder.zeroGroupOf16();
            continue;
        }
        else
            decoder.removeZeroGroupOf16();
    } while (decoder.getNextGroupOf4()) {
        if (decoder.isGroupType4()) {
            if (!decoder.mustbeNotZeroGroup()) {
                if (arithmetic_decode_symbol(zeroModel_4)) {
                    decoder.zeroGroupOf4();
                    continue;
                }
            }
            decoder.removeZeroGroupOf4();
        } while (decoder.getNext_Type1_Coef()) {
           if (decoder.mustbeNotZeroCoef())

decoder.setNextSigCoef(arithmetic_decode_symbol(coefSignmodel));
            else if (!arithmetic_decode_symbol(zeroCoefModel))

decoder.setNextSigCoef(arithmetic_decode_symbol(coefSignmodel));
        }
    }
} if (! (decoder.isLastBitPlane() && equalBinSetting)) {
   bitModel.start_model();
   while(decoder.moreSignificantCoef())
       decoder.setSignificantCoefBit(arithmetic_decode_symbol(bitModel));
}
```

FIG. 15

```
bitModel .startModel();
zeroCoefModel.startmodel();
coefSignModel.startmodel();

decoder.initializeLSBPlaneCoefScan();
                                          ~1610
while (decoder.moreCoef()) {
    if (decoder.isCoefReported()) {
        if(decoder.isSkippedCoef()) {
            decoder. updateLSB (0);
        }
        else { decoder.updateLSB(arithmetic_decoder_symbol(bitModel));
        }
    }
    else {
        if(!decoder.isSkippedCoef()) {
            if (!arithmetic_decoder_symbol(zeroCoefModel))

decoder.setLSB(arithmetic_decoder_symbol(coefSignModel));
        }
```

FIG. 16A

```
bitModel.startModel();

for (int z = 0 ; z != HalfBitPlaneZSize;z++) {
    for (int y = 0 ; y != HalfBitPlaneYSize;y++) {
        for (int x = 0 ; x != HalfBitPlaneXSize;x++) {
            coefHalfBit[x][y][z] = arithmetic_decoder_symbol(bitModel);
        }
    }
}
```

FIG. 16B

```
for (int res = 1 ; res <= dyadicResolution(ROI); res++) { for( int z=0;
         z < NumberOfZtilesOnDyadicResolution (res,ROI);
         z++ ) {

GetCoefficientsofLowerResolution(res, Ztile);

for( int x=0;
             x < NumberOfXtilesOnDyadicResolution(res,ROI);
             x++ ) {
            for( int y=0;
                 y <
                 NumberOfYtilesOnDyadicResolution(res,ROI);
                 y++ ) {
                 DecodeOrExtractFromCacheSubbandCoefficients
                 ( res, x, y, z );
            }
        }

ExecuteInverseSubbandTransform(z);

if( res == dyadicResolution(ROI))
            ImageResizeAndMappingTo8bitScreen();
    }
}
```

FIG. 20

```
for(int t_Resolution=numberOfResolutions-jumpSize; t_Resolution>=1 :
t_Resolution--) {
      leftTilesZInMemoryBuffer(t_Resolution)=
                  NumberOfTilesZInFrameMemoryBuffer(t_Resolution);
      currentTile(t_Resolution)=0;
} for(t_Resolution=numberOfResolutions-jumpSize; ;) {
      // calculate the Z and it's resolution
      if (currentTile(t_Resolution)< nTileZ(t_Resolution)) {
          for (int t_y = 0 ; t_y < nTileY(t_Resolution); t_y++)
              for (int t_x = 0 ; t_x < nTileX(t_Resolution); t_x++)
                  preprocessSubbandTile(t_x,t_y,
currentTile(t_Resolution), t_Resolution);
      }

// update the indeces
      leftTilesZInMemoryBuffer(t_Resolution)--;
      currentTile(t_Resolution)++;

if(currentTile(t_Resolution) < nTileZ(t_Resolution)) {
            // switch the resolution
            if(leftTilesZInMemoryBuffer(t_Resolution)==0) {
                  leftTilesZInMemoryBuffer(t_Resolution) =
                        NumberOfTilesZInFrameMemoryBuffer(t_Resolution
                  );
                  t_Resolution --;
            }
            else
                  t_Resolution = numberOfResolutions-jumpSize;
      }
      else }
            t_Resolution --;
```

FIG. 24

THREE-DIMENSIONAL IMAGE STREAMING SYSTEM AND METHOD FOR MEDICAL IMAGES

CROSS-REFERENCED TO RELATED APPLICATION

The benefit of U.S. provisional patent application Ser. No. 60/256,318, filed Dec. 14, 2000, entitled "Three-Dimensional Image Streaming System and Method," is hereby claimed under 35 U.S.C. § 119, and the specification thereof is incorporated herein in its entirety by this reference.

BACKGROUND OF THE INVENTION

1. Field of the Invention

The invention relates generally to the field of medical imaging and, more specifically, to transmission of medical imagery via a relatively narrow bandwidth client-server computer network such as the World Wide Web.

2. Description of the Related Art

The most common medical imaging techniques produce three-dimensional (3-D) data sets. Medical imaging techniques, such as computed tomography (CT), magnetic resonance (MR), positron emission tomography (PET), and single-photon emission computed tomography (SPECT), generate multiple slices in a single examination. Each such slice represents a different cross-section of the body part that is imaged. A simple transfer to the client computer of the result of the examination stored in the server's storage is obviously time consuming in a narrow bandwidth environment. This problem can be overcome by storing images in some compressed formats.

Data compression techniques can be roughly divided into two classes: lossy and lossless. Lossless compression techniques allow exact reconstruction of the original image, while lossy compression techniques achieve higher compression ratios, because they allow some acceptable degradation.

Although lossy compression is acceptable in many cases, lossless transmission is required in medical applications because lossy compression of images can lead to errors in diagnosis by introducing artifacts. Furthermore, there exist several legal and regulatory issues that favor lossless compression in medical applications. Although precise diagnosis require lossless representation of the study, lossy compression can be extremely useful for medical applications in which quick image browsing is desired. Therefore, the combination of lossy and lossless representations in a single workflow is desirable, with progressive lossy streaming of 3-D data terminating at lossless quality.

Because 3-D image data can be represented as a set of two-dimensional (2-D) images, it is possible to code these 2-D images independently. There exist several 2-D lossless compression algorithms, such as the LOw COmplexity LOssless COmpression of Images (LOCO-I) on which a lossless image compression standard called JPEG-LS is base, the Context-based Adaptive Lossless Image Codec (CALIC) algorithm and Compression with Reversible Embedded Wavelets (CREW). However, such 2-D methods do not utilize the inter-slice dependencies that exist among pixel values in the third dimension. A better approach considers the whole set of slices as a single 3-D data set taking advantage of correlation in all three dimensions.

Several methods that utilize dependencies in all three dimensions have been proposed for compression of 3-D data, both lossy and lossless, such as the Improved 3-D EZW (3D-IEZW); Modified EZW algorithm, used for compression of volumetric medical images; Context-based coding improvement of the EZW algorithm (3-D CB-EZW); a 3-D extension of Set Partitioning in Hierarchical Trees and Scalable Compressed Video coding algorithms. However, there is a common disadvantage of all the existing methods: they all need to store a compressed version of the original data, because the compression is very time consuming. These methods additionally lead to a tremendous growth of system memory usage. Wavelet compression is well known in the art. Conventional compression systems preferred wavelet bases of best coding performance.

A system and method for transmitting a digital image over a communication network is disclosed in U.S. patent application Ser. No. 6,314,452, "System and Method for Transmitting a Digital Image Over a Communication Network", incorporated herein in its entirety by this reference That system and method does not address problems involved with lossless compression, and it does not specifically address 3-D images.

A system and method for a lossless wavelet transform in 2-D, having only the X and Y directions, is disclosed in U.S. patent application Ser. No. 60/198,017 "Lossless Progressive Streaming of Images Over the Internet" incorporated herein in its entirety by this reference. That system and method does not address 3-D images.

SUMMARY OF THE INVENTION

The present invention relates to a 3-D image data streaming system that obviates storing a compressed version of the original data by streaming region-of-interest (ROI) data using the original stored 3-D data. The system also avoids the computationally intensive task of compression of the full data. The term "pixels-on-demand" may be used in this patent specification to describe the process of serving the requested ROI and progressively transmitting the ROI data in real-time, where the quality of the view improves towards lossless quality as the transfer process progresses.

The system allows lossless progressive streaming of 3-D images over the Internet of speed and quality unknown in the prior art. Once a user indicates intention to view an image, a server performs a fast preprocessing step, after which the server quickly responds to requests for viewing specific regions of interest. Each request for an ROI triggers an encoding algorithm, but such that does, not involve the full 3-D image. Since the size of the ROI is limited by the size and resolution of the viewing device and by number of frames that can be simultaneously viewed at the client and not by the size of the full 3-D image, only a partial progressive coding computation is performed for a local area of the original 3-D data. The same is true for the client computer that performs decoding and rendering only for an ROI and not the full 3-D image. The imaging system described herein preferably uses wavelet bases of best performance in streaming ROI data.

In one aspect of the present invention there is disclosed a system and method for transmitting a three-dimensional digital image over a communication network. A 3-D digital image is stored on an image storage device accessible via the network. A client computer coupled to the network can generate a request for interaction with the 3-D image stored on the image storage device, the request identifying a region of interest within the image.

The system includes a server computer coupled to the communication network and the image storage device, wherein the server computer performs the steps of: i)

performing 2-D sub-band transform decompositions in x-axis and y-axis directions upon the three-dimensional digital image; ii) performing a 1-D sub-band transform decomposition in a z-axis direction upon a portion of the two-dimensionally transform-decomposed digital image; and iii) progressively transmitting to the client computer data representing the identified region of interest within the 3-D image.

In one or more embodiments of the present invention, the system can transmit to the client computer data representing thumbnail-resolution images resulting from the 2-D subband transform decompositions. Furthermore, the system can, in one or more embodiments of the invention, perform a one-dimensional sub-band transform decomposition in a z-axis direction comprising the steps of: a) computing transform coefficients using integer arithmetic and not floating-point arithmetic; and b) correcting the computed transform coefficients by performing integer arithmetic operations with one or more predetermined correction factors.

The steps of performing sub-band transform decompositions can comprise computing transform coefficients for each of a predetermined plurality of resolutions. Furthermore, the transform coefficients for an Nth resolution of the plurality can be computed in response to a one transform formula if N is odd and another transform formula if N is even. For example, the server computer can scale the transform coefficients by alternating factors of $\sqrt{2}$ and 1 along the z-axis, i.e., the resolution axis.

In yet another aspect of the present invention there is disclosed a system and method for transmitting a 3-D digital image over a communication network in which the request that a client computer generates for interaction with the 3-D image stored on the image storage device specifies a quality threshold and includes a request list specifying data blocks that define a region of interest within the 3-D image. The system includes a server computer coupled to the communication network and the image storage device, wherein the server computer, in response to the request list, transmits to the client computer a number of data blocks corresponding to the specified quality threshold.

In one or more embodiments of the present invention, the server computer can map the luminance of the three-dimensional image stored on the image storage device from a predetermined image bit depth to a predetermined screen bit depth in accordance with a monotonic luminance mapping function. The server computer can do so by, for example, computing a root mean square (RMS) increasing factor defined by a maximal derivative of the luminance mapping function. The server computer can provide more data blocks (i.e., more than some predetermined normal number) if the RMS increasing factor is greater than one and a fewer data blocks if the RMS increasing factor is less than one.

Furthermore, the request generated by the client computer can specify a resolution. In response, the server computer provides a number of data blocks corresponding to not only the specified quality threshold but also the specified resolution.

BRIEF DESCRIPTION OF THE DRAWINGS

FIG. 7 illustrates scaling factors of 3-D wavelet coefficients for different sub-bands.

FIG. 11 illustrates a server encoding algorithm bit plane significance scan pseudo-code.

FIG. 12A illustrates a least significant bit plane scan pseudo-code encoding algorithm.

FIG. 12B illustrates a half bit plane scan pseudo-code encoding algorithm.

FIG. 15 illustrates a client decoding algorithm bit plane scan pseudo-code.

FIG. 16A illustrates a least significant bit plane scan pseudo-code decoding algorithm.

FIG. 16B is a half bit plane scan pseudo-code decoding algorithm.

FIG. 20 is pseudo-code for multi-resolution march in the client rendering function.

FIG. 24 is pseudo-code for the memory constrained subband tile preprocessing function of the present invention.

DETAILED DESCRIPTION

1. Notation and Terminology

The following notation is used throughout this document.

| Term | Definition |
| --- | --- |
| 2D | Two dimensional |
| 3D | Three dimensional |
| 5D | Five dimensional |
| FIR | Finite Impulse Response |
| FWT | Forward Wavelet Transform |
| GUI | Graphical User Interface |
| ID | Identification tag |
| IWT | Inverse Wavelet Transform |
| ROI | Region Of Interest |
| URL | Uniform Resource Locator |
| LSB | Least Significant Bit |
| FP | Floating Point |
| EZW | Embedded coding of Zerotrees of Wavelet coefficients |

The following terminology and definitions apply throughout this document.

| Term | Definition |
| --- | --- |
| Rendering | Procedure to output/display a ROI of an image into a device such as a monitor, printer, etc. |
| Multiresolution | A pyramidal structure representing an image at dyadic resolutions, beginning with the original image as the highest resolution. |
| Subband Transform / subband coefficients | A method of decomposing an image (time domain) to frequency components (frequency domain). A representation of an image as a sum of differences between the dyadic resolutions of the image's multi-resolution. |
| Wavelet Transform / Wavelet coefficients | A special case of Subband Transform. |
| Quantization | A process that, given a number removes some precision from it, such that it will be possible to code it in lower precision using less bits of memory |
| Threshold | A process that, using a given positive constant, sets to zero any number whose absolute value is below the constant. |
| Progressive Transmission | Transmitting a given image in successive steps, where each step adds more detail to the rendering of the image |
| Progressive Rendering | A sequence of rendering operations, each adding more detail. |
| Progressive by accuracy | Transmit/render strong features first (sharp edges), less significant features (texture) last |
| Progressive by resolution | Transmit/render low resolution first, high resolution last |
| Distributed database | A database architecture that can be used in a network environment |
| Subband/Wavelet tile | A group of subband/wavelet coefficients corresponding to a time-frequency localization at some given spatial location and resolution/frequency |
| Subband/Wavelet data block | An encoded portion of a subband/wavelet tile that corresponds to some accuracy layer |

2. Description of Embodiments

Figure 1:
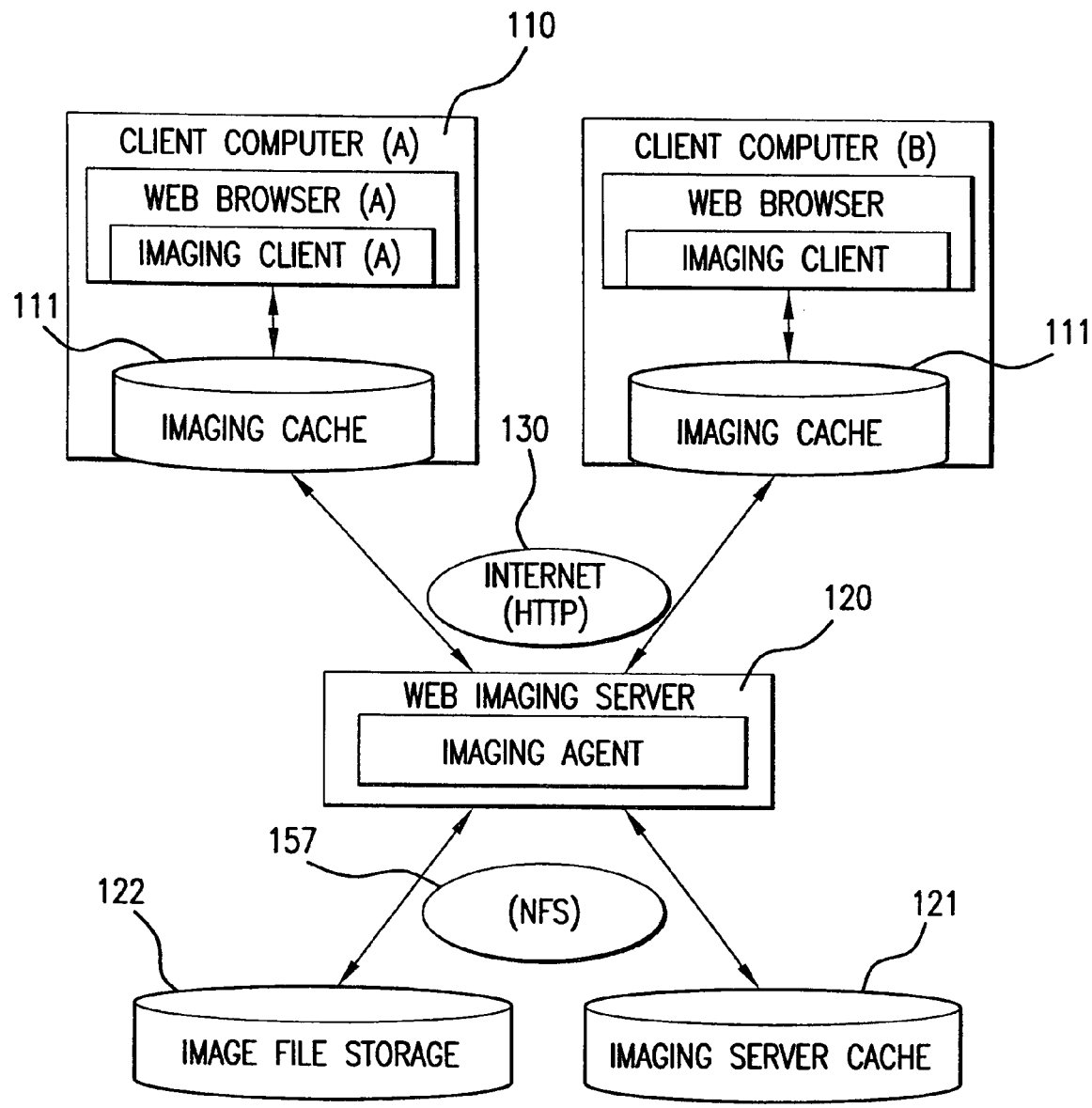
FIG. 1 is a block diagram of an embodiment of the system architecture.

Referring to FIG. 1, a block diagram is provided depicting the various components of the imaging system in one embodiment of the invention. A client computer 110 is coupled to a server computer 120 through a communication network 130.

In one embodiment, both client computer 110 and server computer 120 may comprise a PC-type computer operating with a Pentium®-class microprocessor, or equivalent. Each of the computers 110 and 120 may include a cache, 111 and 121 respectively, as part of its memory. The server computer 120 may include a suitable storage device 122, such as a high-capacity disk, CD-ROM, DVD, or the like. Server computer 120 is programmed with software that effects the processes described below. In view of the description below, persons skilled in the art to which the invention relates will be capable of writing or otherwise providing software suitable for such programming. In preparation for operation, the software can reside in whole or part on a hard disk or similar data medium (not shown) within server computer 120 and can be downloaded onto the disk or otherwise retrieved in whole or part from a remote source (not shown) via a communication network 130. Note that the present invention can be embodied not only as a system of computers but also as computer-implemented methods and as computer program products that carry the software via suitable computer data media.

The client computer 110 and server computer 120 may be connected to each other, and to other computers, through communication network 130, which may be the Internet, an intranet (e.g., a local area network), a wide-area network, or the like. Those having ordinary skill in the art will recognize that any of a variety of communication networks may be used to implement the present invention. Any suitable web browser-type application running on the client computer 110 can be used to connect to the server computer 120. The browser software can likewise be stored for execution on a hard disk or similar medium (not shown) within client computer 110 in the conventional manner.

Figure 2:
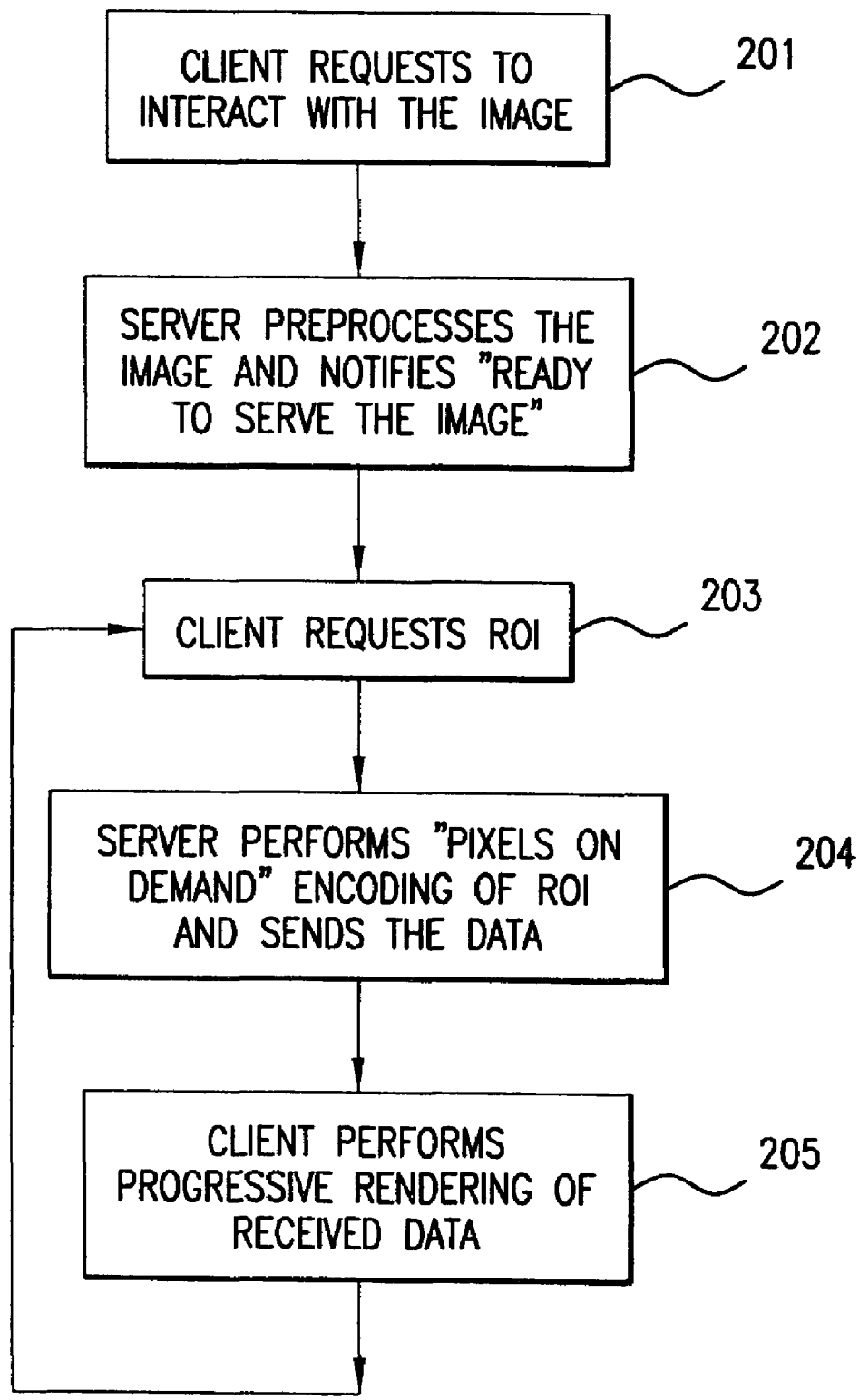
FIG. 2 illustrates an embodiment of the imaging system workflow.

The system workflow is first described with reference to FIG. 2. A client computer 110 (FIG. 1) begins by requesting to interact with a specific 3-D image at step 201. In response, the server computer 120 preprocesses the image at step 202, and notifies the client computer 110 that it is ready to serve the image. The client computer 110 continues by requesting a specific ROI at step 203. In response, the server computer 120 encodes this ROI and sends its encoded data at step 204. The client computer 110, in turn, performs progressive rendering of the received data at step 205, and may iterate back for another ROI at step 203.

The system workflow is now described with reference to FIG. 1. The user operating a client computer 110 selects, using common browser tools, a 3-D image residing on the image file storage 122. The corresponding URL request is received and processed by the server computer 120. In case results of previous computations on the 3-D image are not present in the imaging cache 121, the server computer 120 performs a fast preprocessing algorithm (described herein below as step 2201 with reference to FIG. 22). The result of this computation is inserted into the cache 121. Unlike previous, applications or methods, which perform full progressive encoding of the image offline, the goal of the preprocessing step is to allow the server computer 120, after a relatively fast computational step, to serve any ROI specified by the user of the client computer 110. For example, server software processing (step 202) of a sequence of 100 slices 512 by 512 pixels, 16-bit Grayscale each, typically takes 1-2 seconds, running on a computer with a Pentium.RTM. processor and the Windows NT.RTM. operating system.

Once the preprocessing stage is complete, the server computer 120 notifies the client computer 110 that the image is ready to be served. The server computer 120 also transmits the basic parameters associated with the image such as dimensions, number or resolutions, etc. Upon receiving this notification, the client computer 110 can select any ROI of the 3-D image, as indicated by the user through a GUI. The ROI is formulated (step 203) into a request list that is sent to the server computer 120. Each such request corresponds to a data block (as described herein below with reference to FIGS. 3 and 8).

The order of requests in the list corresponds to a progressive mode selected in the context of the application. For example, the order can be of increasing accuracy. Upon receiving the ROI request list, the server computer 120 processes the requests according to their order. For each request the server computer 120 checks if the corresponding data block exists in its cache 121. If not, the server computer 120 then computes the data block, stores it in the cache 121 and immediately sends it to the client computer 110. Once a data block that was requested arrives at the client computer 110, it is inserted into its cache 111. At various moments in time during the transfer process, a decision rule invokes a rendering of the ROI. If some of the data blocks required for a high quality rendering of the ROI were requested from the server computer 120 but have not arrived yet, the rendering of the ROI will be of lower quality. But, due to the progressive request order, the rendering quality will improve with each received data block as specified. The user can order a change of the ROI, in which case the rendering task at the client computer 110 is canceled. A new request list corresponding to a new ROI is then sent from the client computer 110 to the server computer 120 notifying the server to terminate the previous computation and transmission task and to begin the new one.

Figure 26:
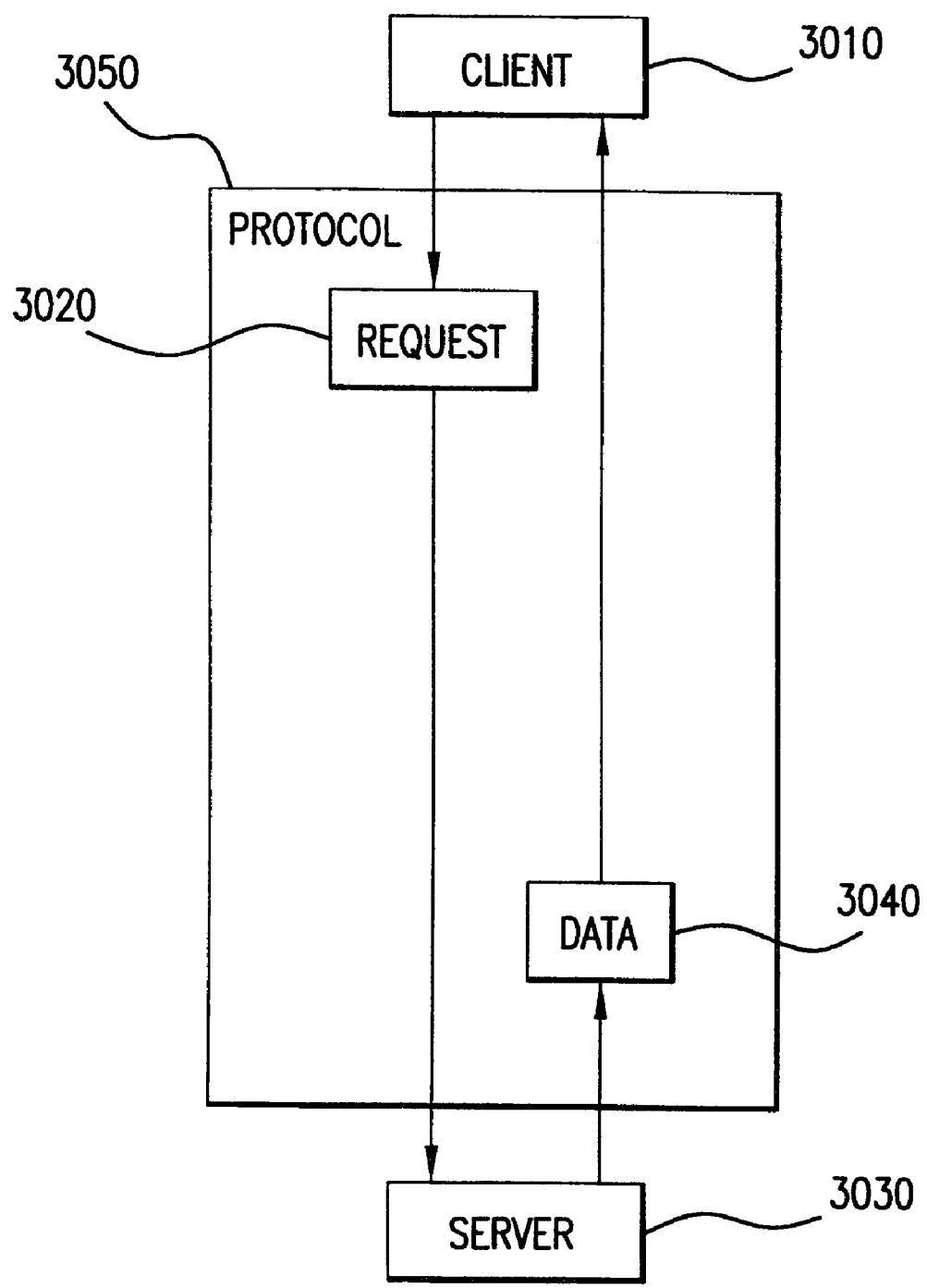
FIG. 26 is a diagram illustrating an imaging protocol of communication between client and server.

The imaging protocol serves as a common language between the server and its clients. It is described with reference to FIG. 26. The imaging protocol 3050 is mainly used by the client computer 3010 to efficiently stream to the server an ordered request 3020 list of data blocks required for progressive rendering of a given ROI, and by the server computer 3030 to efficiently compose and send to the client computer 3010 a stream of (requested) data blocks 3040.

Both client computer 3010 and server computer 3020 use the same distributed database associated with the protocol, such that they are using the same tagging system for the various data blocks. Using this approach it is also possible to cache the data blocks at both ends. The server computer 3020 is able to cache any computed data block, such that this data block can be sent to any other client that requests it. The client computer 3010 is able to cache any data block received, such that for any subsequent ROI rendering operation requiring the data block, it will be extracted from the client cache and not ordered from the server computer 3020. The protocol is designed such that the imaging system will have efficient ROI control and rendering in any mode such as: progressive by accuracy, progressive by resolution and progressive by spatial order.

Figure 29:
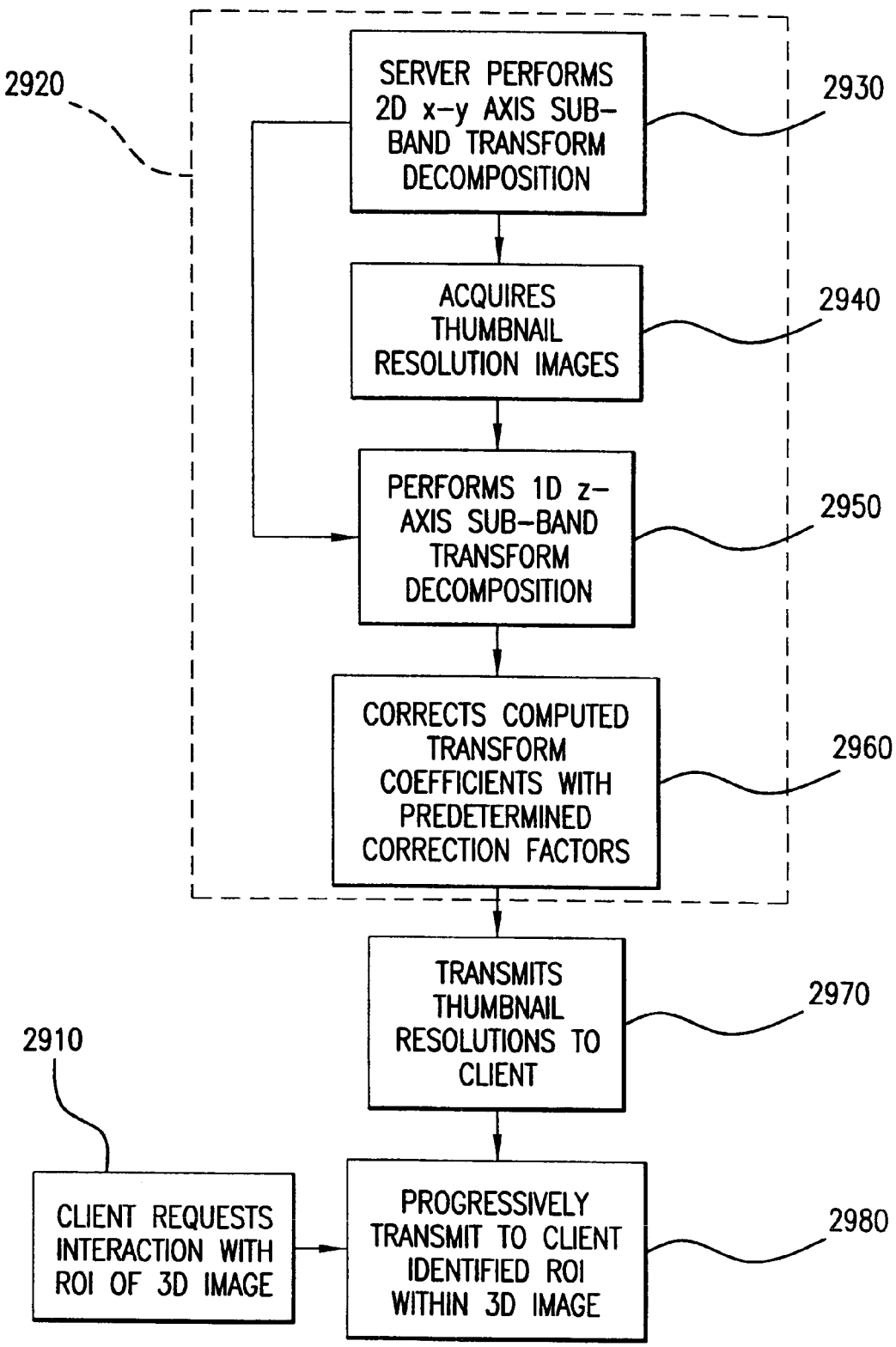
FIG. 29 is a flowchart illustrating a method for transmitting a 3D digital image in accordance with one aspect of the present invention.

The generalized method by which the present invention operates to transmit data blocks corresponding to the ROI in response to client requests is illustrated in FIG. 29. At step 2910, the client computer 110 (FIG. 1) generates a request for interaction with the 3-D digital image stored on the image storage device 122. As noted above, the request identifies an ROI within the image.

As a result of an initial request, a server computer process is initiated at step 2920. Note that a 3-D image can be conceptually described as a sequence along the z-axis direction of x-y frames, analogous to the manner in which a movie is described by a sequence of frames. The image is decomposed in the x-y plane and along the z-axis direction. The server computer 120 performs 2-D sub-band transform decompositions in x-axis and y-axis directions upon the 3-D image at step 2930. As described below in further detail, in two dimensions each frame is decomposed into four parts: {HH,HL,LH,LL}. This is repeated with each resolution step or level, where the LL part of resolution level N is the source image for resolution level N+1. Decomposition along the z-axis direction averages pairs of frames together, so with each resolution level the number of frames is reduced by half. For example, if there is a sequence of frames {1,2,3, 4,5,6 . . . }, at the first resolution level there will be {1+2,3+4,5+6, . . . }, where "1+2" represents the averaging of frames 1 and 2 together.

At step 2940, as described below in further detail, the server computer 120 acquires thumbnail-resolution images that were created as a result of the 2-D sub-band transform decompositions. As known in the art, thumbnail-resolution images or, simply, "thumbnails," are frames presented at a resolution less than or equal to that of the original image and at a quality less than or equal to that of the original image. In the present invention, thumbnails are presented as a sequence of the same number as in the original image {1,2,3,4,5,6}, so each thumbnail corresponds to a frame. Thumbnail resolution images are a by-product of the LL part. After decomposing the original image a few resolution levels, the LL part at that level is used as the thumbnail. Note that in embodiments of the invention in which thumbnails are not acquired, the process can proceed directly to step 2950.

At step 2950, as described below in further detail, 1-D sub-band transform decomposition in the z-axis direction is performed upon a portion, such as {HH,HL,LH}, of the two-dimensionally transform-decomposed digital image. The 1-D z-axis decomposition is not performed upon the LL portion in order to preserve its thumbnail qualities.

At step 2960, the computed transform coefficients are corrected by the performance of integer operations that utilize one or more predetermined correction factors. For reasons described below in further detail, the coefficients are ideally or theoretically to be scaled by a factor or $\sqrt{\sqrt{2}}$ at each resolution level. Nevertheless, the floating-point computations required to scale coefficients by $\sqrt{\sqrt{2}}$ can impact processing speed. Employing integer operations, such as multiplying by integer correction factors, to compensate for the omission of true floating-point operations, maintains processing speed while sacrificing image accuracy at only some resolution levels.

At step 2970, the server computer 120 transmits data to the client computer thumbnail-resolution images that were the result of the 2-D sub-band transform operations of step 2940. At step 2980, the server computer 120 progressively transmits data representing the identified ROI to the client computer 110.

Figure 30:
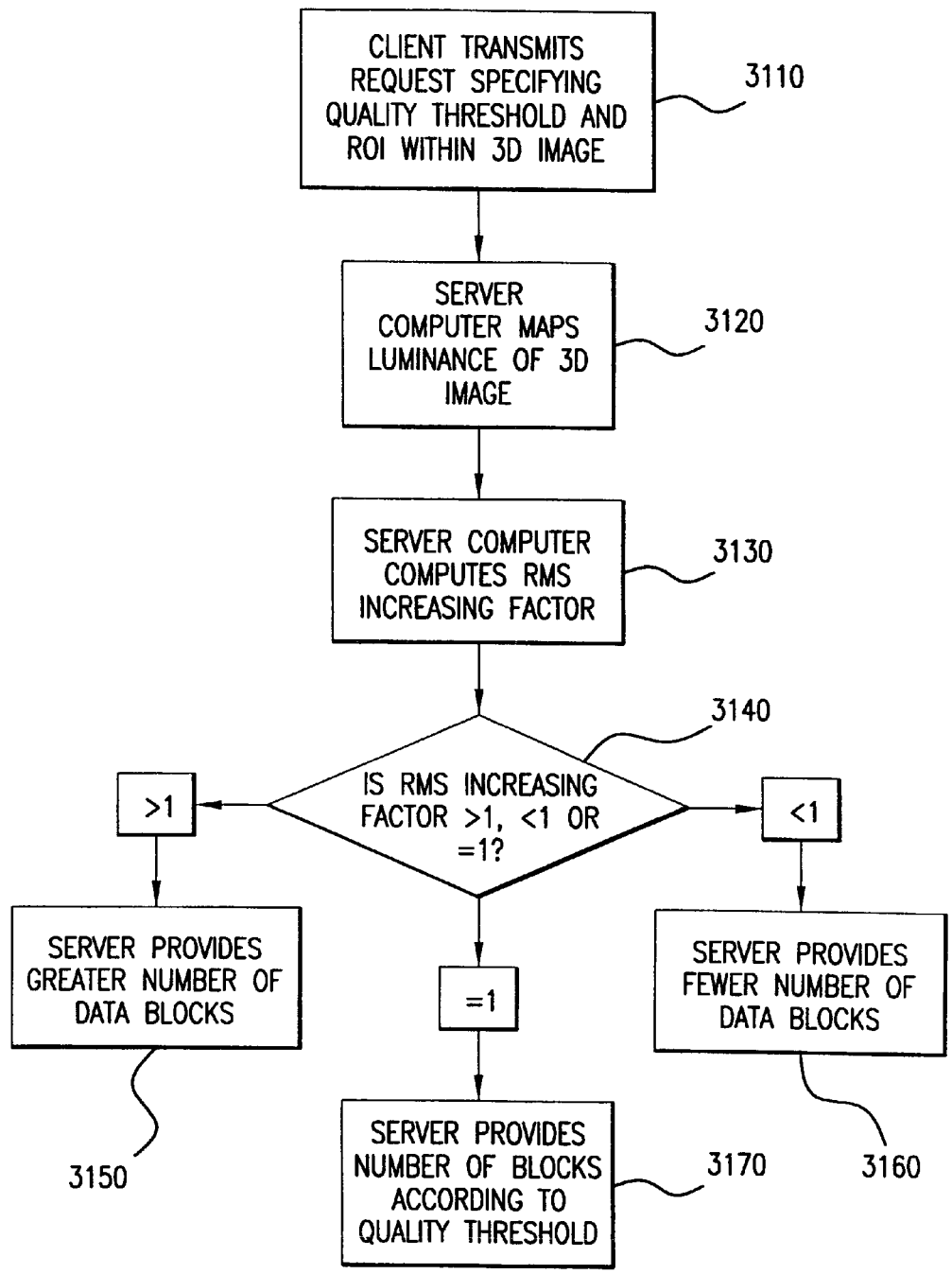
FIG. 30 is a flowchart illustrating a method for transmitting a 3D digital image in accordance with another aspect of the present invention.

FIG. 30 illustrates the method of operation associated with a further aspect of the invention, in which the client request can include not only a request list specifying data blocks that define the ROI but can also include a specified quality threshold. Thus, step 3110 indicates the client computer 110 (FIG. 1) transmitting such a request that includes the request list and a quality threshold. Additionally, the client request can include a specified resolution. At step 3120 the server computer 120 (FIG. 1) can map the luminance of the 3-D image stored on the image storage device from a predetermined image bit depth to a predetermined screen bit depth in accordance with a monotonic luminance mapping function. At step 3130, the server computer 120 computes a root mean square (RMS) increasing factor defined by a maximal derivative of the luminance mapping function. A determination as to whether the RMS increasing factor is greater than one is made at step 3140. Accordingly, the server computer 120 provides more data blocks, i.e., more than some predetermined normal number, if the RMS increasing factor is greater than one at step 3150 and fewer data blocks, i.e., less than the predetermined number, if the RMS increasing factor is less than one at step 3160. If the RMS increasing factor is equal to one, the server computer 120 provides a number of data blocks that is responsive to the specified quality threshold at step 3170.

The basic components of the protocol are accuracy layers associated with tiles of subband/wavelet coefficients. Let I(x,y,z) be a given single component 3-D image such as a grayscale image. It is explained herein below, in reference to Eq. 1, how the protocol is generalized to arbitrary color spaces. Let FWT(I) (Forward Wavelet Transform) be a subband/wavelet transform of the image. A basic introduction to the FWT is not provided in this patent specification because the FWT is in and of itself well known in the art. Transforms used herein are required to be separable. A 3-D separable transform can be computed by three 1D steps: subsequently in the X, Y and Z directions.

Figure 3:
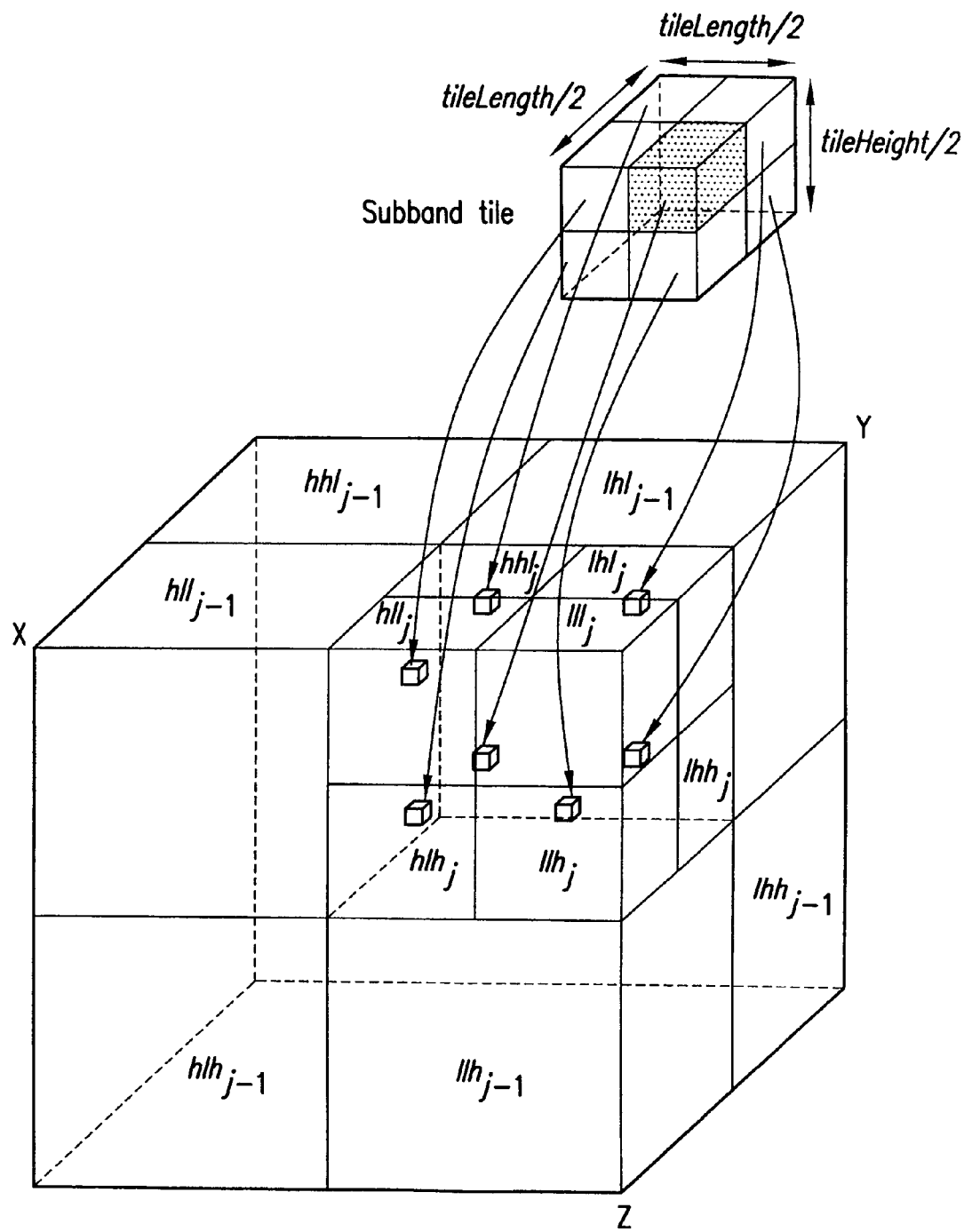
FIG. 3 illustrates subband decomposition and tiling of subband coefficients at given resolution.

Reference is now made to FIG. 3. The wavelet transform typically creates for each given resolution j eight subbands denoted as lll.sub.j, llh.sub.j, lhl.sub.j, lhh.sub.j, hll.sub.j, hlh.sub.j, hhl.sub.j, hhh.sub.j, while only the subband lll.sub.j is passed to the next resolution level processing. Thus, in the typical case the coefficients of FWT(I) are associated with the multiresolution structure shown on FIG. 3. Observe that each coefficient belongs to a particular resolution j.

Figure 4:
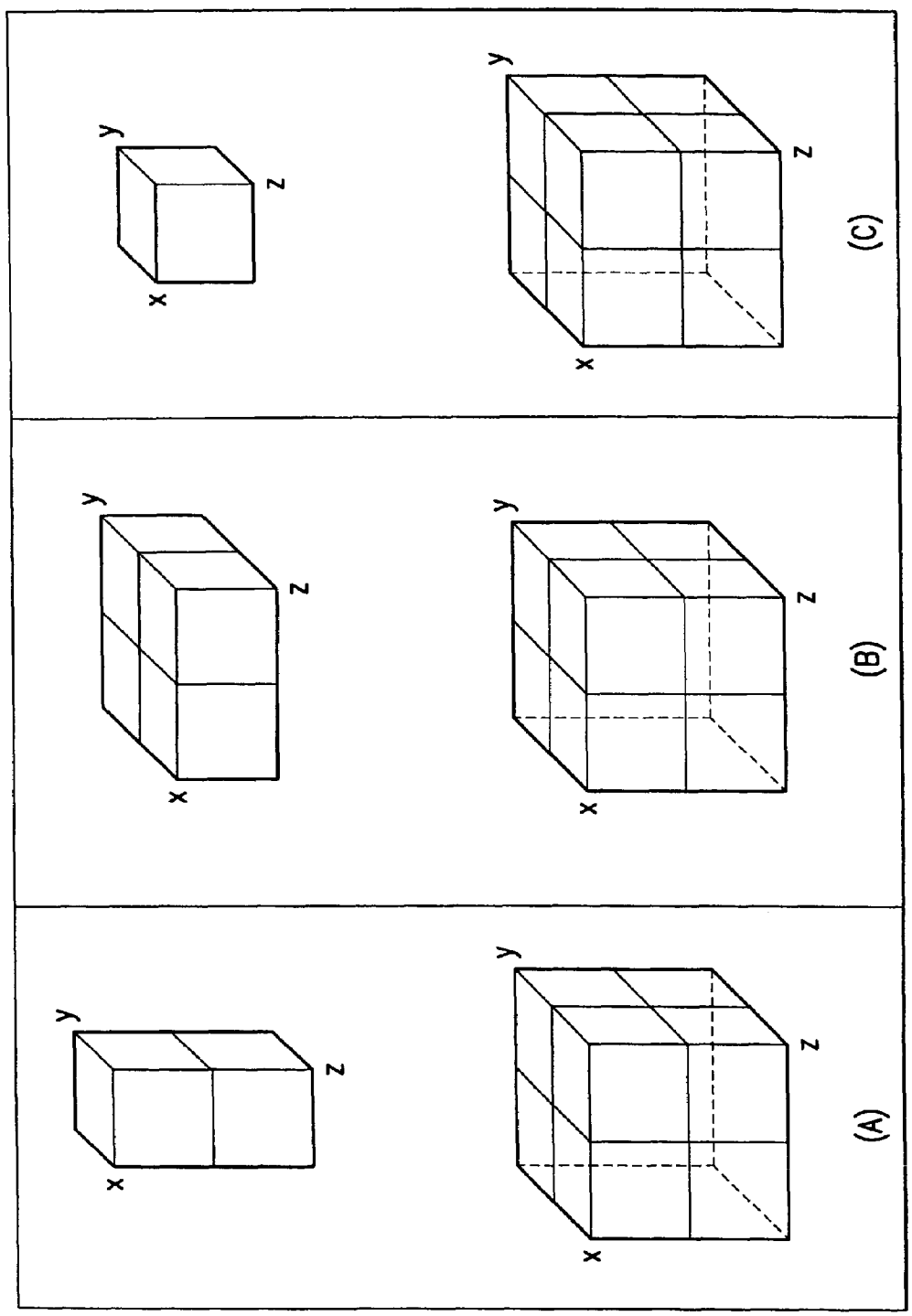
FIG. 4 illustrates subband decomposition types.

Some special kinds of multi-resolution decomposition are introduced in reference to FIG. 4, which pass not only the single subband lll, but also a group of subbands to the next resolution level.

If a Finite Impulse Response (FIR) subband filter (compactly supported wavelet) is used, each coefficient "influences" only a compactly supported region of the image. High resolution/frequency coefficients are associated with a small region and low resolution/frequency coefficients are associated with a larger region. The coefficients are subdivided into tiles as shown in the FIG. 3 for the purpose of efficient rendering. Several subgroups of coefficients are grouped into tiles, associated with the same spatial area, corresponding to the subbands at resolution j that are not passed to the next resolution. In some embodiments of the invention, the sub-tiles can have, for example, a length and width of 32 and height of 1, so that the tile contains $n \times 32^2 \times 1$ coefficients, where n is the number of sub-bands that are not passed to the next resolution. This relates to the fact that at the time of rendering at the client, the subband tile provides a mean to render a tile of size 64×64 2. The parameters tileLength and tileHeight control the size of the subband tiles and can be changed dynamically per 3-D image volume. A 4-D coordinate is associated with each such tile, as described by Eq. 1.

$$\text{Tile} = (t\_x, t\_y, t\_z, t\_\text{resolution}) \quad \text{(Eq. 1)}$$

To generalize the above description for more than one image component, simply associate all the coefficients corresponding to the same spatial location of all the components with the tile of Eq. 1. This yields $n \times 32^2 \times 1 \times \text{numberOfComponents}$ coefficients associated with a multidimensional tile.

Discussion now proceeds to explain how the subband tiles are further decomposed to subband data blocks. The motivation for this finer 5-D decomposition is the following. Each subband tile at the resolution j participates in the rendering of local regions in all the resolutions $\geq j$. Assume j corresponds to a very low resolution. For a high quality rendering of a given ROI at the resolution j, only the coefficients with high absolute value are required. Transmitting small coefficients will not have a significant visual effect at the time of rendering and thus should be avoided. In addition, transmitted coefficients need not be sent at a high precision, since this also will have visual significance to the rendering operation. Rather, for each such significant coefficient only a few bits of precision should be transmitted along with the sign of the coefficient. Rendering the same ROI at a higher quality or rendering a higher resolution requires sending more of the tile's coefficients and also additional accuracy bits for the coefficients that were already sent. For this reason, each subband tile is further decomposed into "accuracy" data blocks. Each data block is associated with the "bit plane" interval [0,2) of level 0 or the intervals $[2^l, 2^{l+1})$ at level $l \geq 1$, so each data block of the subband tile of Eq. 1 will have a 5D coordinate $$\text{Block} = (t\_x, t\_y, t\_z, t\_\text{resolution}, t\_\text{bitPlane}) \quad \text{(Eq. 2)}$$

where $0 \leq t\_\text{bitPlane} \leq \text{maxBitPlane}(t\_\text{resolution})$. The value of maxBitPlane(t_resolution) corresponds to some predetermined constant or selected dynamically according to the largest coefficient at the resolution t_resolution of the given image. In some embodiments of the invention, maxBitPlane (t_resolution)=8 is suitable. The data block of Eq. 2 contains the following data in encoded format:

1. For $t\_\text{bitPlane} \geq 0$, a list of the indices of all subband coefficients whose absolute value is in the range $[2^{t\_bitPlane}, 2^{t\_bitPlane+1})$.
2. The sign of all the coefficients of datum 1.
3. An additional precision bit for any coefficient that belongs to the current bit plane or any higher bit plane is used in one preferred embodiment.

The following two remarks can be made on the description herein above:

First, in case that the subband tile has coefficients whose absolute value $\geq 2^{\text{maxBitPlane}(t\_\text{resolution})+1}$, where maxBit- Plane(t_resolution) is not dynamically selected, their bit plane information, which is the most significant, is inserted into the "highest" possible data block (t_x,t_y,t_z,t_resolution,maxBitPlane(t_resolution)). In such a case this most significant data block contains the data of possibly several bit planes.

Second, in the case of lossy image coding, it is preferable to threshold (discard) all coefficients whose absolute value is below some given threshold $\epsilon$>0. In such a case each data block of Eq. 2 is associated with the bit plane [$\epsilon 2^{t\_bitPlane}$, $\epsilon 2^{t\_bitPlane+1}$). Observe that coefficients whose absolute value is smaller than $\epsilon$ are not reported in any data block and therefore never transmitted.

In some embodiments, the invention can provide a quickly generated thumbnail view of all the slices of the study, the 3-D image. This feature is particularly useful in medical imaging. To provide thumbnails, the system can generate a low resolution representation of a 2-D image at every coordinate Z of the 3-D image. A multi-resolution decomposition of the original 3-D data is employed for this purpose. Before this decomposition is described, 3 types of subband decomposition need to be defined.

FIG. 4 describes three types of subband decomposition. Each type merits different handling as follows:

Case (A) is named herein the HHX-Subbands type. In this case an embodiment of the present invention first performs 2-D wavelet transform for each 2-D image section of the 3-D data having Z=Const, and then performs a wavelet transform in the Z direction on the lh, hl and hh sub-bands of these 2-D transform result. All the ll subbands of the 2-D transform result for every Z are passed to the next resolution.

Case (B) is named herein the XYH-Subbands type. In this case a wavelet transform in the Z direction only is performed first, and then the low-pass result of the transform is passed to the next resolution for each X and Y.

Case (C) is named herein the All-Subbands type of decomposition. In this case a 2-D wavelet transform is first done for each Z, and then the result undergoes the wavelet transform in the Z direction. Only the lll subband of this separable 3-D wavelet transform is passed to the next resolution level.

Figure 5:
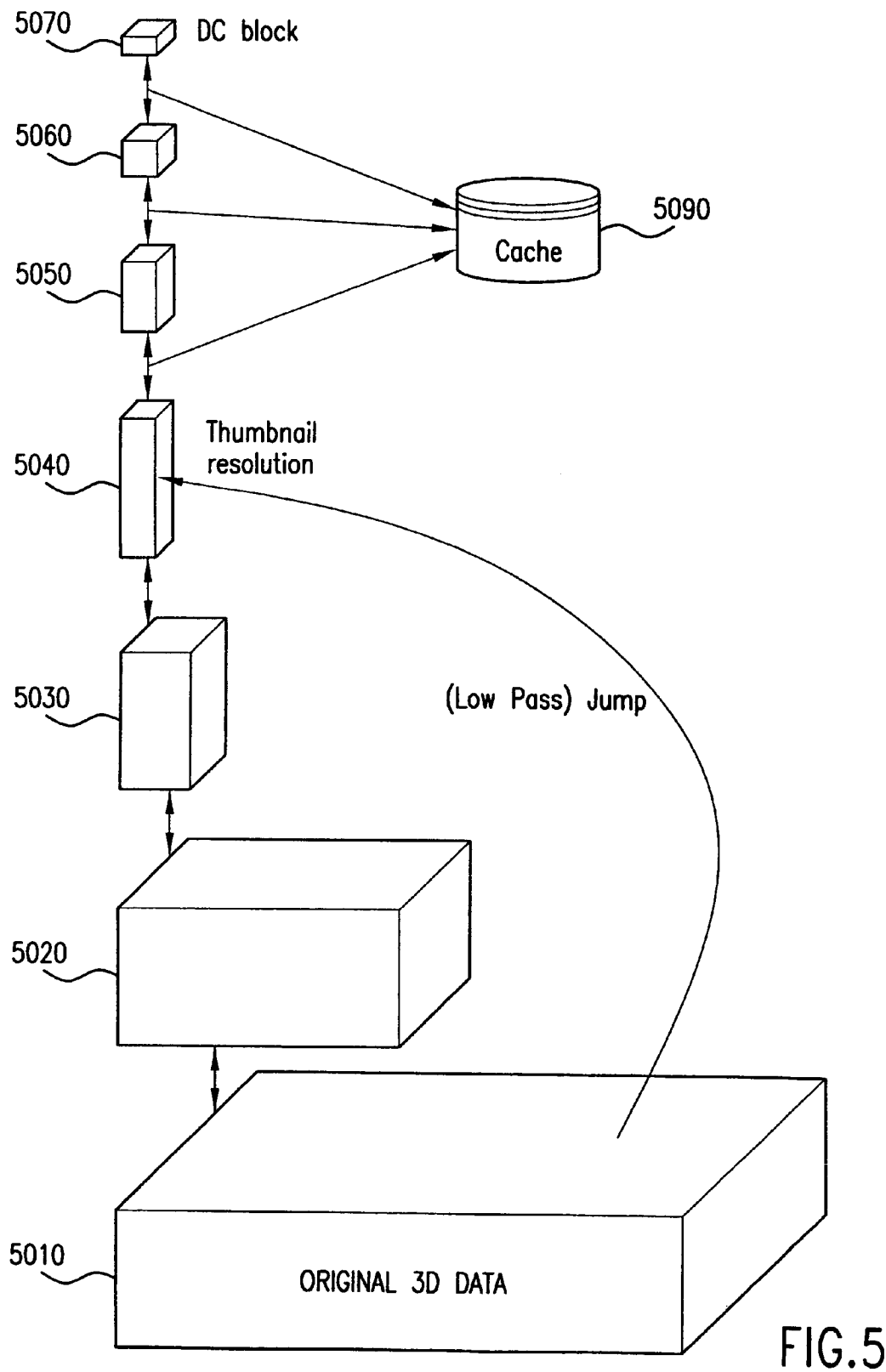
FIG. 5 illustrates a multi-resolution structure of transformed image data.

An embodiment of the present invention for medical applications minimizes the response time for ROI requests from the client by evaluating the multi-resolution decomposition in accordance with the following description with reference to FIG. 5. The embodiment first employs several steps of HHX-Sub-bands type decomposition (steps 5010, 5020, 5030 and 5040) to obtain thumbnail resolution, which is controlled by the predefined parameter thumbnailResolution. Decomposition is employed on slices Z=Const of the original 3-D image. The embodiment then further employs XXH-Sub-bands type decomposition (steps 5050, 5060 and 5070) to reduce resolution in the Z direction alone. The resulting DC block (step 5070) may be further optionally decomposed by the All-Subbands type decomposition. Decomposition such as depicted in FIG. 5 allows quick calculation of all the thumbnail views of every slice of the study and also swift ("near real time") response to any ROI chosen by the client computer 110.

Figure 6:
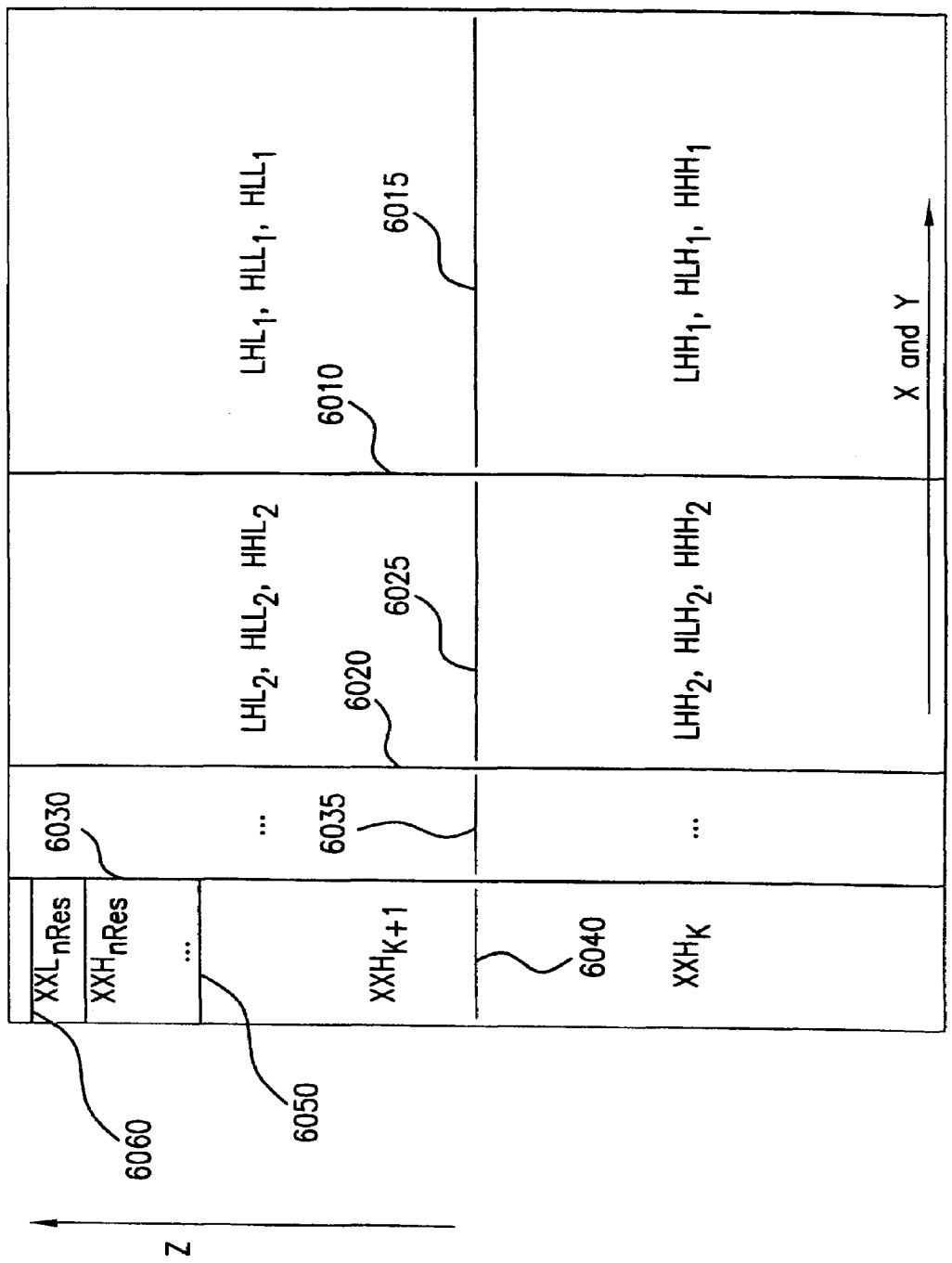
FIG. 6 illustrates multi-resolution decomposition of image data.

The multi-resolution decomposition, mentioned herein above in reference to FIGS. 4 and 5, is shown schematically in FIG. 6 for further clarity. The decomposition of original 3-D image 5010 is executed in two stages, the first stage is depicted by dividing line 6010, and the second stage is depicted by dividing line 6015. The first is done along the X and Y directions, and the second along the Z direction. The decomposition of the resulting image 5020 is executed in two stages, the first is depicted by dividing line 6020, and the second is depicted by dividing line 6025. The first is done along the X and Y directions, and the second along the Z direction. The decomposition of the resulting image 5030 continues until a $k^{th}$ step that is executed in two stages, the first is depicted by dividing line 6030, and the second is depicted by dividing line 6035. The first is done along the X and Y directions, and the second along the Z direction. These first k decompositions are of the HHX-Subbands type. The next decompositions are of the X-Subbands type. The decomposition of image 5040 is depicted by dividing line 6040. The decomposition of image 5050 is depicted by dividing line 6050. Finally, the decomposition of image 5060 is depicted by dividing line 6060.

Embodiments of the present invention can use a separable wavelet transform. Embodiments for lossy applications can use well-known wavelet transforms while embodiments for lossless applications can use wavelet transforms that are described below.

Several embodiments of 2-D Lossless Transforms can be constructed, each based on one of the transforms known in the art. Two embodiments are described herein, the first based on the well-known Haar transform, and the second is based on the lossless version of well-known Cohen-Daubechies-Feauveau (1,3) transform (C.D.F.). Persons skilled in the art can apply the principles described herein below to other transforms.

In 2-D Lossless Transforms, any of such well-known lossless transforms can be employed in the X direction. A similar but different transform is employed in the Y direction. It is modified in each subband to get the proper scaling of the coefficients. Proper scaling means that coefficients are normalized in a $L_2$-norm as do wavelet coefficients computed in an accurate mathematical transform that is not limited to integer numbers.

This is achieved by assignment of so-called HalfBit information to every coefficient belonging to some of the subbands to keep the perfect reconstruction property of the proposed transforms. The calculation of the HalfBit information is explained herein below in reference to Eq. 4c and Eq. 6c.

Denoting by x(n) the $n^{th}$ component of one-dimensional discrete signal, by s(n) and d(n) respectively the low and high pass components of transform, and by the symbol $\lfloor \circ \rfloor$ the floor function meaning "greatest integer less than or equal to $\circ$", e.g. $\lfloor 0.5 \rfloor$=0, $\lfloor -1.5 \rfloor$=−1, $\lfloor 2 \rfloor$=2, $\lfloor -1 \rfloor$=−1 an embodiment of a 2-D lossless wavelet transform can be formulated in the following way.

The following description is based on the Haar transform, initially applied in the X direction. The forward step is the process of coding x(n) to obtain s(n) and d(n). The Haar X direction forward step is given by the following equation.

$$\begin{cases} s(n) = \left\lfloor \dfrac{x(2n) + x(2n+1)}{2} \right\rfloor, \\ d(n) = x(2n+1) - x(2n). \end{cases} \quad \text{(Eq. 3A)}$$

The inverse step is the process of recovering x(n) from s(n) and d(n). The Haar X direction inverse step is given by the following equation.

$$\begin{cases} x(2n) = s(n) - \left\lfloor \frac{d(n)}{2} \right\rfloor, \\ x(2n+1) = d(n) + x(2n). \end{cases} \quad \text{(Eq. 3B)}$$

The Haar-based low part of the Y direction forward step is given by the following equation.

$$\begin{cases} s(n) = x(2n) + x(2n+1), \\ d^{(1)}(n) = \left\lfloor \frac{x(2n+1) - x(2n)}{2} \right\rfloor, \\ d(n) = 2d^{(1)}(n). \end{cases} \quad \text{(Eq. 4A)}$$

Eq. 4A shows the following properties of an embodiment of the present invention. First, $s(n)$ comprises scaled LL-subband coefficient. Second, $s(n)$ and $d^{(1)}(n)$ are a de-correlated and reversible couple i.e. they can be transformed back to $x(2n)$ and $x(2n+1)$), but $d^{(1)}(n)$ is not scaled, so it is assigned half the value used in similar transforms known in the art. Thus, $d^{(1)}(n)$ is multiplied by 2. Third, the LSB of the LH-subband. coefficient $d(n)$ is known to be 0 and not encoded.

The Haar-based low part of the Y direction inverse step is given by the following equation.

$$\begin{cases} x(2n+1) = \frac{1}{2}(s(n) + d(n) + (s(n) \bmod 2)), \\ x(2n) = s(n) - x(2n+1). \end{cases} \quad \text{(Eq. 4B)}$$

The Haar-based high part of the Y direction forward step is given by the following equation.

$$\begin{cases} d^{(1)}(n) = x(2n+1) - x(2n), \\ \mathit{HalfBit}(n) = (d^{(1)}(n)) \bmod 2, \\ d(n) = \left\lfloor \frac{d^{(1)}(n)}{2} \right\rfloor, \\ s(n) = x(2n) + d(n). \end{cases} \quad \text{(Eq. 4C)}$$

Eq. 4C shows the following properties. First, $d^{(1)}(n)$ and $s(n)$ comprise a de-correlated and reversible couple, but $d^{(1)}(n)$ is not scaled, so it is assigned twice the value used in similar transforms known in the art. Therefore, $d^{(1)}(n)$ is divided by 2, which causes its least significant bit to be lost. This least significant bit cannot be restored, unless this bit is kept as the so called Half-Bit information. This name serves as a reminder that its weight is half that of other coefficients and that it is the least significant (from an approximation point of view).

The Haar-based high part of the Y direction inverse step is given by the following equation.

$$\begin{cases} x(2n) = s(n) - d(n), \\ d^{(1)}(n) = 2d(n) + \mathit{HalfBit}(n), \\ x(2n+1) = d^{(1)}(n) + x(2n). \end{cases} \quad \text{(Eq. 4D)}$$

The following description is based on the CDF (1,3) transform, and first in the X direction. The forward step is the process of coding $x(n)$ to obtain $s(n)$ and $d(n)$. The CDF (1,3) X direction forward step is given by the following equation.

$$\begin{cases} s(n) = \left\lfloor \frac{x(2n) + x(2n+1)}{2} \right\rfloor, \\ d^{(1)}(n) = x(2n+1) - x(2n), \\ d(n) = d^{(1)}(n) + \left\lfloor \frac{s(n-1) - s(n+1)}{4} \right\rfloor. \end{cases} \quad \text{(Eq. 5A)}$$

The CDF (1,3) X direction inverse step is given by the following equation.

$$\begin{cases} d^{(1)}(n) = d(n) - \left\lfloor \frac{s(n-1) - s(n+1)}{4} \right\rfloor, \\ x(2n) = s(n) - \left\lfloor \frac{d^{(1)}(n)}{2} \right\rfloor, \\ x(2n+1) = x(2n) + d^{(1)}(n). \end{cases} \quad \text{(Eq. 5B)}$$

CDF (1,3) low part Y direction forward step is given by the following equation.

$$\begin{cases} s(n) = x(2n) + x(2n+1), \\ d^{(1)}(n) = \left\lfloor \frac{x(2n+1) - x(2n) + \left\lfloor \frac{s(n-1) - s(n+1)}{8} \right\rfloor}{2} \right\rfloor, \\ d(n) = 2d^{(1)}(n). \end{cases} \quad \text{(Eq. 6A)}$$

CDF (1,3) low part Y direction inverse step is given by the following equation.

$$\begin{cases} s^{(1)}(n) = s(n) - \left\lfloor \frac{s(n-1) - s(n+1)}{8} \right\rfloor, \\ x(2n+1) = \frac{1}{2}(s^{(1)}(n) + d(n) + (s^{(1)}(n) \bmod 2)), \\ x(2n+1) = s(n) - x(2n+1). \end{cases} \quad \text{(Eq. 6B)}$$

CDF (1,3) high part Y direction forward step is given by the following equation.

$$\begin{cases} s(n) = \left\lfloor \frac{x(2n) + x(2n+1)}{2} \right\rfloor, \\ d^{(1)}(n) = x(2n+1) - x(2n), \\ d^{(2)}(n) = d^{(1)}(n) + \left\lfloor \frac{s(n-1) - s(n+1)}{4} \right\rfloor, \\ d(n) = \left\lfloor \frac{d^{(2)}(n)}{2} \right\rfloor, \\ \mathit{HalfBit}(n) = d^{(2)}(n) \bmod 2. \end{cases} \quad \text{(Eq. 6c)}$$

CDF (1,3) high part Y direction inverse step is given by the following equation.

$$\begin{cases} d^{(1)}(n) = 2d(n) + \text{HalfBit}(n) - \left\lfloor \frac{s(n-1) - s(n+1)}{4} \right\rfloor, \\ x(2n) = s(n) - \left\lfloor \frac{d^{(1)}(n)}{2} \right\rfloor, \\ x(2n+1) = d^{(1)}(n) + x(2n). \end{cases} \quad \text{(Eq. 6d)}$$

2-D Lossless Transforms have better approximation properties of the exact mathematical wavelet transform than previous known separable implementations of the one-dimensional lossless transform.

The fact that the 2-D transform requires two sequential 1D transforms allows 2-D Lossless Transforms to mutually compensate the scale distortion of 1D lossless wavelet transform and to keep the proper scaling of wavelet coefficients as described herein above in reference to Eq.'s 4a through 6d and in the above-referenced U.S. patent application Ser. No. 60/198,017. It is impossible to apply the same method in the case of 3-D lossless wavelet transform. Instead, the present invention modifies the lossless 1D Haar transform in such a way that allows it to keep the wavelet coefficients as close to their scaled values as possible and to decrease the scatter of scaling factors in different subbands at all the resolution levels.

The present invention uses a transform in the form of the following equation for HHX-Subbands type decomposition for the coefficients belonging to the HL and HH subbands of the 2-D slices $$\begin{cases} s(n) = z(2n) + z(2n+1), \\ d(n) = \left\lfloor \frac{z(2n) - z(2n+1)}{2} \right\rfloor \times 2 \end{cases} \quad \text{(Eq. 7A)}$$

The following different equation is used for the coefficients from the LH subband of the 2-D slices that already have LSB equal 0.

$$\begin{cases} s(n) = z(2n) + z(2n+1), \\ d(n) = \left\lfloor \frac{z(2n) - z(2n+1)}{4} \right\rfloor \times 4. \end{cases} \quad \text{(Eq. 7B)}$$

This means that hlh subband of this 3-D transform has its two last bits equal to 0.

Eq. 7B scales s(n) and d(n) by a factor of $\sqrt{2}$. Because of the fact that all the coefficients resulting from the 2-D Lossless Transforms are scaled properly, all the wavelet coefficients of our entire 3-D transform are scaled in total effect by $\sqrt{2}$ in this case.

The inverse transforms for Eq's 7A and 7B are 7C and 7D respectively.

$$\begin{cases} z(2n) = \frac{1}{2}(s(n) + d(n) + (s(n) \bmod 2)) \\ z(2n+1) = s(n) - z(2n) \end{cases} \quad \text{(Eq. 7C)}$$

$$\begin{cases} z(2n) = \frac{1}{2}(s(n) + d(n)) + \left(\frac{1}{2}s(n)\right) \bmod 2 \\ z(2n+1) = s(n) - z(2n). \end{cases} \quad \text{(Eq. 7D)}$$

It should be mentioned that the resulting low-resolution 2-D image, that is passed to the next resolution processing is properly scaled. It should be also noted that, as explained herein above, it does not undergo a transform in Z direction.

A single one-dimensional lossless wavelet transform does not preserve the scaling of the resulting coefficients, but the requirement exists, as explained hereinabove in reference to FIGS. 5 and 6 for XXH-Subbands type decomposition, to use a one-dimensional transform. The present invention overcomes this difficulty in the following way: Two different transforms are implemented in turn. In one of them, the resulting lowpass coefficients are scaled by a factor of {square root}{square root over (2)}, and in another they are scaled by {square root}{square root over (2)}.sup.−1. This preserves overall scaling of the low pass fraction. In other words, every odd time Eq. 7A is used for the forward step and Eq. 7C for the inverse step, and every even time the following Eq. 7E is used for the forward step, and Eq. 7F for the inverse step.

$$\begin{cases} s(n) = \left\lfloor \frac{z(2n) + z(2n+1)}{2} \right\rfloor, \\ d^{(1)}(n) = z(2n) - z(2n+1), \\ \text{HalfBit}(n) = (d^{(1)}(n)) \bmod 2, \\ d(n) = \left\lfloor \frac{d^{(1)}(n)}{2} \right\rfloor \end{cases} \quad \text{(Eq. 7E)}$$

$$\begin{cases} z(2n) = s(n) + d(n) + \text{HalfBit}(n), \\ z(2n+1) = s(n) - d(n). \end{cases} \quad \text{(Eq. 7F)}$$

Figure 7:
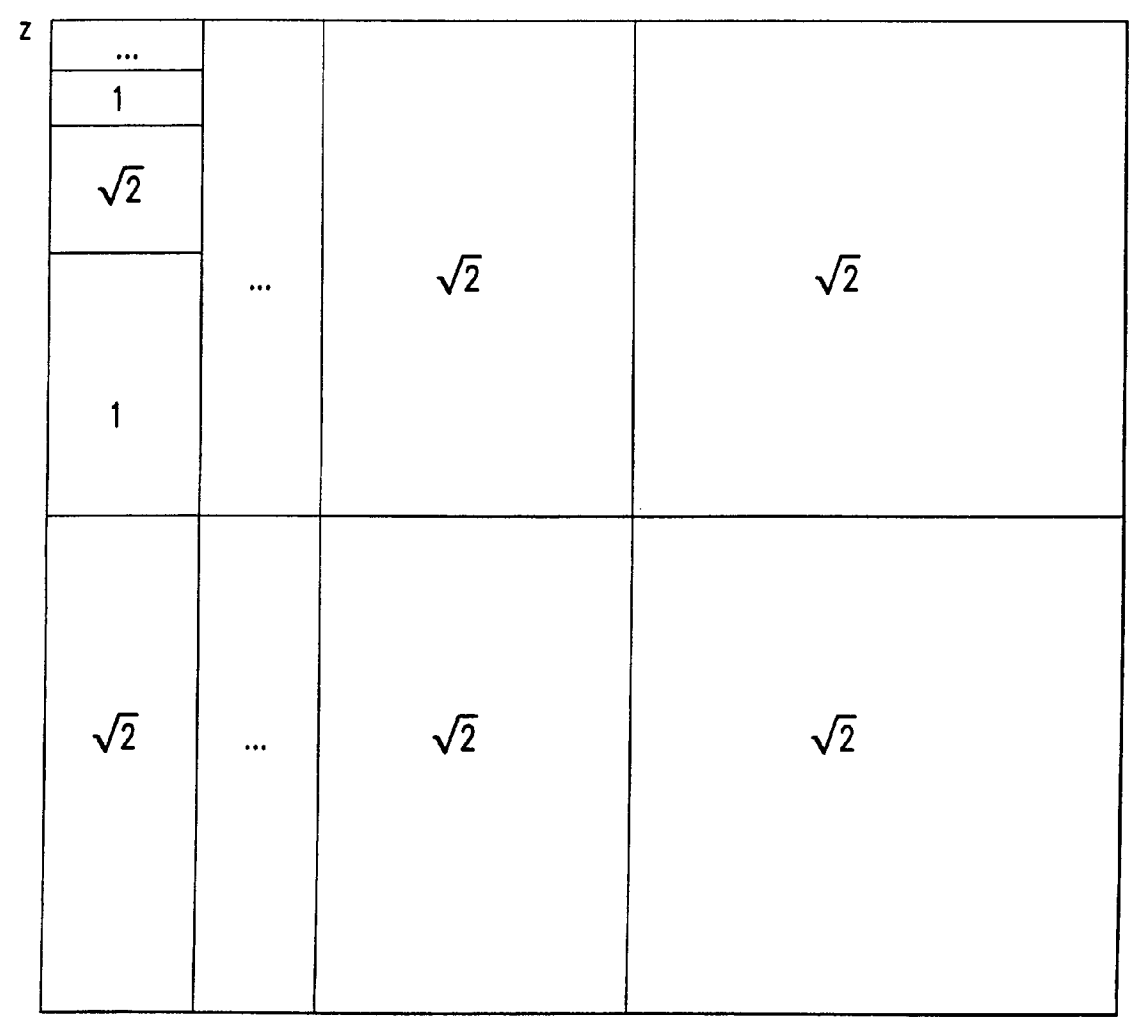

The resulting scaling factors of wavelet coefficients for all subbands in the proposed multiresolution decomposition are shown on FIG. 7. It can be seen that with the present invention all the coefficients are almost equally scaled.

As for the All-Subbands type decomposition, which is optionally implemented and only for the lowest resolution (or DC) block, the present invention uses the combination of HHX-Subbands and XXH-Subbands types of decompositions.

Figure 8A:
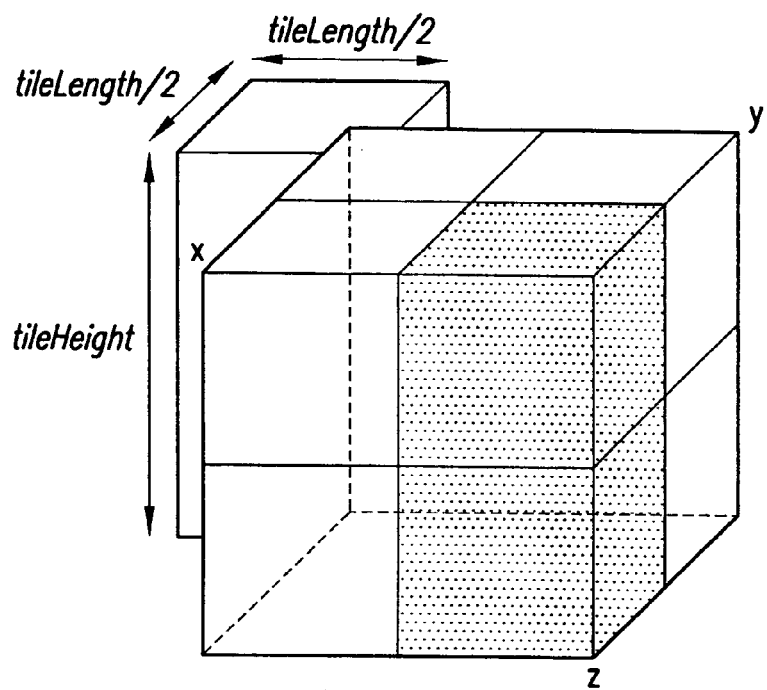
FIG. 8 illustrates tile dimensions and the addition of half-bit information planes for lossless subband decomposition types.
Figure 8B:
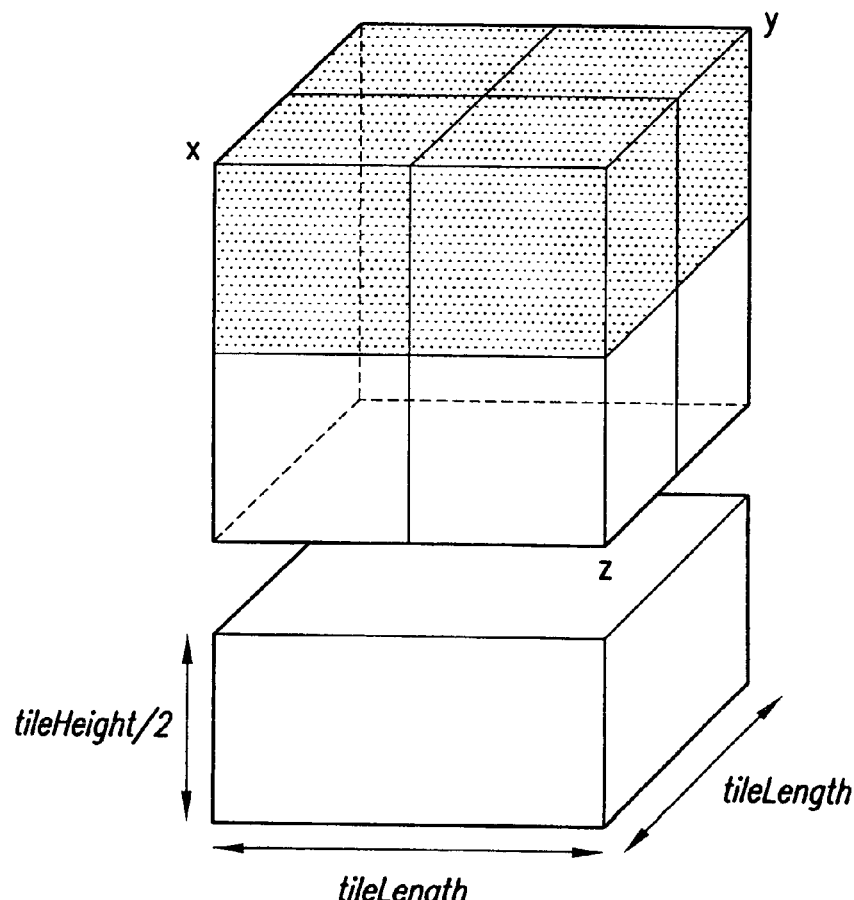

Reference is now made to FIG. 8. The figure depicts data blocks as defined in Eq. 2. Embodiments of the present invention for lossless transformation utilize two additional "half bit planes", one of which is associated with 2-D wavelet transforms on the XY plane as explained in reference to Eq's 3 through 6. The other is associated with a transform in the Z direction as explained in reference to Eq's 7. Each of these two "half bit planes" is implemented as a three-dimensional matrix. For the HHX-Subbands type decomposition this matrix has size (tileLength/2)×(tileLength/2)×tileHeight while for the XXH-Subbands type decomposition this matrix has size tileLength×tileLength×(tileHeight/2).

Thus, each data block for lossless implementation contains the following data in encoded format:

1. For t_bitPlane$\geq$2
   a. A list of the indices of all subband coefficients whose absolute value is in the range $[2^{t\_bitPlane-1}, 2^{t\_bitPlane})$.
   b. The sign of all the coefficients of 1.a.
   c. For t_bitPlane>2, an additional precision bit for any coefficient that belongs to the current bit plane or any higher bit plane.

These are exactly the same data as for the lossy case.
2. For t_bitPlane=1, which is called herein the "least significant bit plane":
   a. A list of the indices of coefficients whose absolute value belongs to the set {−1,0,1} from HLH and HHH-subbands for HHX-Subbands type of decomposition or from HLH and HHH-subbands for XXH-Subbands at even resolution type of decomposition or all subbands for XXH-Subbands type of decomposition at odd resolutions.
   b. A "zero flag" for each coefficient of 2.a, which indicates if the coefficient is equal to zero or not.
   c. The sign of all the coefficients of 2.a, whose "zero flag" is false.
   d. The LSB of the coefficients from 2.a that belong to higher bit plane.

Note that since the remaining subbands contain only even coefficients, their LSB must be zero and is not coded.

3. For t_bitPlane=0 which is called herein the "half bit plane", a matrix of (tileLength/2)×(tileLength/2)×tileHeight bits for HHX-Subbands type decomposition, or a matrix of tileLength×tileLength×(tileHeight/2) bits for XXH-Subbands type decomposition as their last "half bit".

The encoding algorithm employs the forward steps described above with reference to Eq's 3 through 7. It is performed at the server, which is block 120 in FIG. 1. The present invention is an imaging system that enables this time consuming task to be swiftly performed for a specific ROI and not necessarily on the full image. The following is a description the encoding algorithm for images with a single color component such as grayscale images. The straightforward generalization for an arbitrary number of components is explained later. The algorithm receives as input the following parameters listed in Table 1.

TABLE 1

Encoding Algorithm input parameters

| Variable | Meaning |
|---|---|
| coef | 3D matrix of subband coefficients, containing either 3 × (tileLength/2) × (tileLength/2) × tileHeight coefficients for HHX-Subbands type decomposition or tileLength × tileLength × (tileHeight/2) coefficients for XXH-Subbands type decomposition. |
| EqualBinSize | Boolean: True for high or lossless quality. False for low quality. |
| $\epsilon_c$ | The minimal threshold for the component. |
| HalfBit | A 3D matrix of bits containing (tileLength/2) × (tileLength/2) × tileHeight bits for HHX-Subbands type decomposition or tileLength × tileLength × (tileHeight/2) bits for XXH-Subbands type decomposition. |

At any given time in the encoding algorithm a coefficient belongs to one of three types of groups:
1. Type16: A group of 4×4×1 coefficients (B group)

{coef(4i+x,4j+y,k),x∈[0,3],y∈[0,3]}

2. Type4: A group of 2×2×1 coefficients (A group)

{coef(2i+x,2j+y,k),x∈[0,1],y∈[0,1]}

3. Type1: Single coefficient

A Type16 group is also named herein a 'B' group, and a Type4 group is also named herein as 'A' group.

In a general case, the size of the A and B groups of coefficients may be controlled by parameters such as the following:

Coef. A Group Length in X and Y,
Coef A Group Length in Z.
A groups In a B Group in X and Y,
A groups In a B Group in Z, which allow flexible control of coefficients grouping. The sizes need not necessarily be 4 and 16.

Figure 27:
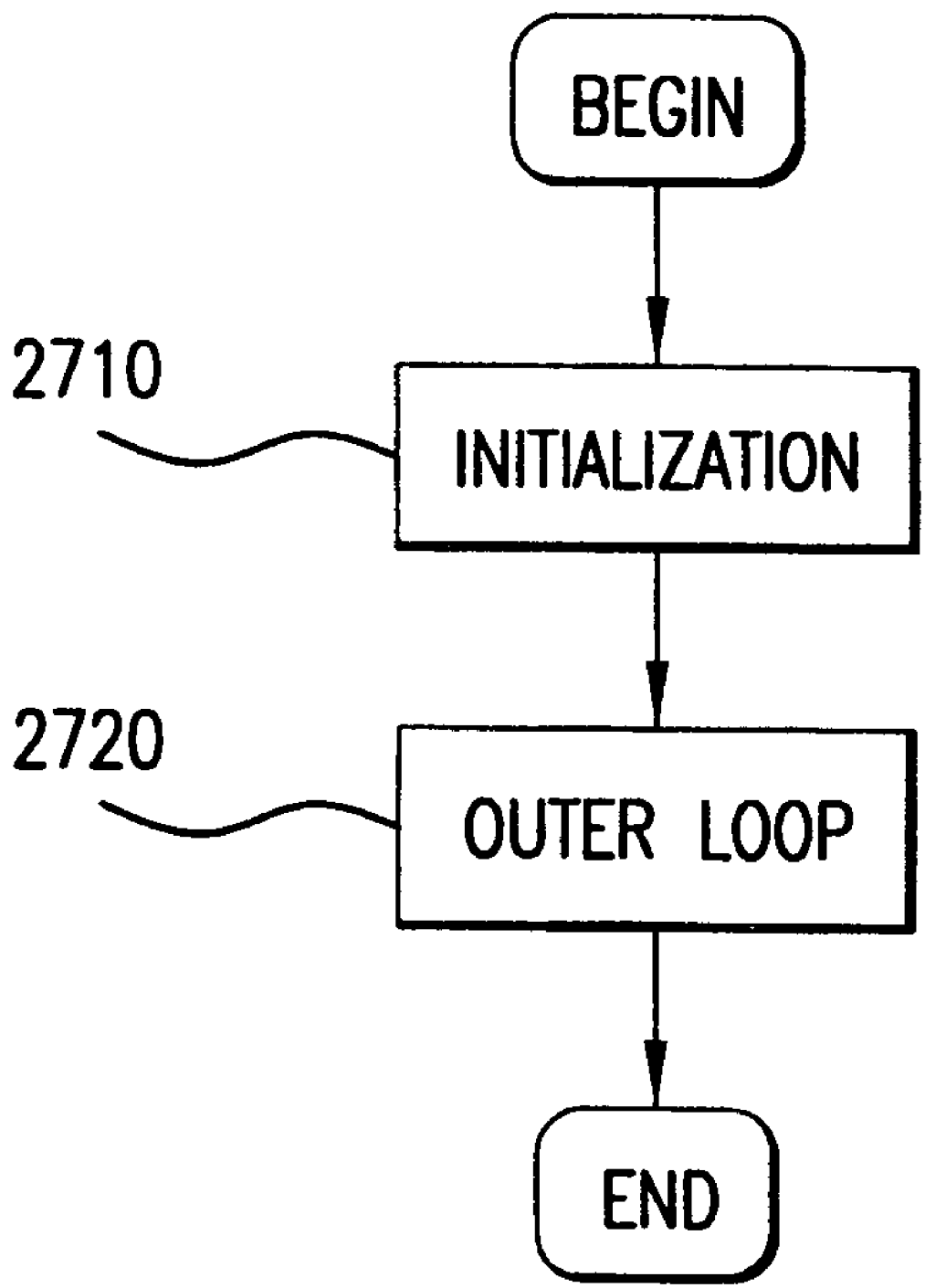
FIG. 27 is a flowchart illustrating the encoding algorithm principal steps of the present invention.

The encoding algorithm is now described in reference to FIG. 27. The encoding algorithm principal steps are the following. Step 2710 is an initialization, and step 2720 is an outer loop in which the inner loops nest.

The first step in the encoding algorithm is its initialization (step 2710), which is conducted as follows.
1. Assign to each coefficient coef (x,y,z) its bit plane such that $|coef(x,y,z)| \in [\epsilon 2^b, \epsilon 2^{b+1})$ where $\epsilon = \epsilon_c$ for lossy applications and $\epsilon = 2^{-1}$ for lossless ones.
2. Compute the maximum bit plane over all such coefficients $$\max BitPlane(tile) = \max_{x,y,z}(b(x, y, z))$$

3. Write the value of maxBitPlane(tile) using one byte as the header of the data block (t_x,t_y,t_z,t_resolution,maxBitPlane(t_resolution)).

4. Initialize all the coefficients as members of their corresponding Type16 group.
5. Initialize a list of significant coefficients to be empty.
6. Initialize a coefficient approximation matrix coef as zero.

Figure 13:
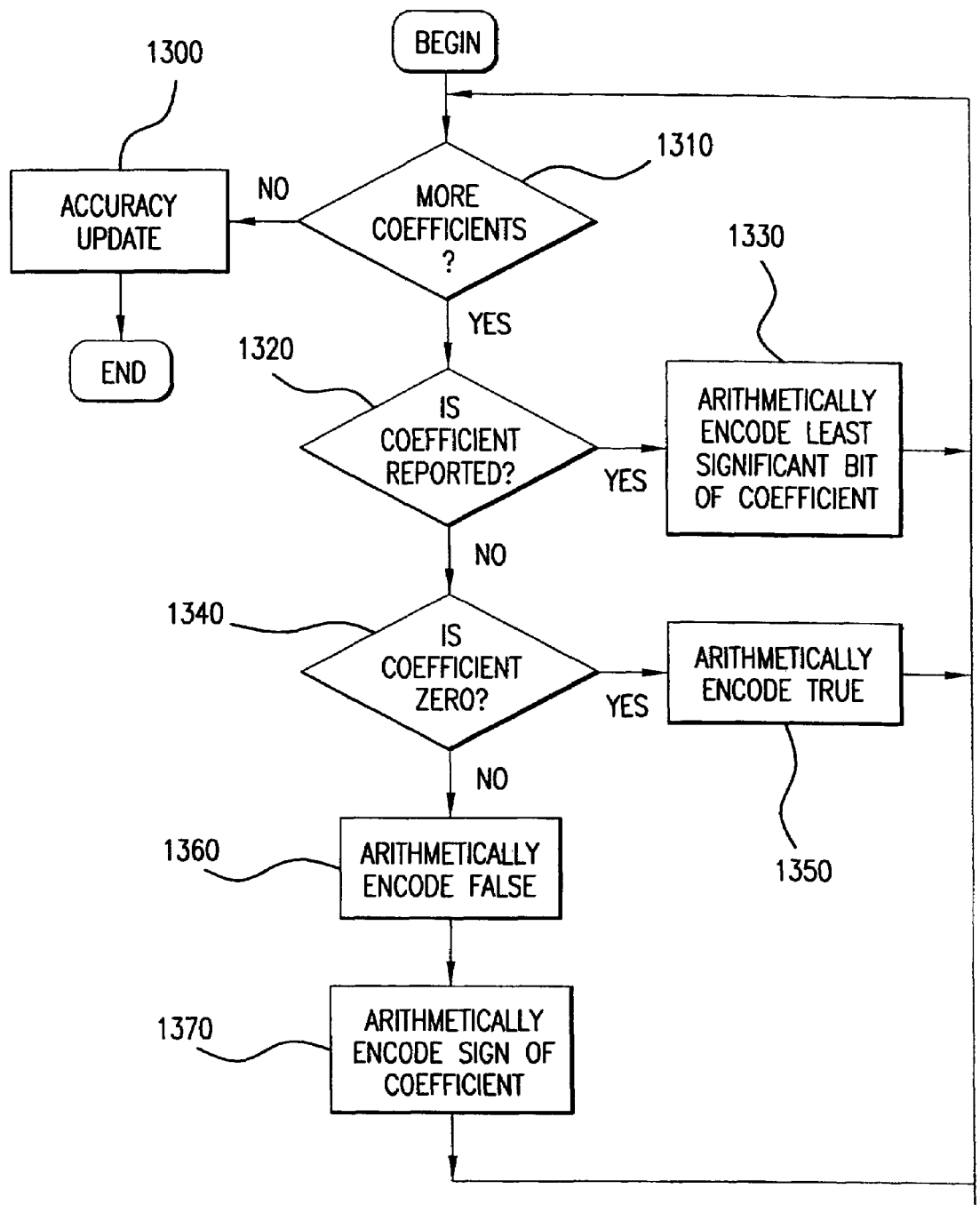
FIG. 13 illustrates a least significant bit plane scan encoding algorithm flowchart.

The second step in the encoding algorithm (step 2720) can be conducted as follows with reference to FIG. 9. The encoding algorithm scans the bit planes from b=maxBitPlane(tile) to b=0 (step 910).The output of each such bit plane scan is the subband data block defined in Eq. 2. Since the last stage of the encoding algorithm is arithmetic encoding of given symbols, at the beginning of each scan (step 920) the arithmetic encoding output module is redirected to the storage area allocated for the particular data block. Once the bit plane scan is finished and the data block defined in Eq. 2 has been encoded (step 940), the output stream is closed (step 950) and the bit plane is decremented (step 960). The last two bit planes for the lossless applications are the "least significant bit plane" (b=1) and the "half bit plane" (b=0), as described in reference to FIG. 8. The following description with reference to FIG. 10A, FIG. 10B and FIG. 11 is true for the case b>1, while the description with reference to FIG. 12A and FIG. 13 is true for the case b=1 and FIG. 12B is true for the case b=0.

Figure 9:
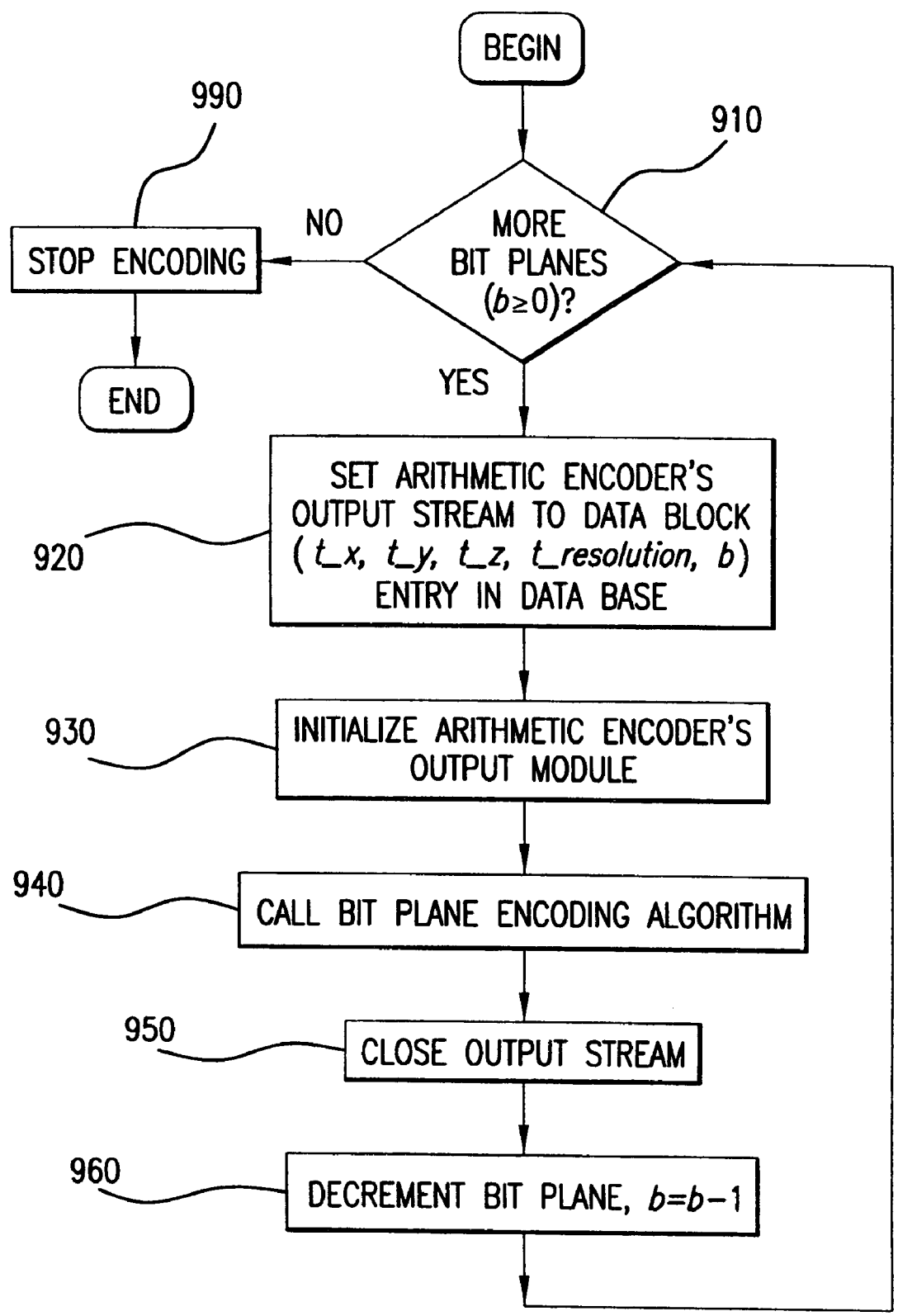
FIG. 9 is a flowchart illustrating a server encoding algorithm outer loop.
Figure 10A:
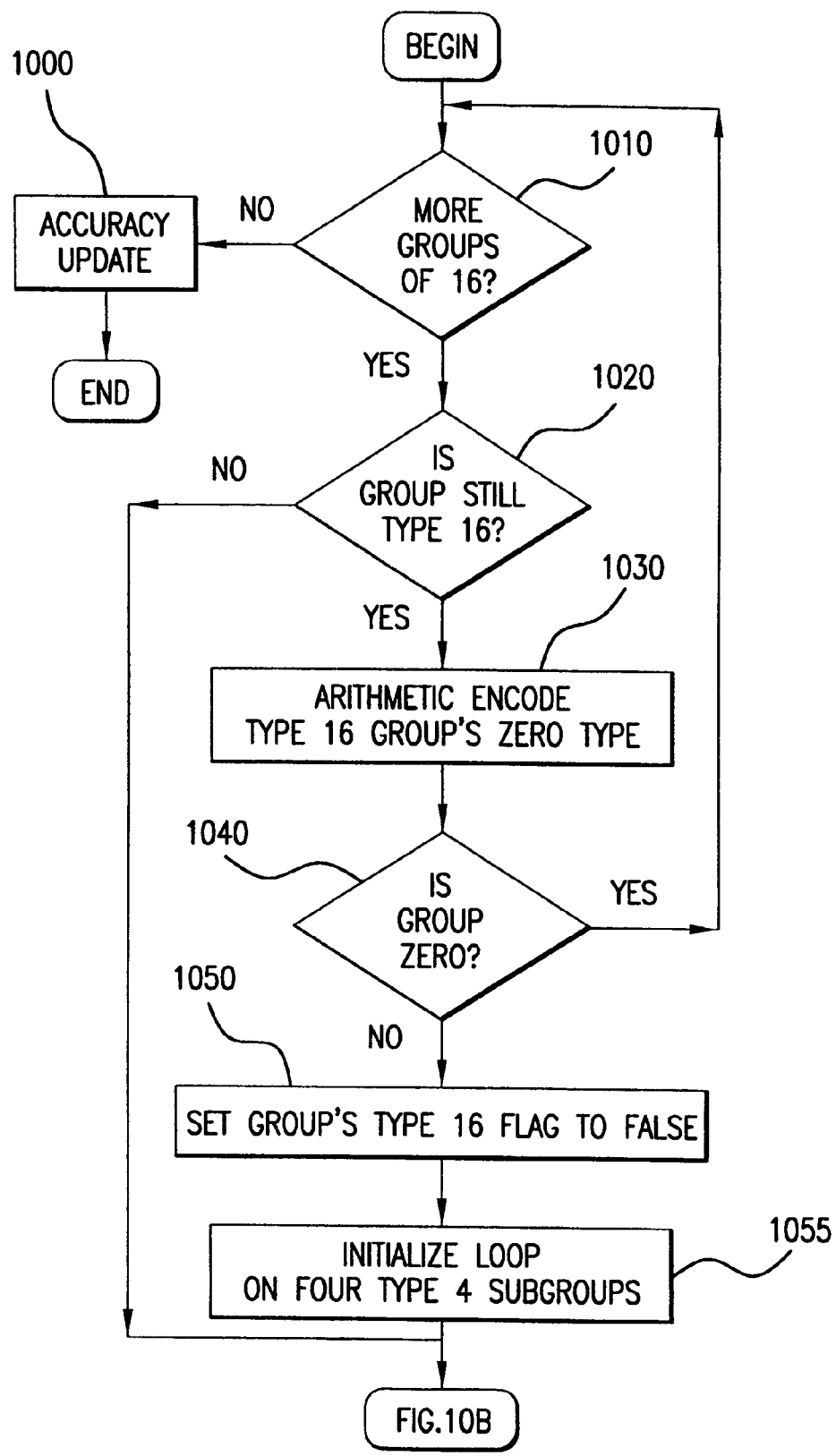
FIG. 10A illustrates a server encoding algorithm bit plane significance scan flowchart.
Figure 10B:
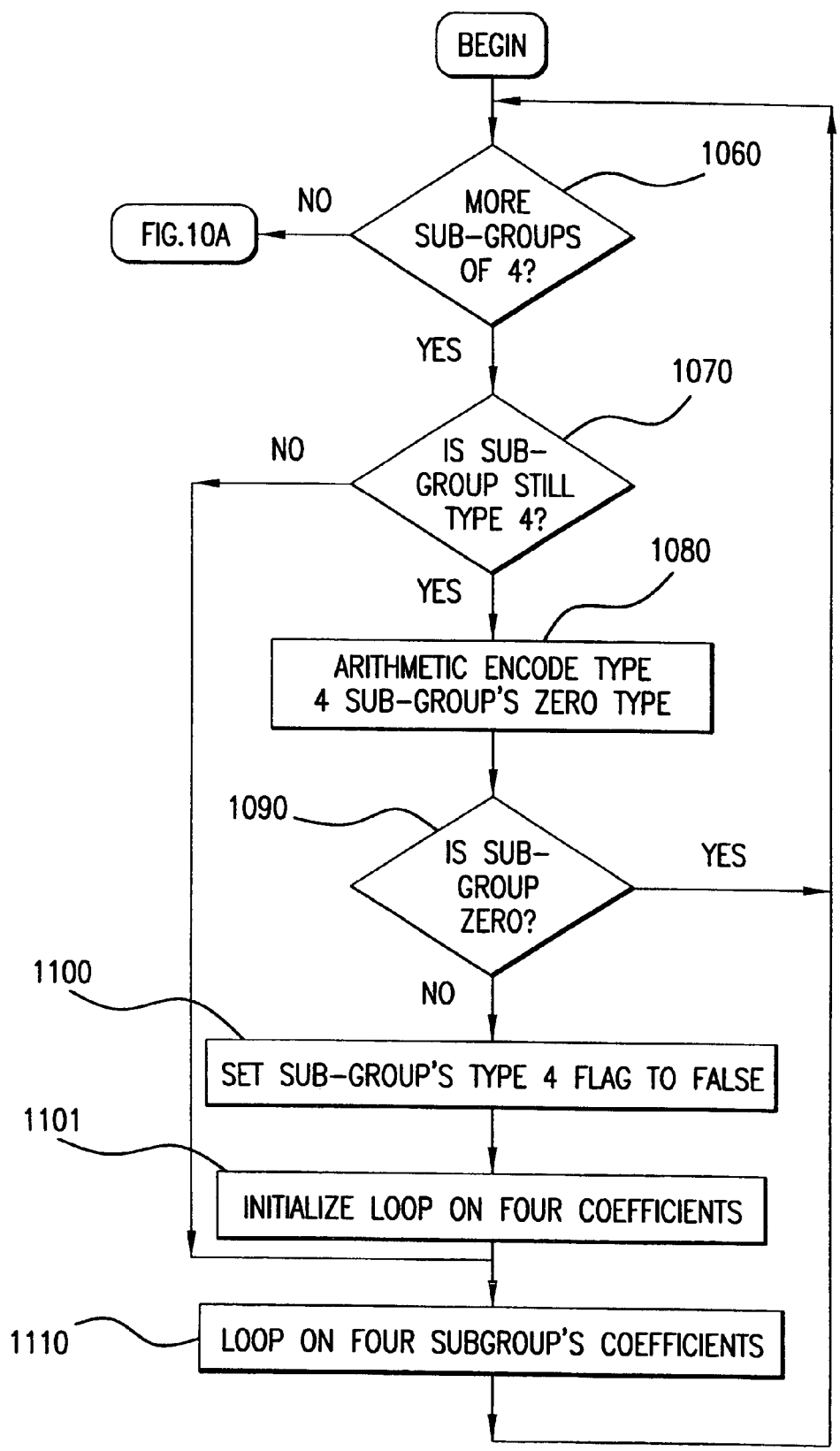
FIG. 10B illustrates a server encoding algorithm, bit plane significance scan flowchart.

The process of encoding per bit plane (step 940) in FIG. 9, is now described in detail with reference to FIG. 10A, FIG. 10B and FIG. 11. A flowchart is depicted in FIG. 10A and FIG. 10B and equivalent pseudo-code is listed in FIG. 11. The scan, for a given level b, encodes all of the coefficients' data corresponding to the absolute value interval $[\epsilon 2^b, \epsilon 2^{b+1})$ where $\epsilon = \epsilon_c$ for lossy applications and $\epsilon = 2^{-1}$ for lossless ones, as described with reference to FIG. 3 and FIG. 8

As with any progressive subband-coding algorithm, the goal is to efficiently encode the locations of the coefficients that are "exposed" when encoding traverses down to the current bit plane. Naturally, the encoder and decoder have at the time of the scan all the information on what "took place" at the previous higher bit plane scans. As with most methods, the heuristics of the algorithm is that coefficients, which are insignificant at the current bit plane, which are coefficients with absolute value $<\epsilon 2^b$, are spatially correlated. If it is known that a coefficient is insignificant at the bit plane b then the probability is higher that the neighbors of the coefficient are insignificant as well. This explains why the algorithm groups coefficients into groups of 16 and then 4 and tries to efficiently report (with one symbol) their insignificance. The significance scan uses four binary probability models as listed in the following table.

TABLE 2

| Model | Use |
|---|---|
| Type16 | to model significance of the groups of 16 |
| Type4 | to model significance of the groups of 4 |
| Type1 | to model significance of single coefficients |
| Sign | to model the sign of a significant coefficient |

The models listed in Table 2 are histograms with two levels. They are initialized to equal probabilities at the beginning of each significance scan and are used and updated by the arithmetic encoder each time a symbol is encoded. Description now proceeds to details of the significance scan.

As depicted in FIG. 10A, a first loop uses a test (step 1010) on groups of 4×4 coefficients. If there are no more such groups the significance scan is terminated and encoding proceeds to an accuracy update in (step 1000). If the current group is still labeled Type16 (step 1020) the encoder computes $$b\_group = \max_{x,y,z \in group16} b(x, y, z)$$

and arithmetic encodes the Boolean value b_group<b (computed in step 1030). If b_group<b (step 1040), then the group is currently insignificant and encoding proceeds to the next group. Else, the encoder removes the label Type16 (step 1050), splits the group to 4 subgroups of 2×2 coefficients and labels each of them Type4. If the group of 16 was not labeled Type16 (step 1020) then it must have been split at a higher bit plane. In both cases the next step will handle the four subgroups of four coefficients.

The encoder iterates over the subgroups of four coefficients (step 1070). If a subgroup is labeled Type4 the encoder again computes $$b\_subgroup = \max_{x,y,z \in subgroup} b(x, y, z)$$

and arithmetically encodes the value of the test b_subgroup<b. There is no need to perform the arithmetic encoding step if the following three conditions hold true:
1. The current group is the fourth subgroup.
2. The previous three subgroups are still labeled Type4.
3. The four subgroups were created "just now" at the current scan by splitting a group of 16.

Under these conditions it is certain that b_subgroup≧b, or else the split would not have taken place. Thus, there is no need to arithmetically encode the significance of the subgroup, since this information will be known also to the decoder at this stage.

If the current subgroup is found to be (still) insignificant the encoder proceeds to the next subgroup. Else, it removes the label Type4, split the subgroup to the single coefficients and label each of them Type1 (step 1100). If the subgroup was not labeled Type4 then it must have been split at a higher bit plane. In both cases the next task is to handle each individual coefficient.

The iteration performed over the four coefficients in step 1110 in FIG. 10B is now explained in detail. If a coefficient coef(x,y,z) is labeled Type1 the encoder arithmetically encodes the value of the test b(x,y,z)<b . There is no need to perform the arithmetic encoding step if the following three conditions hold true:
1. The current coefficient is the fourth coefficient.
2. The previous three coefficients are still labeled Type1.
3. The subgroup of the four coefficients was split "just now" at the current scan.

Under these conditions it is certain that b(x,y,z)≧b, or else the split would not have taken place. As in the subgroup case, there is no need to arithmetically encode the significance of the coefficient.

If the current coefficient is still found to be insignificant, then encoding proceeds to the next coefficient, else, the encoder arithmetically encodes the sign of the coefficient, remove the label Type1 and adds the coefficient to the list of significant coefficients. The encoder now sets $$coef(x, y, z) = \text{sign}(coef(x, y, z)) \times \varepsilon \times \frac{3 \times 2^b}{2}$$

The value of coef(x,y,z) simulates the reconstruction of the coefficient by the decoder. At this stage, with no additional information available, this will be the approximated value of the coefficient by the decoder, which corresponds to the middle of the bit plane interval $[\epsilon 2^b, \epsilon 2^{b+1})$.

The encoding accuracy update of step 1000 in FIG. 10A in now explained in detail. This step is performed if one of the following two conditions holds:
1. equalBinSize=false (see Table 1)
2. b>0

At the bit plane b the significant coefficient list contains all the coefficients coef(x,y,z) for which b(x,y,z)≧b and their current approximated value coef(x,y,z). For each coefficient in the list the encoder arithmetically encodes the value of the test coef(x,y,z)<coef(x,y,z). To that end, a special binary probability model is initialized at the beginning of the step and used by the arithmetic encoder. After the accuracy improvement has been encoded, the encoder accordingly simulates the reconstruction done by the decoder and updates the coefficient's approximated value by adding/subtracting from coef(x,y,z) the amount $$\varepsilon \times \frac{2^b}{4}.$$

Reference is now made to FIG. 12A and FIG. 13, for the description of the encoding at the least significant bit plane. This is a detailed description of step 940 in FIG. 9, for the special case of b=1. Pseudo-code is provided in FIG. 12A, and an equivalent flowchart is shown in FIG. 13. The least significant bit encoding algorithm is as follows.

The coefficients scanning procedure in step 1210 in FIG. 12A and step 1310 in FIG. 13 skips all the coefficients that belong to those subbands that have zero least significant bits in all coefficients, as described in detail herein above in reference to FIG. 8.

The test for reported coefficients procedure in step 1220 in FIG. 12A and step 1320 in FIG. 13 returns false if the coefficient is one of {−1,0,1} (as in all higher bit plane scans it was insignificant), otherwise it returns true. The test for zero coefficients in step 1230 in FIG. 12A and step 1330 in FIG. 13 returns true if and only if the coefficient is zero.

The half bit plane scan is now described in reference to the pseudo-code shown in FIG. 12B. A scan is made in the three dimensions, labeled x, y and z. In each dimension the scan is made from zero to the size in that dimension. A symbol in encoded arithmetically in each point of the 3-D space. Clearly, the scan could be made in any other particular order such as the reverse order to that embodiment depicted in FIG. 12B, as long as the encoder and the decoder agree on the order of the scan. The decoder algorithm is explained herein below, and the relevant decoder scan is described with reference to FIG. 16B.

The decoding algorithm is a reversed version of the encoding algorithm performed in the server and described herein above. Decoding is done at the client computer during the progressive rendering operation as described at step 1705 of FIG. 17.

The decoding algorithm is explained herein using the simple case of an image with one component (such as a grayscale image). This is done for clarity of discussion, in the same fashion in which the encoding algorithm is explained herein above. The generalization to images of more components in straightforward. Input parameters to the algorithm are listed in Table 3 below:

Decoding Algorithm Initialization
1. Assign the value zero to each coefficient Coef(x,y,z).
2. Assign the value zero to each bit belonging to the HalfBit matrix.
3. Initialize all the coefficients as members of their corresponding Type16 group.
4. Initialize the list of significant coefficients to be empty.
5. If the data block (t_x,t_y,t_z,t_resolution,maxBitPlane (t_resolution)) is available at the client, read the value of maxBitPlane (tile), which in an embodiment of the invention is the first byte.

Figure 14:
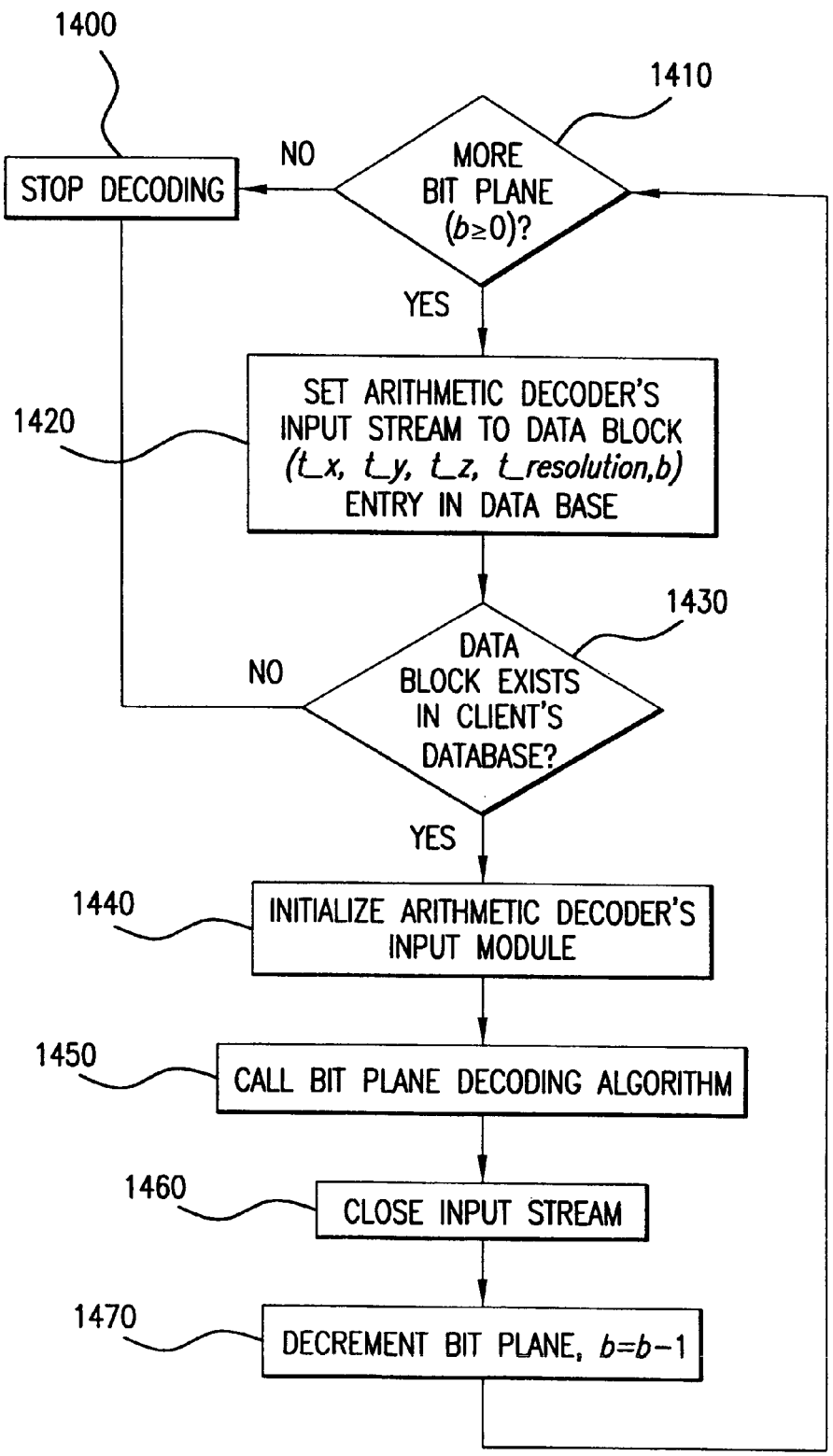
FIG. 14 is a flowchart illustrating a client decoding algorithm outer loop.

The outer loop of the decoding algorithm is now described with reference to FIG. 14. The decoding algorithm scans the bit planes from the given b=maxBitPlane(tile) to b=0 (step 1410). The input to each such bit plane scan is encoded data block (t_x,t_y,t_z, t_resolution,b) . Since the first stage of the decoding algorithm is arithmetic decoding, at the beginning of each scan, the input module of the arithmetic decoder is redirected (step 1420) to read from the "slot" in the database allocated for the particular data block. There are cases where although a subband tile participates in the rendering of the ROI, some of its data blocks will be missing. A data block could be missing due to the following reasons:
1. It was not requested for the current ROI since it is visually insignificant.
2. It was requested from the server, but has not arrived yet.

In any case, the tile's coefficients are required at some accuracy level for the rendering and the rule is obviously to use whatever data is present. At the first missing data block (step 1430), the outer loop is terminated. For example, if the first data block is missing, all of the coefficients retain their initial value of zero. If only the first few data blocks are present then only coefficients with "large" absolute value will be reconstructed and at a low precision. Once the bit plane scan is finished and the data block (t_x,t_y,t_z,t_resolution,b) has been decoded (step 1450), the input stream is closed (1460) and the bit plane is decremented. It should be mentioned that as during the encoding, the last two bit planes for the lossless applications are the "least significant bit plane" (b=1) and the "half bit plane" (b=0), as described in reference to FIG. 8.

Pseudo-code for the bit plane scan is provided in FIG. 15. The scan, for a given level b, decodes all of the coefficients' data corresponding to the absolute value interval $[\epsilon 2^b, \epsilon 2^{b+1})$ where $\epsilon = \epsilon_c$ for lossy applications and $\epsilon = 2^{-1}$ for lossless ones (as described in reference to FIG. 3 and FIG. 8).

The goal of the significance scan is to decode the locations of the coefficients that are "exposed" when the decoder traverses down to the current bit plane. Since the scan is a reversed reflection of the encoding scan as described herein above in reference to Table 2, the description below is brief.

TABLE 3

| Variable | Meaning |
| --- | --- |
| coef | Empty 3D matrix of subband coefficients to be filled by the decoding algorithm. |
| EqualBinSize | True for high or lossless quality. False for low quality (transmitted from the server). |
| $\epsilon_c$ | The minimal threshold for the component (transmitted from the server). |
| HalfBit | 3D matrix of bits containing (tileLength/2) × (tileLength/2) × tileHeight bits for HHX-Subbands type decomposition or tileLength × tileLength × (tileHeight/2) bits for XXH-Subbands type. |

Figure 28A:
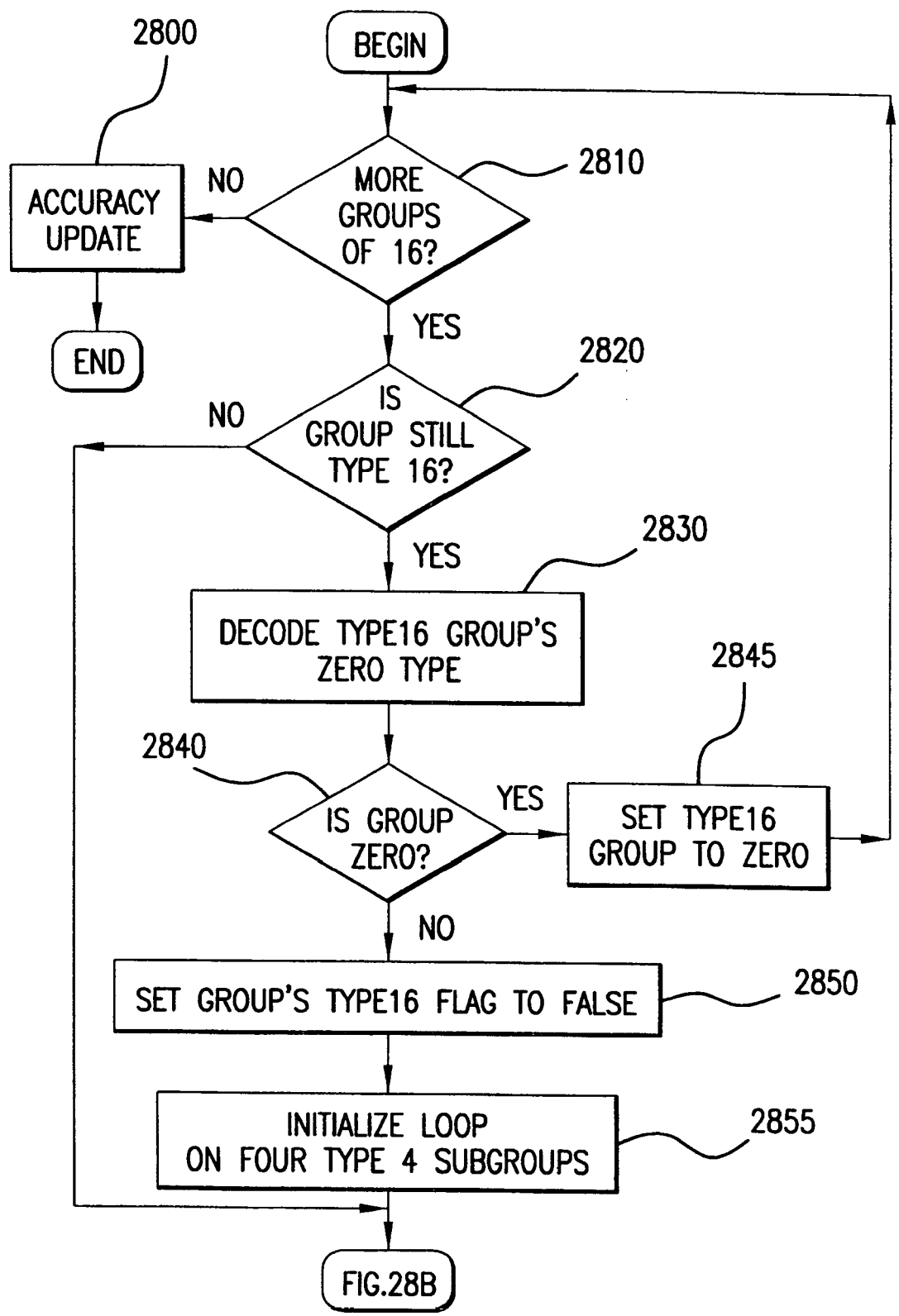
FIG. 28A is a flowchart illustrating the bit plane significance scan client decoding algorithm.
Figure 28B:
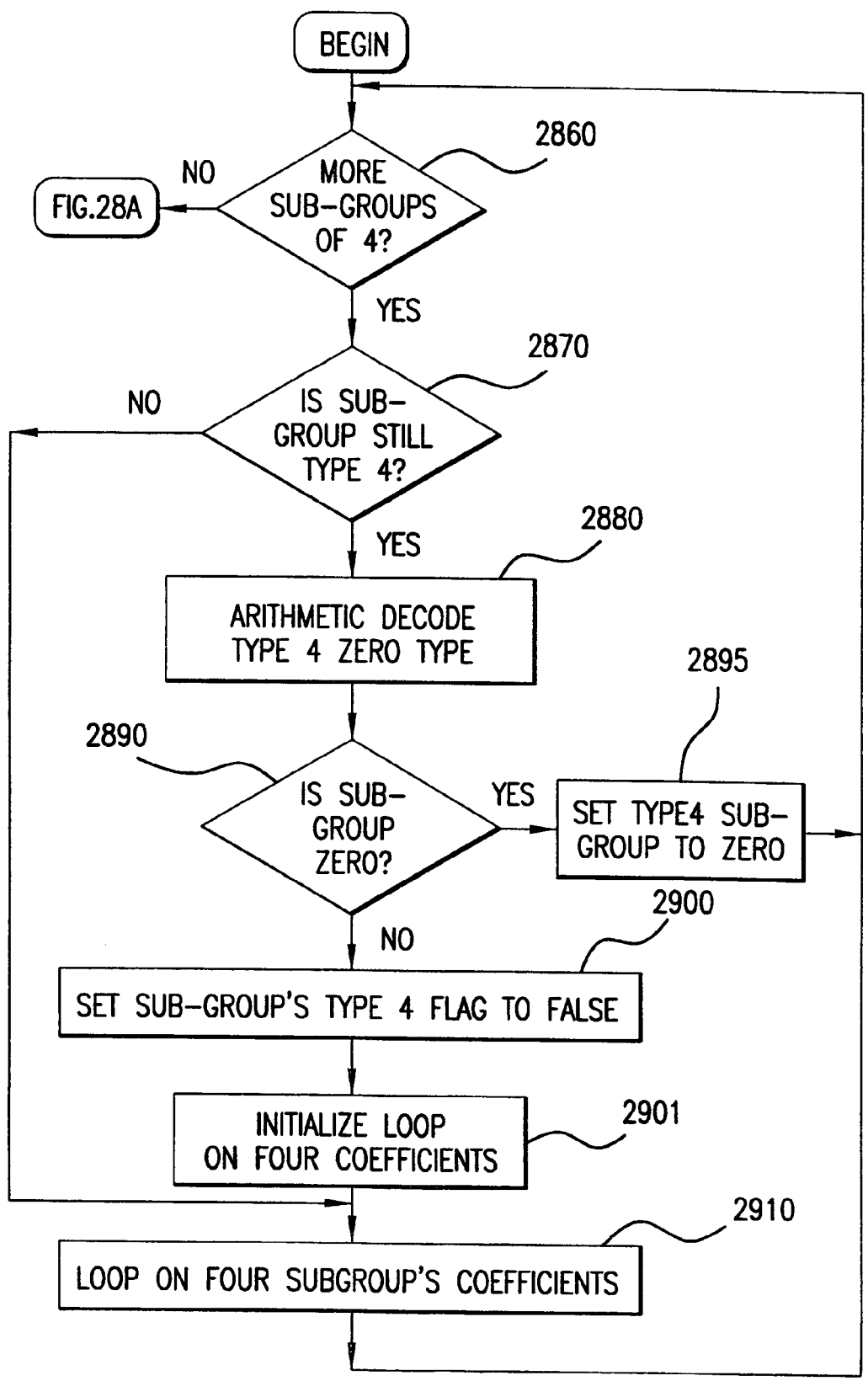
FIG. 28B is a flowchart illustrating the bit plane significance scan client decoding algorithm.

Reference is made to FIG. 28A and FIG. 28B, which reflect corresponding FIG. 10A and FIG. 10B.

Reference is first made to FIG. 28A. The first loop is on groups of Type16. If there are no more such groups (step 2810) the significance scan is terminated and decoding proceeds to the accuracy update (step 2800). If the current group is still labeled Type16 (2820) decoding is performed of the Boolean value b_Group<b (2830). If b_Group<b (2840), then the group is currently insignificant and decoding proceeds to the next group (2845). Else, the decoder removes the label Type16 (step 2850) and splits the Type16 group to 4 subgroups of Type4. If the group of 16 was not labeled Type16 then it must have been split at a higher bit plane. In both cases decoding must now continue to process the four subgroups of four coefficients. The decoder uses the same probability models as the encoder for the purpose of arithmetic decoding.

Reference is now made to FIG. 28B. Decoding iterates (step 2860) over the subgroups of four coefficients. If a subgroup is labeled 4 Type arithmetic decoding of the value of the test b_Subgroup<b is done (step 2880). The arithmetic decoding step is not performed if the following three conditions hold true:

1. The current group of Type4 is the fourth subgroup.
2. The previous three subgroups are still labeled Type4.
3. The four subgroups were created "just now" at the current scan by splitting a Type16 group.

In such a case, the group is certainly significant, it was not encoded and therefore does not need to be decoded. If the current subgroup remains insignificant, then decoding proceeds to the next subgroup. Else, the decoder removes the label Type4, splits the subgroup to the single coefficients and labels each of them Type1. If the subgroup was not labeled Type4 then it must have been split at a higher bit plane. In both cases the decoder must now continue handling each individual coefficient.

Decoding loops over the four coefficients. If a coefficient coef(x,y,z) is still labeled Type1 the decoder arithmetically decodes the value of the test b(x,y,z)<b. It does not perform the arithmetic decoding step if the following three conditions hold:

1. The current coefficient is the fourth coefficient.
2. The previous three coefficients are still labeled Type1.
3. The subgroup of the four coefficients was split "just now" at the current scan.

In such a case the coefficient is surely significant, so there is no need to decode the significance of the coefficient.

If the current coefficient remains insignificant, decoding then proceeds to the next coefficient. Else, it arithmetically decodes the sign of the coefficient, removes the label Type1 and adds the coefficient to the list of significant coefficients. At this stage the current approximated value coef(x,y,z) at the decoder is $$\text{sign}(coef(x, y, z)) \times \varepsilon \times \frac{3 \times 2^b}{2}$$

which corresponds to the middle of the bit plane interval $[\varepsilon 2^b, \varepsilon 2^{b+1})$.

At the bit plane b the significant coefficient list contains all the coefficients coef(x,y,z) for which b(x,y,z).gtoreq.b at an approximated value. The encoder provides this list in step 1000 in FIG. 10A, and the decoder handles it in step 2800 in FIG. 28A. When performing this operation, and for each coefficient in the list, the decoder arithmetically decodes the value of test coef(x,y,z)<coef(x,y,z), where coef(x,y,z) is the actual value of the coefficient (not known to the decoder). It then updates the approximated value accordingly by adding/subtracting from coef(x,y,z) the amount $$\varepsilon \times \frac{2^b}{4}.$$

Pseudo-code for the least significant bit plane scan and half bit plane scan are given in FIG. 16A and FIG. 16B. The decoder scans all the coefficients from all subbands at step 1610. Decoding of those of the subbands that are skipped by the encoding algorithm is not performed, but their least significant bit is counted as zero instead. The order of the scan in FIG. 16B reflects the order of the encoding scan in FIG. 12B.

Figure 17:
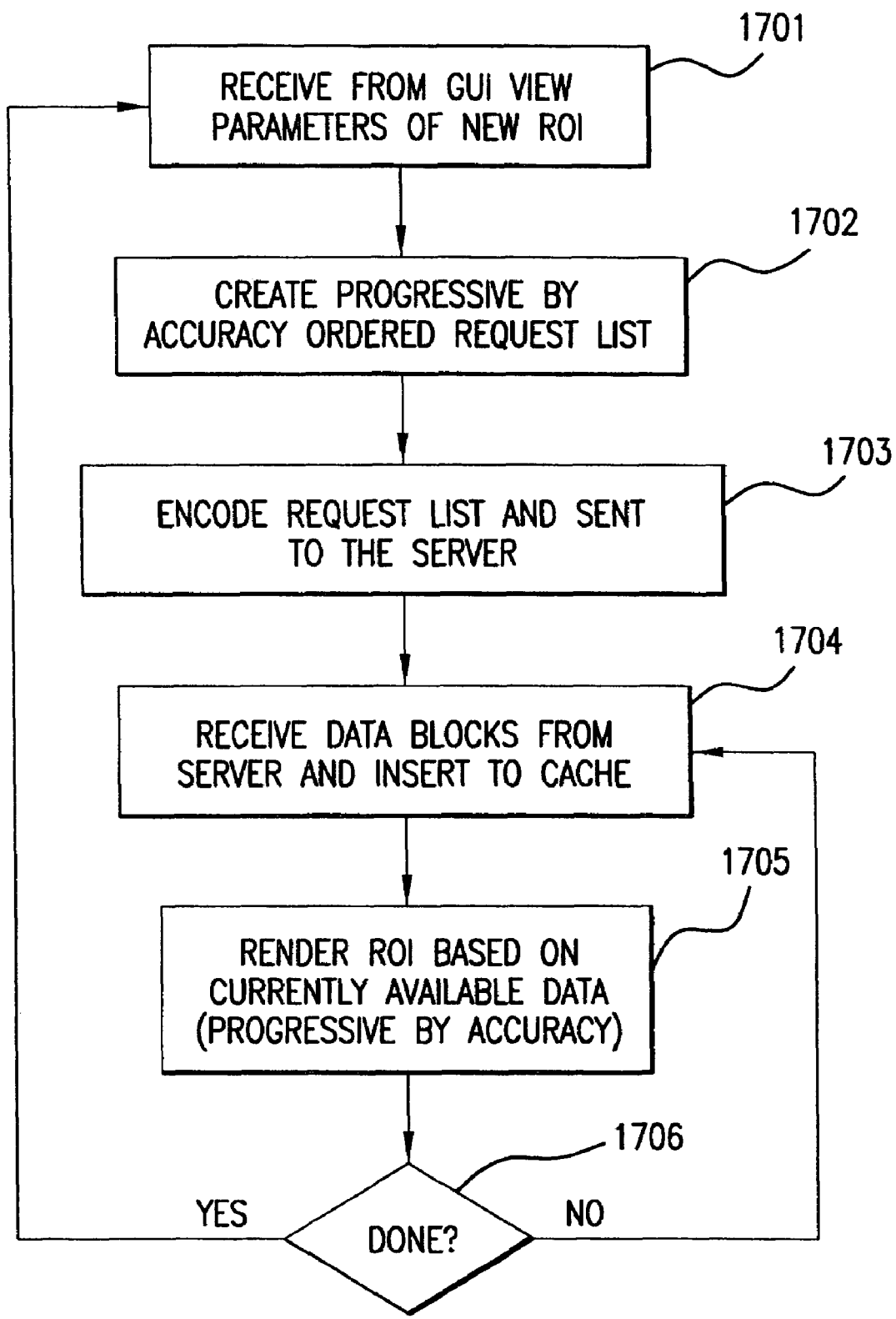
FIG. 17 is a flowchart illustrating client "progressive by accuracy" workflow.

Reference is now made to FIG. 17 for the description of the workflow at the client computer 110. Any new ROI generated by the user's action such as a zoom-in or a scroll, invokes at step 1701 a call from the GUI interface to the client imaging module with the new ROI view parameters. The client imaging module then computes in step 1702 which data blocks (described herein above in reference to FIG. 3) are required for the rendering of the ROI and checks if these data blocks are available in the client cache. If not, their coordinate (given by Eq. 2) is added to a request list ordered according to some progressive mode. The request list is then encoded in step 1703 and sent to the server. The server responds to the request by sending back to the client a stream of data blocks, in the order in which they were requested. In step 1704 the client inserts them to their appropriate location in the distributed database. At various moments (step 1705), the rendering of the ROI, is invoked. Naturally, the rendering operation is progressive and is able to use only the currently available data in the client's database.

The imaging module on the client computer 110 receives view parameters listed in Table 4 from the GUI interface module. These parameters are used in step 1702 to generate a request list for the ROI. The same parameters are used to render the ROI in step 1705.

TABLE 4

| Variable | Meaning |
| --- | --- |
| worldPolygon | A 2-D polygon in the original image coordinate system - defines which portion of each slice of the sequence will be rendered |
| sliceRange | An interval [firstSlice,lastSlice) that defines which slices will be rendered |

TABLE 4-continued

| Variable | Meaning |
| --- | --- |
| scale | The view resolution. 0 < scale < 1 implies a low view resolution, scale = 1 original resolution and scale > 1 a "higher than original" view resolution |
| deviceDepth | A number in the set {8,16,24} representing the depth of the output device |
| viewQuality | A quality factor in the range [1, 7] where 1 implies very low quality and 7 implies lossless quality |
| luminanceMap | If active: a curve defining a mapping of medical images with more than 8 bits (typically 10,12,16 bits) per grayscale values to an 8 bit screen |
| progressiveMode | One of: Progressive By Accuracy, Progressive By Resolution, Progressive by Spatial Order |

The basic parameters of a ROI are worldPolygon, sliceRange and scale, which determine uniquely the ROI view. If the ROI is to be rendered onto a viewing device with limited resolution, then a sliceRange, containing a large number of slices of the 3-D image, will be coupled by a small scale. The other view parameters determine the way in which the view will be rendered. The parameters deviceDepth and viewQuality determine the quality of the rendering operation. In cases the viewing device is of low resolution or the user sets the quality parameter to a lower quality, the transfer size can be reduced significantly, as described herein below in reference to step 1702.

The parameter luminanceMap is typically used in medical imaging for grayscale images that are of higher resolution than the viewing device. Typically, screens display grayscale images using 8 bits, while medical images sometimes represent each pixel using 16 bits. Thus, it is necessary to map the bigger pixel range to the smaller range of [0, 255].

Lastly, the parameter progressiveMode determines the order in which data blocks should be transmitted from the server computer 120. The "Progressive By Accuracy" mode is the preferred mode for viewing in low bandwidth environments. "Progressive By Resolution" mode is easier to implement since it does not require the more sophisticated accuracy (bit plane) management and therefore is commonly found in previous solutions. The superiority of the "progressive by accuracy" mode can be proven mathematically by showing the superiority of non-linear approximation over linear approximation for the class of real-life images. The "Progressive by Spatial Order" mode is preferred for a cine view of the sequence of 2-D slices one after the other. In this mode the image data is ordered and received from the first slice to the last one, such that rendering can be done in parallel the transmission.

Figure 18:
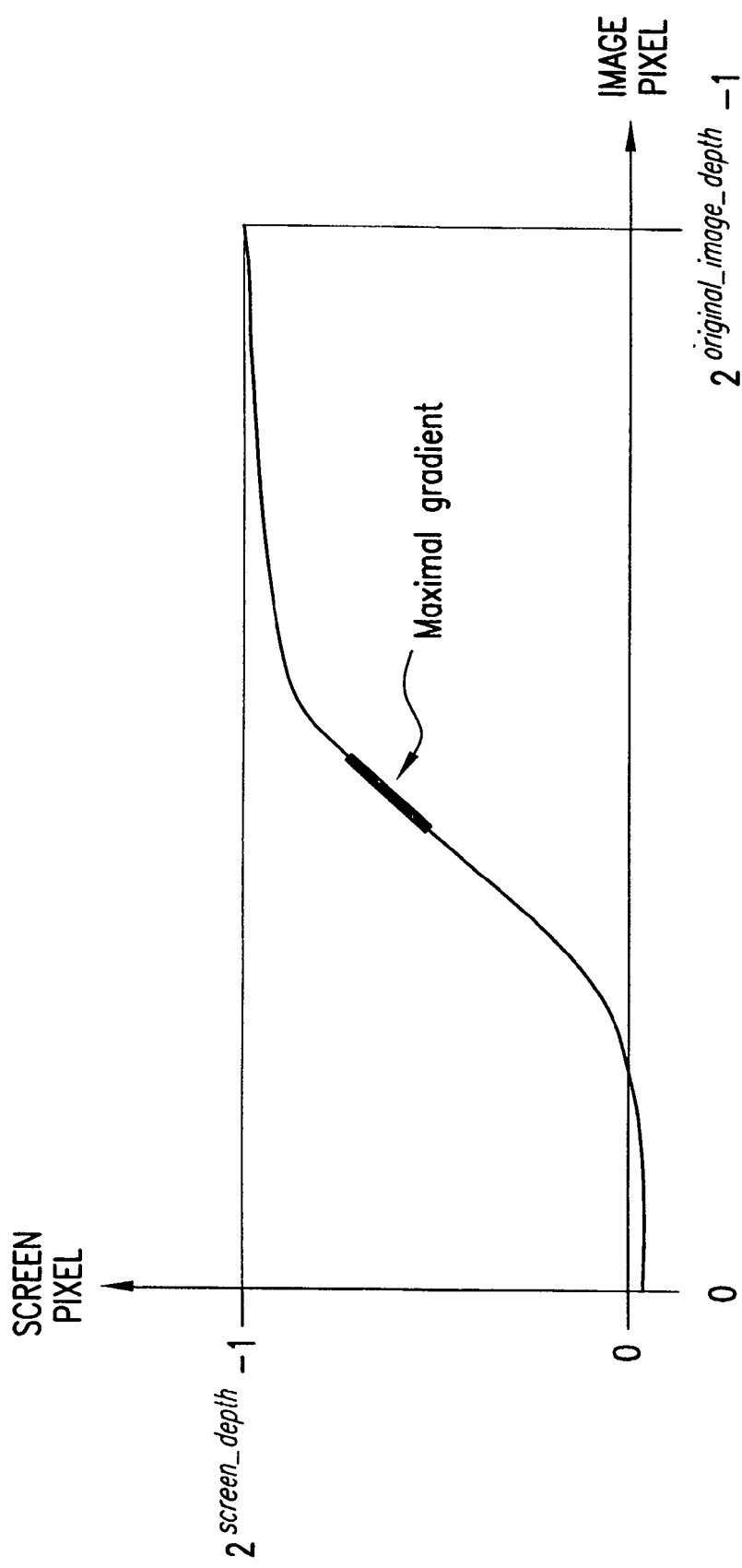
FIG. 18 illustrates a curve defining the mapping from Original_Image_Depth-bit image to Screen_Depth-bit.

Reference is now made to FIG. 18 for the description of luminance mapping. A mapping from original image depth (e.g., 10,12,16 bits) to screen depth (typically 8-bits), is defined by a monotonic function as in Eq. 8

$$f:[0, 2^{original\_image\_depth}-1] \to [0, 2^{screen\_depth}-1]. \quad \text{(Eq. 8)}$$

The curve influences not only the mapping, i.e. the drawing to the screen, but also the request from the server. To understand that, let us concentrate in the maximal gradient of the curve in FIG. 18. In a lossy mode, the request is created such that the image approximation in the client side is close enough to the original image, i.e., the RMS (Root Mean Square error) is visually negligible. When a curve (mapping function) is applied, the RMS can be increased or reduced. The maximal RMS increasing factor depends on the maximal derivative of the curve as in Eq. 9.

$$\text{RMS\_increasing\_factor} = \frac{RMS(f(I), f(\hat{I}))}{RMS(I, \hat{I})} \le \max(f'), \quad \text{(Eq. 9)}$$

where

I is the original image, $\hat{I}$ is the approximated image, $f$ is the mapping function, $$RMS(I_1, I_2) = \frac{\|I_1 - I_2\|_{L_2}}{\text{Image\_size}},$$

max ($f'$) is the maximal derivative of the curve.

Instead of calculating Eq. 9, image quality will be assured by using the worst case of the RMS increasing factor that is given by the following Eq. 10.

RMS_increasing_factor=Maximal_derivative=max($f'$) (Eq. 10)

If the RMS increasing factor is greater than 1, it means that the "new RMS" may be greater than a visually negligible error. Thus, the request list should be increased (i.e. more bitplanes should be requested from the server) in order to improve the approximation accuracy. Conversely, if the RMS increasing factor is smaller than 1, the request list can be reduced. The exact specification of this is provided in the following description.

In step 1702, using the ROI view parameters, the client imaging module calculates a data block request list ordered according to the progressiveMode. Given the parameters worldPolygon, sliceRange and scale it is possible to determine which subband tiles (such as defined in Eq. 1) in the frequency domain participate in the reconstruction of the ROI in the image domain. These tiles contain all the coefficients required for an Inverse Subband/Wavelet Transform (IWT) step that produces the ROI. The parameter dyadicResolution(ROI), which is the lowest possible dyadic resolution higher than the resolution of the ROI, is first calculated. Any subband tiles of a higher resolution than dyadicResolution(ROI) do not participate in the rendering operation. Their associated data blocks are therefore not requested, since they are visually insignificant for the rendering of the ROI. If scale≧1 then the highest resolution subband tiles are required. If scale≦$2^{1-thumbnailResolution}$ (as described in reference to FIG. 4) then only the lowest resolution tile is required. Mapping is performed for any other value of scale according to Table 5. Table 5 describes the mapping from a given scale to dyadic subband resolution.

TABLE 5

| Scale | Highest Subband Resolution |
|---|---|
| scale $\leq 2^{1-\text{thumbnailResolution}}$ | 1 |
| $2^{1-\text{thumbnailResolution}} <$ scale $\leq 1$ | numberOfResolutons $- \lfloor -\log_2 (\text{scale}) \rfloor$ |
| scale $> 1$ | NumberOfResolutions |

Figure 19:
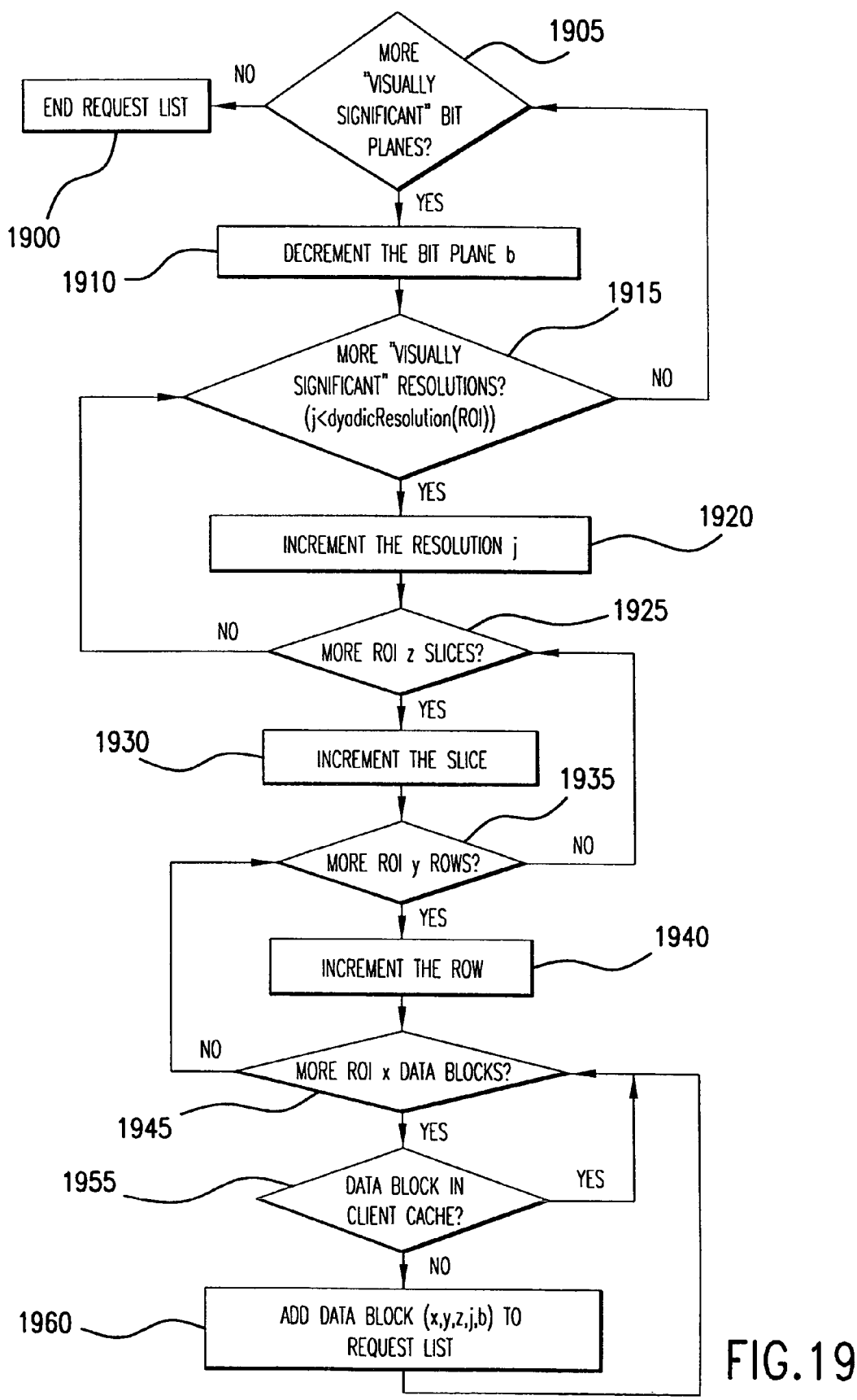
FIG. 19 is a flowchart illustrating the composition of a "Progressive by accuracy" request list for a ROI according to an embodiment of the invention.

Once it is determined which subband tiles participate in the rendering of the ROI computation proceeds with finding which of their data blocks are visually significant and in what order they should be requested. Using well known rate/distortion rules from the field of image coding, it is possible to determine the preferred order in which the data blocks should be ordered by the client imaging module (and thus delivered by the server). An ordering scheme referred to herein as "Progressive By Accuracy" mode is described in FIG. 19. The mathematical principals of non-linear approximation underlie this approach. The subband coefficients with largest absolute values are requested first since they represent the most visually significant data such as strong edges in the image. Notice that high resolution coefficients with large absolute value are requested before low resolution coefficients with smaller absolute value. Within each given layer of precision (bit plane) (step 1910) where the order of the request is in accordance with the resolution (step 1920), whereby low resolution coefficients are requested first and the coefficients of highest-Sub-band-Resolution are requested last.

A major difficulty in executing this step is now discussed. Assume a subband tile such as described by Eq. 1 is required for the rendering of the ROI. This means that t_resolution≦dyadicResolution (ROI) and the tile is required in the IWT procedure that reconstructs the ROI. There is a need to understand which of the data blocks such as described by Eq. 2 associated with the subband tile represent visually insignificant data and thus should not be requested. Sending all of the associated data blocks will not affect the quality of the progressive rendering. However, in many cases transmitting the last data blocks associated with high precision is unnecessary since the last blocks will be visually insignificant. In such a case, the user will notice that the transmission of the ROI from the server is still in progress, yet the progressive rendering of the ROI seems to no longer change the displayed image.

This difficulty is further explained by the following examples:

In the first example, let us assume that the ROI is a low resolution rendering of the full image at the resolution n. Thus, all the subband coefficients at the subband resolutions $1 \leq j \leq n$ participate in the IWT of the ROI. However, only the very large coefficients of these sub-bands are visually significant for a rendering of this ROI, even at very high qualities. Also these large coefficients are only required at a very low precision. Thus, it is advisable to request from the server only the first few data blocks associated with each subband tile at resolutions ≦n since they correspond to the highest bit planes.

In the second example, let us assume that the ROI is at the highest resolution of the image. Usually this would mean that for any subband tile participating in the reconstruction of the ROI all of the associated data blocks should be requested, such that the rendering will be of a very high (or even lossless) quality. But if the parameter deviceDepth listed in Table 4 is set at low resolution (indicating that the viewing device is of low resolution) or the parameter viewQuality is set at low quality (indicating that the user is currently not interested in high quality rendering), the last data blocks of each subband tile corresponding to high precision need not be ordered.

A method to determine which of the first data blocks are required is as follows. First, for each subband tile (t_x, t_y,t_z,t_resolution) participating in the reconstruction of the ROI, initialize the set of requested data blocks to the "maximal" set (t_x,t_y,t_z,t_resolution,t_bitPlane)

minRequestPlane≦t_bitPlane≦maxBitPlane(t_resolution)

with minRequestPlane=0. Recall that at this point the client does not know the amount of data that each absent data block contains. In many cases requested data blocks will turn out to be empty. Second, remove from the data set all the data blocks (t_x,t_y,t_z,t_resolution,t_bitPlane)

such that t_bitPlane≦numberOfResolution−dyadicResolution(ROI). That is one data block/bit plane for each lower resolution.

Third, update minRequestPlane accordingly. This rule, that the lower the resolution the less precision is required, originates from the way subband coefficients are scaled according to their resolution. Fourth, whenever deviceDepth=8, the output device is of low resolution. In this case the client requests less precision. Decrement one bit plane and set minRequestPlane=min(maxBitPlane(t_resolution), minRequestPlane+1).

Fifth, if viewQuality is set at a lower viewing quality, further remove high precision data blocks from the set. Again, the rule is a removal of one bit plane per lower quality.

Last, and according to the description hereinabove with reference to FIG. 18, additionally reduce or add the number $$\left\lfloor \log_2\left(\frac{1}{\text{Maximal\_derivative}}\right) \right\rfloor$$

of bit planes from the request list.

This last step in the process is further explained via the following examples.

In the first example there is given an image depth of 12 bits a screen depth of 8 bits and a linear luminance mapping, calculate $$\text{Maximal\_derivative} = \frac{2^8}{2^{12}} = 2^{-4}$$

and so the number of additionally reduced from the request list bit planes becomes $$\left\lfloor \log_2\left(\frac{1}{\text{Maximal\_derivative}}\right)\right\rfloor = \left\lfloor \log_2\left(\frac{1}{2^{-4}}\right)\right\rfloor = 4$$

In the second example there is given a luminance mapping with Maximal_derivative=2, the number of bit planes reduced from the request list is:

$$\left\lfloor \log_2\left(\frac{1}{\text{Maximal\_derivative}}\right)\right\rfloor = \left\lfloor \log_2\left(\frac{1}{2}\right)\right\rfloor = -1$$

Thus one bit plane is added to the original set.

In step 1703 in FIG. 17, the client imaging module encodes the request list into a request stream which is sent to the server computer 120 via the media 130 (see FIG. 1). The request list encoding algorithm is a "cube based" procedure. The heuristics of the algorithm is that the requested data block usually can be grouped into data block "cubes". From the request list of data blocks indexed as in Eq. 2 the encoding algorithm computes structures of the type presented in Eq. 11.

$$\text{struct} = \{(t\_x, t\_y, t\_z, t\_\text{resolution}, t\_\text{bitPlane}), n_x, n_y, n_z\}, n_x, n_y, n_z \geq 1 \quad \text{(Eq. 11)}$$

Each such structure represents the $n_x \times n_y \times n_z$ data blocks $$\{(t\_x+i, t\_y+j, t\_z+k, t\_\text{resolution}, t\_\text{bitPlane})\},$$
$$0 \leq i < n_x, 0 \leq j < n_y, 0 \leq k < n_z$$

The encoding algorithm attempts to create the shortest possible list of structures of the type defined by Eq. 11, which can be done by collecting the data blocks to the largest possible cubes. It is important to note that the algorithm ensures the order of data blocks in the request list is not changed, since the server will respond to the request stream by transmitting data blocks in the order in which they were requested. This is particularly preferable when a user switches to another subsequent group of 3-D image slices that has not been viewed before. In such a case the request list might be composed of hundreds of requested data blocks, but they will be collected to one (x,y,z) cube as defined by Eq. 11 for each pair (t_resolution,t_bitPlane).

In step 1704 in FIG. 17 the client computer 110, upon receiving from the server an encoded stream containing data blocks, decodes the stream and inserts the data blocks into their appropriate location in the distributed database using their ID as a key. The decoding algorithm performed in this event is a reversed step of the encoding process described in reference to step 1703. Since the client computer 110 is aware of the order of the data blocks in the encoded stream, only the size of each data block need be reported along with the actual data. In case that the server informs of an empty data block, the receiving module marks the appropriate slot in the database as existing but empty.

Recall that the first four of the five coordinates of a data block (t_x,t_y,t_z,t_resolution,t_bitPlane) denote the subband tile, associated with each data block. From the subband tile coordinates the dimensions of the "area of visual significance" is calculated. That is, the portion of the ROI that is affected by the subband tile.

Assuming that each subband tile is of size tileLength× tileLength×tileHeight and that the wavelet basis used has a maximal filter size maxFilterSizeXY in X and Y directions and maxFilterSizeZ in Z direction, then defining hFilterSize=⌈maxFilterSize/2⌉ and factorXY and factorZ–numbers of HHX-Subbands and XXH-Subbands type decompositions respectively that were performed on the 3-D image from the resolution t_resolution till the lowest resolution, we have that the dimensions of the affected region of the ROI (in the original image's coordinate system) are $$[t\_x \times tileLength^{factorXY} - hFilterSizeXY^{factorXY},$$
$$(t\_x+1) \times tileLength^{factorXY} +$$
$$hFilterSizeXY^{factorXY}] \times [t\_y \times tileLength^{factorXY} - hFilterSizeXY^{factorXY},$$
$$(t\_y+1) \times tileLength^{factorXY} +$$
$$hFilterSizeXY^{factorXY}] \times [t\_z \times tileHeight^{factorZ} - hFilterSizeZ^{factorZ},$$
$$(t\_z+1) \times tileHeight^{factorZ} + hFilterSizeZ^{factorZ}]$$

These dimensions are merged into the next rendering operation's region. The rendering region is used to efficiently render only the "updated" portion of the ROI.

Discussion now continues with the description of step 1705 in FIG. 17, the step of progressive rendering. During the transmission of ROI data from the server to the client, the client performs rendering operations of the ROI. To ensure that these rendering tasks do not interrupt the transfer, the client runs two program threads: communications and rendering. The rendering thread runs in the background and draws into a pre-allocated "off-screen" buffer. Only then does the client use device and system dependant tools to output the visual information from the "off-screen" to the rendering device such as the screen or printer.

The rendering algorithm performs reconstruction of the ROI at the highest possible quality based on the available data at the client. That is data that were previously cached or data that recently arrived from the server. For efficiency, the progressive rendering is performed only for the portion of the ROI that is affected by newly arrived data. Specifically, data that arrived after the previous rendering task began. This updated region is obtained using the method of step 1704 described herein above.

The parameters of the rendering algorithm are composed of two sets as follows. The first set comprises ROI parameters as listed in Table 4 herein above. The second set comprises parameters transmitted from the server as listed in Table 6 herein below, with the exception of one parameter, the jumpSize parameter, which is a parameter particular to the server.

The rendering algorithm computes pixels at the dyadic resolution dyadicResolution(ROI). Recall that this is the lowest possible dyadic resolution, which is higher than the resolution of the ROI. The obtained image is then resized to the correct resolution and mapped to the depth of output device.

Discussion of the rendering rate now follows. As ROI data is transmitted to the client, the rendering algorithm is performed at certain time intervals of a few seconds. At each point in time, only one rendering task is performed for any given displayed image. To ensure that progressive rendering does not become a bottleneck, two rates are measured: the data block transfer rate and the ROI rendering speed. If it is predicted that the transfer will be finished before a rendering task, a small delay is inserted, such that rendering will be performed after all the data arrives. Therefore, in a slow network scenario (as the Internet often is), for almost the entire progressive rendering tasks, no delay is inserted. With the arrival of every few kilobytes of data, containing the information of a few data blocks, a rendering task visualizes the ROI at the best possible quality. In such a case the user is aware that the bottleneck of the ROI rendering is the slow network and has the option to accept the current rendering as a good enough approximation of the image and not wait for all the data to arrive.

The following is a discussion of the memory requirements of a subband data structure, and of the allocation and initialization of this memory in reference to FIG. 20. This data-structure is required to efficiently store subband coefficients, in memory, during the rendering algorithm. This is required since the coefficients are represented in long integer (lossless coding mode) or floating-point (lossy coding mode) precision, which typically require more memory than a pixel representation (1 or 2 bytes). In a lossy mode the coefficients at the client side are represented using floating-point representation, even if they were computed at the server side using an integer implementation to minimize round-off errors.

The rendering algorithm begins with initializing coefficient and pixel memory 3-D matrices. Let us denote by dyadicWidth(ROI) the width of the XY projection of the ROI onto the resolution dyadicResolution(ROI) and height (ROI) the number of slices in the ROI. For each component two 3-D matrices of coefficients are allocated with dimensions dyadicWidth(ROI)×dyadicWidth(ROI)×height(ROI)

For a lossless case two additional matrices with dimensions sliceWidth×sliceWidth×tileHeight are allocated for half bit planes of XY and Z transforms as described herein above in reference to FIG. 8. The size of these allocations is limited by the resolution of the output device and not by the original 3-D data, leading to the memory-constrained data structure.

Beginning with the lowest resolution of 1, the algorithm executes a multi-resolution march from the first to the last tile of the ROI in the Z direction. The pseudo-code for this recursive march is presented in FIG. 20. First the allocated matrix is filled with sub-tiles of coefficients calculated on the lower resolution, yielding low pass subbands of the current resolution. Then the matrix is complemented by the high pass subbands (wavelet) coefficients, decoded from the database or read from the memory cache as described hereinbelow in reference to FIG. 21. An inverse subband transform described hereinbelow in reference to FIG. 3 produces multiresolution pixels. Each time the highest resolution DyadicResolution(ROI) is reconstructed, it is supplied as input to the resizing and luminance mapping step.

Figure 21:
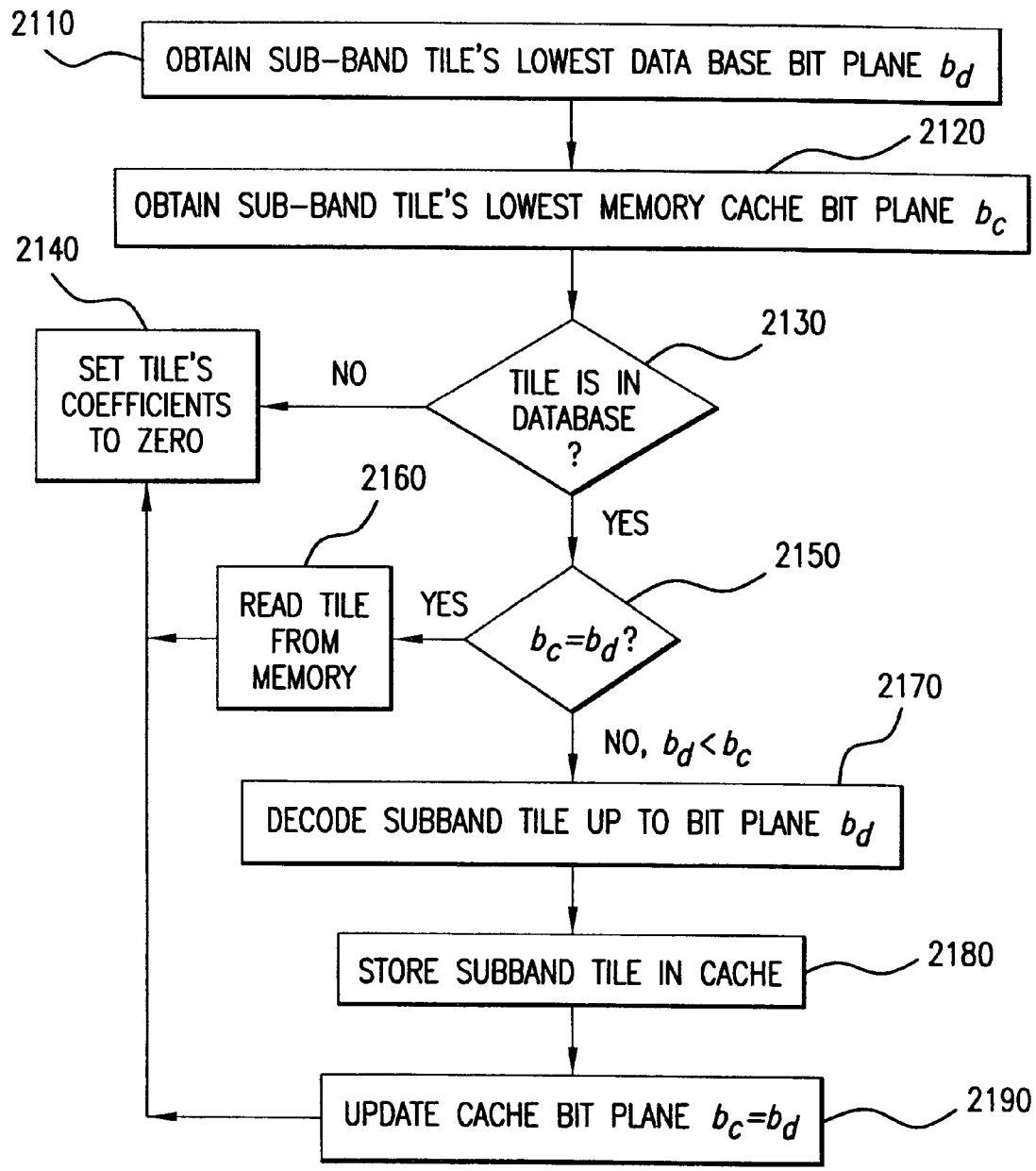
FIG. 21 is a flowchart illustrating the subband tile extraction function according to an embodiment of the present invention.

The subband coefficients data structure described in herein above in reference to FIG. 20 is filled on a tile basis. Each such subband tile is obtained either by decoding the corresponding data blocks stored in the database or by reading from the memory cache. The memory cache is used to store coefficients in a simple encoded format. The motivation for its use is as follows. The decoding algorithm described herein above in reference to Table 3 is computationally intensive and thus should be avoided whenever possible. To this end the rendering module uses a memory cache where subband coefficient are stored in a relatively simple encoded format, which decodes relatively fast. For each required subband tile the following extraction procedure is performed, as depicted in FIG. 21. If no data blocks are available in the database for the subband tile (step 2130), its coefficients are set to zero (step 2140). If the tile's memory cache storage is updated (step 2150), in other words if it stores coefficients in the same precision as in the database, then the coefficients can be efficiently read from there (step 2160). The last possibility is that the database holds the subband tile in higher precision. Then, the tile is decoded (step 2170) down to the lowest available bit plane using the decoding algorithm described herein above in reference to Table 3, and the cached representation is replaced (step 2180) with a representation of this higher precision information.

The inverse subband transform is an inverse step to step 2302 performed in the server as described herein below in reference to FIG. 23. Following FIG. 3, we see that eight combined tiles of total size

[nTileX(j)×tileLength,nTileY(j)×tileLength,tileHeight]

at the resolution j are transformed to a sequence of tileHeight frames at the next higher resolution using subbandTransformType(j). If j+1<dyadicResolution(ROI), the pixels obtained by this step are inserted into the corresponding place of allocated memory at the resolution j+1. If j+1=dyadicResolution(ROI), the pixels are processed by the next step of image resize and luminance mapping.

In case that the resolution of the ROI is not an exact dyadic resolution, the image obtained by the previous step must be re-sized to this resolution. This can be done using operating system imaging functionality. In most cases the operating system's implementation is sub-sampling which in many cases produces an aliasing effect, which is not visually pleasing. To provide higher visual quality, the imaging system uses the method of linear interpolation. The output of the interpolation is written to an "off-screen" buffer. From there it is displayed on the screen using system device dependant methods. When luminanceMap is active, mapping to 8-bit screen is performed using the mapping function described in reference to FIG. 18.

Figure 22:
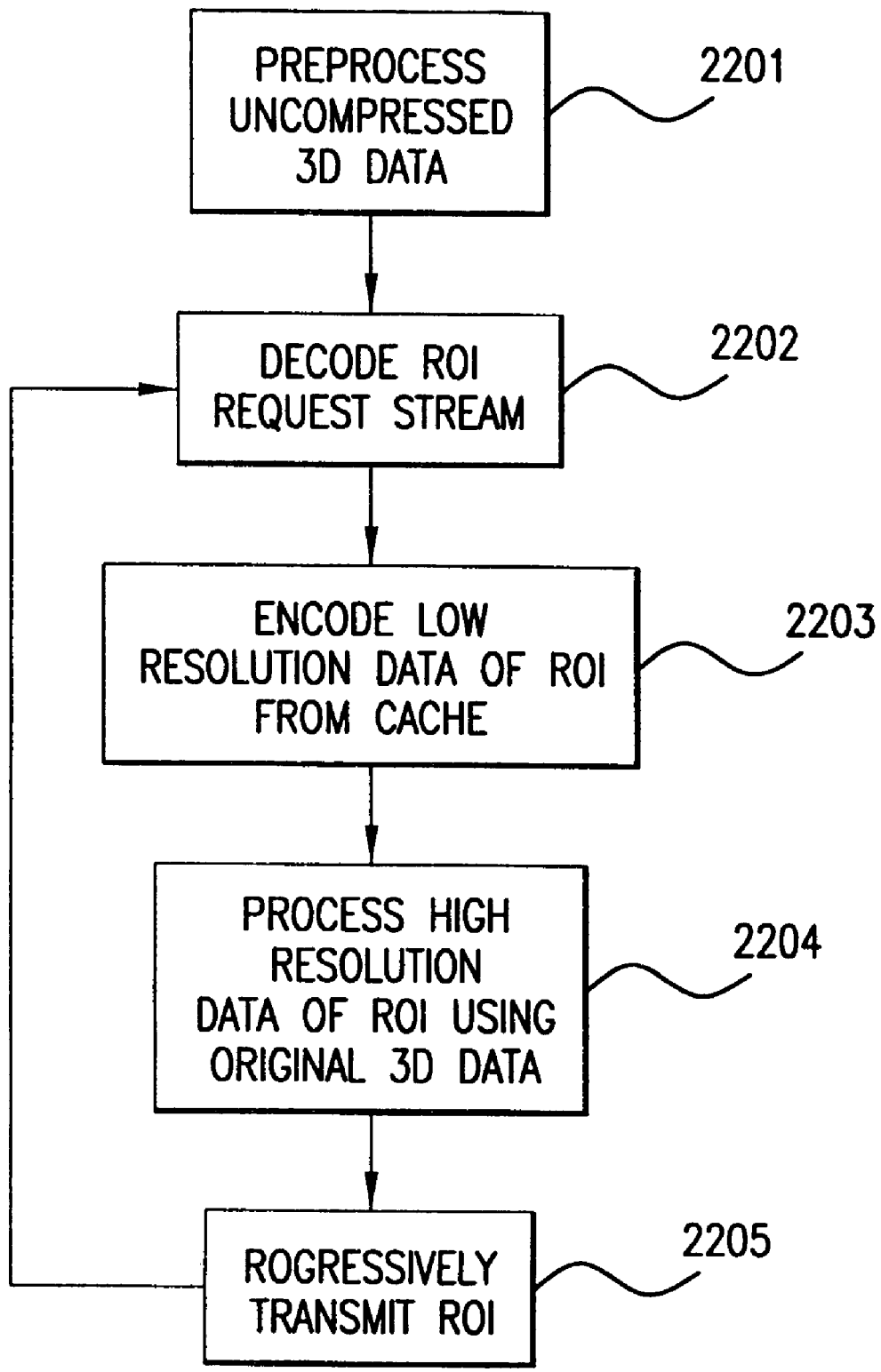
FIG. 22 is a flowchart illustrating the server workflow of the present invention.

The operation of the server computer 120 in FIG. 1 will now be described with reference to FIG. 22. Initially, an uncompressed digital 3-D image is stored in, for example, storage 122 of the server computer 120. This uncompressed digital 3-D image may be a sequence of two-dimensional images, stored with a selected resolution and depth. For example, in the medical field, each of these the uncompressed digital image may be contained in a DICOM file.

Once the client computer 110 requests to view or print a certain 3-D image, the server computer 120 performs pre-processing (step 2201). This step is a computation done on data read from the original digital 3-D image. The results of the computation are stored in the server cache device 121. After this fast computation a "ready to serve" message is sent from the server to the client containing basic information on the image.

In step 2202, the server receives an encoded stream of requests for data blocks associated with a ROI that needs to be rendered at the client. The server then decodes the request stream and extracts the request list.

In step 2203, the server reads from cache or encodes data blocks associated with low-resolution portions of the ROI, using the cached results of the preprocessing Step 2201.

If the ROI is a high-resolution portion of the image, the server (step 2204) either reads from cache or performs a local and efficient version of the preprocessing step 2201. Specifically, a local portion of the uncompressed 3-D image volume, associated with the ROI, is read from the storage 122, processed and encoded. In step 2205, the data that was encoded in step 2203 and step 2204 is progressively sent to the client in the order it was requested.

The preprocessing step 2201 is now described in further detail with reference to FIG. 23. The goal of the preprocessing algorithm is to provide the fastest response to the user's request to interact with the 3-D image. Once this fast computational step is performed, the server is able to provide efficient transmission of any client ROI requests that will follow. In most cases, regarding medical applications, the first ROI is a view of several 2-D slices of the 3-D image volume at low resolution (thumbnails). The preprocessing algorithm begins with a request for an uncompressed image that has not been processed before or that has been processed but the result of this previous computation has been deleted from the cache. As explained, this unique algorithm is preferable over the simpler procedure of encoding the full image into some progressive format. This latter technique provides a significantly slower response to the user's initial request then the technique described below provided by the present invention. At the end of the algorithm a "ready to serve ROI" message is sent to the client containing basic information on the 3-D image. While some of this information, 3-D image dimensions, original color space, resolution etc., is available to the user of the client computer, most of this information is "internal" and required by the client to formulate ROI request lists (step 1702) and progressively render (step 1705). A detailed description of the preprocessing algorithm now follows.

algorithm to use certain reversible wavelet transforms and may slow down the algorithm.

The subbandTransformType(j) parameters are used for the (dynamic) selection of wavelet basis that is crucial to the performance of the imaging system. The selection can be non-stationary, meaning a different transform for each resolution j. The selection is derived from the following considerations.

The first consideration is of coding performance (in a rate/distortion sense). This is obviously required from any subband/wavelet transform.

The second consideration is of an approximation of ideal low pass. It is preferred to choose a transform such that low resolutions of the image will be of high visual quality. Some filters produce poor quality low resolutions even before any compression takes place.

The third consideration is of fast transform implementation. The associated fast transform must be implemented using fast operations such as lifting steps, or integer shifts and additions, etc. Some good examples are the Haar and CDF transforms (1,3), (2,2).

The fourth consideration is of fast low pass implementation. This is a very important parameter, since together with the parameter named jumpSize herein, it determines almost all of the complexity of the algorithm. For example, the CDF (1,3) is in this respect the "optimal" transform with three vanishing moments. Since the dual scaling function is the simple B-spline of order 1, its low pass is simple averaging. Thus, the sequence of CDF transforms, using the B-spline of

TABLE 6

Preprocessing Parameters

| Variable | Meaning |
| --- | --- |
| LosslessMode | If true, preprocessing will prepare data that can be used for lossless transmission. |
| SubbandTransform Type(j) | The framework allows to select a different subband transform for each resolution of the 3D image. The technical term is: non-stationary transforms. |
| Decomposition Type(j) | The type of decomposition (HHX-Subbands, XHH-Subbands, or All-Subbands, see §4) that was used on the resolution number j. |
| NumberOfResolutions | The number of resolutions in the Multiresolution structure calculated for the image. |
| JumpSize | A number in the range [0, numberOfResolutions - 1]. The preprocessing stage computes only the top lower part of the image's multiresolution pyramid of the size numberOfResolutions −jumpSize. |
| TileLength | Size of 3D tile in x and y direction. Typically = 64 as tradeoff between time and coding performance. |
| TileHeight | Size of 3D tile in z direction. Typically = 2 for the better time performance. |
| NTilesX(j) | Number of subband tiles in the x direction at the resolution j |
| NTilesY(j) | Number of subband tiles in the y direction at the resolution j |
| NTilesZ(j) | Number of subband tiles in the z direction at the resolution j |
| Threshold(j) | A matrix of values used in lossy compression. The subband coefficients at the resolution j with absolute value below threshold(j) are considered as (visually) insignificant and set to zero. |

Given an input image, the parameters described in Table 6 above are either computed or chosen. These parameters are also written into a header sent to the client and are used during the progressive rendering step 1705. The most important parameters to select are the following:

The losslessMode is a mode in which progressive transmission of images takes place until lossless quality is obtained. Choosing this mode requires the preprocessing order 1 as the dual scaling function, but with wavelets with increasing number of vanishing moments are in some sense "optimal" in our system. They provide a framework for both real time response and good coding efficiency.

The fifth consideration is the existence of a lossless mode. If the losslessMode parameter is true, filters must belong to a subclass of reversible transforms.

The sixth consideration is of low system I/O. If the network 157 depicted in FIG. 1 connecting between the image residing on the storage 122 and the imaging server 120 is slow, the bottleneck of the preprocessing stage (and the whole imaging system for that fact) might be simply the reading of the original image. In such a case we may choose a transform with a "lazy" sub-sampling low pass filter that corresponds to efficient selective reading of the input image. Many interpolating subband transforms with increasing number of vanishing moments can be selected to suit this requirement. However, this choice should be avoided whenever possible, since it conflicts with the first and second considerations.

The decompositionType(j) parameters control the type of multi-resolution decomposition performed on each resolution j. These parameters together with the parameter named-jumpSize give us the opportunity to achieve quick response to the first view of the 3-D image. For example in medical applications the common first view is the group of several subsequent 2-D slices of the 3-D image volume at thumbnail resolution. For this case it is preferred to perform several XXH-Subbands type decomposition on the original image up to the thumbnail resolution, and then to perform decompositions of HHX-Subbands type as described herein above in reference to FIG. 4.

The parameter named jumpSize controls the tradeoff between fast response to the user's initial request for interaction with the image and response times to subsequent ROI requests. When jumpSize is large, the initial response is faster, but each computation of a region of interest with higher resolution than the jump might require processing of a large portion of the original image.

The threshold(j) parameters control the visual quality in the case of lossy compression. The smaller the thresholds, the higher the visual quality is. Naturally, the tradeoff is quality for bit-rate. A suitable choice for "visually lossless" quality in the case of a Grayscale image is threshold(j)=6 for j=numberOfResolutions, and threshold(j)=4 for j<numberOfResolutions. The choice is also derived from the mathematical properties of the pre-chosen subband transform(s). In the case of lossless compression these parameters are not used since in lossless mode there is no threshold operation performed.

By adding sufficient rows and columns to each resolution j (padding), one obtains an exact tiling of the multiresolution structure with $\{nTilesX(j), nTilesY(j), nTilesZ(j)\}$ tiles for each resolution j, each of size [tileLength, tileLength, tileHeight].

Figure 23:
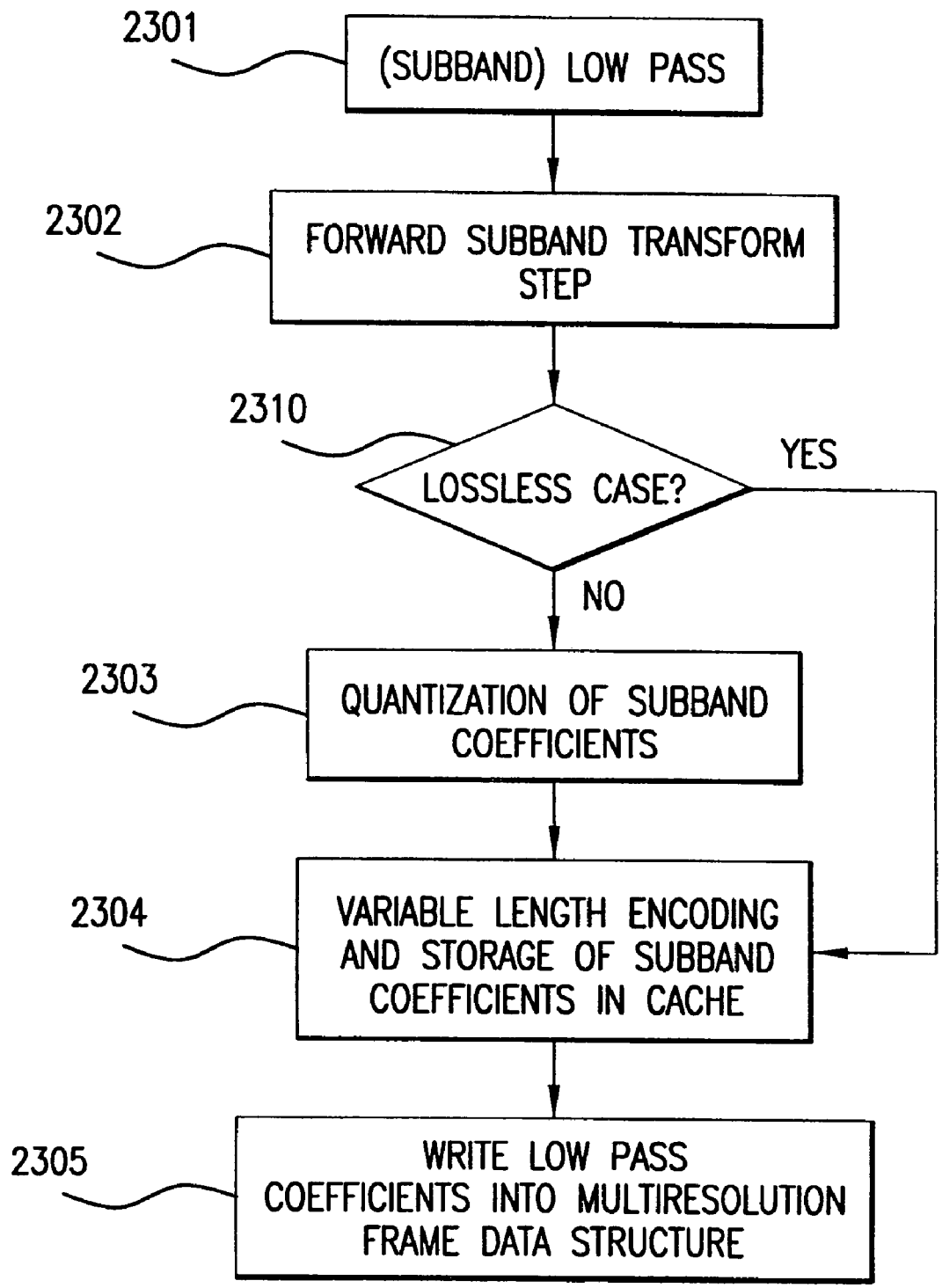
FIG. 23 is a flowchart illustrating a server preprocessing function of the present invention.

The following is a discussion of the memory requirements of a multi-resolution data structure, and of the allocation and initialization of this memory with reference to FIG. 23.

For efficient use of memory during the preprocessing stage, storage needs to be allocated for 2×tileHeight+maxfilterSizeZ frames at each resolution $1 \leq j \leq$ numberOfResolutions−jumpSize. Each such memory frame buffer stores the low-pass coefficients at various resolutions. Thus the memory complexity is limited by several single frames and is independent of the number of frames in the original sequence.

During the preprocessing, the resolutions are scanned simultaneously from start to end in the z direction. For each resolution the corresponding frame buffer stores low-pass coefficients or "pixels" at that resolution. The core of the preprocessing algorithm are steps 2302 to 2305 where tiles of pixels of size

[tileLength+2×maxFilterSizeXY,tileLength+2×maxFilterSizeXY,tileHeight+2×maxFilterSizeZ]

are read from the memory frame buffers and handled one at a time. In Step 2302 the tile is transformed into a tile of size [tilelength, tileLength, tileHeight] containing two types of coefficient data: subband coefficients and "pixels" at a lower resolution. The subband coefficients are processed in step 2303 and step 2304 and are stored in the cache. The lower resolution pixels are inserted in step 2305 into a lower resolution memory frame buffer. Whenever a new sub-tile of lower resolution "pixels" (step 2305) is inserted into a frame, a memory management module performs the following check. If a part of the sub-tile exceeds the current virtual boundaries of the memory frame buffer, the corresponding first frames of the memory frame buffer are then considered unnecessary. Their memory is (virtually) re-allocated for the purpose of storing new sub-tile data. The pseudo-code of the memory constraint scan algorithm is detailed in FIG. 24.

In Step 2301 the low pass filters of the transforms subbandTransformType(j), numberOfResolutions−jumpSize<j≦numberOfResolutions, are used to obtain a low resolution 3-D image at the resolution numberOfResolutions−jumpSize (as can be seen in FIG. 5). The low pass calculation is initiated by an input operation of tiles of pixels from the memory frame buffers performed in step 2302. Whenever there is an attempt to read missing low resolution tiles, they are computed by low-pass filtering the original image and inserted into the memory frame buffer. As explained herein above, the insertion over-writes frames which are no longer required, such that the algorithm is memory constraint. By metaphorically jumping up the multi-resolution ladder, the present invention avoids computation and storage of high resolution subband coefficients. For example, given a sequence of 2-D images of the size 512×512 pixels, and given thumbnails of size 64×64, by choosing jumpSize=3, the main preprocessing stages: subband transform, quantization and storing are done only for a low resolution 3-D image that is 64 times smaller than the original 3-D image. When the user requests to view a higher resolution ROI, for example a single slice of size 128×128, the server needs to read (again) the associated local area of the original image and perform (using step 2204) more computations.

In the lossy mode of operation, the low pass filtering can be implemented efficiently in integer numbers without much consideration of round-off errors. In lossless mode (when losslessMode=true ), care must be taken to ensure that the results of the low pass step, which are low resolution pixels, can be used in a lossless framework. Specifically, it must be ensured that in a scenario where a user views a low resolution ROI and then zooms into a high resolution ROI, the low resolution data already present at the client side can be used for the rendering such that only the difference between the low resolution and high resolution needs to be progressively transmitted until lossless quality is reached. Thus, the low pass filter is implemented using a special lossless "integer to integer" transform technique. Unfortunately, this means that this step is slower in lossless mode, due to this special implementation. Nevertheless, it is the embodiment as it provides fast response to the user's first request to view the image in a true lossless efficient imaging system.

In lossless mode the jumpSize parameter defines the number of lossless wavelet low pass steps that should be performed. A single low pass step is the same for Haar and CDF (1,3) and for the HHX-Subbands type of decomposition that is the only one used in the "jump". This step is defined by the following Eq. 12.

$$ll(m, n) = \left\lfloor \frac{x(2m+1, 2n+1) + x(2m, 2n+1)}{2} \right\rfloor + \left\lfloor \frac{x(2m+1, 2n) + x(2m, 2n)}{2} \right\rfloor \quad \text{(Eq. 12)}$$

The server performs these steps efficiently (almost like the lossy algorithm) by a single operation that simulates exactly jumpSize low pass steps defined by Eq. 12. The simplicity of the formula makes filters such as Haar and CDF (1,3) optimal in the sense of low pass efficiency.

Step 2302 is one step of an efficient local subband transform (FWT) performed on a tile of pixels at the resolution $1 \leq j \leq$ numberOfResolutions−jumpSize. As described herein above, the type of transform is determined by the parameters decompositionType(j) and subbandTransformType(j). The transform is performed on an extended tile of pixels of size

[tileLength+2×maxFilterSizeXY,tileLength+2×maxFilterSizeXY,tileHeight+2×maxFilterSizeZ]

(except at the boundaries) read directly from the memory frame buffers at the resolution j+1. The output of the step is a subband tile as defined by Eq. 2 of size [tileLength, tileLength,tileHeight] containing two types of coefficient data: subband/wavelet coefficients and low resolution coefficients/pixels. The transform step can be efficiently implemented in integer numbers. This saves converting the original pixels to floating-point representation and facilitates the next quantization step (used for lossy transform).

The subband transform of step 2302 outputs two types of coefficients: scaling function (low pass) and wavelet (high pass). For the lossless case their wavelet coefficients also include additional Half bit plane data. The wavelet coefficients are treated in step 2303 and step 2304 while the scaling function coefficients are treated in step 2305. Tiles of pixels which are located on the boundaries sometimes need to be padded by extra frames, rows and/or columns of pixels, such that they will formulate a complete tile of size [tileLength,tileLength,tileHeight].

In step 2303, unless losslessMode is true, the subband coefficients calculated in step 2302 are quantized. This procedure is performed at this time for the following reason. It is required that the coefficients computed in the previous step will be stored in the cache 121. To avoid writing huge amounts of data to the cache 121, some compression is required. Thus, the quantization step serves as a preparation step for the next variable length encoding step. It is important to point out that the quantization step has no effect on compression results. Namely, the quantization step is synchronized with the encoding algorithm ensuring that the results of the encoding algorithm of quantized and non-quantized coefficients are identical. A tile of an image at the resolution j is quantized using the given threshold, threshold (j): for each coefficients x, the quantized value is $\lfloor x/\text{threshold}(j) \rfloor$. It is advantageous to choose the parameters threshold(j) to be dyadic such that the quantization can be implemented using integer shifts. The quantization procedure performed on a subband tile is as follows:

First, initialize maxBitPlane(tile)=0.
Second, iterate over each group of four coefficients {coef(2i+x,2j+y,k),x∈[0,1],y∈[0,1]}.

For each such group initialize a variable length parameter length(i,j,k)=0 .

Third, quantize each coefficient in the group using the appropriate threshold.

Fourth, and for each coefficient, update length(i,j,k) by the bit plane b of the coefficient,where the bit plane is defined by

|coef(2i+x,2j+y,k)|∈[$2^b$threshold(j),$2^{b+1}$threshold(j))

Fifth, after processing the group of four coefficients, use the final value of length(i,j,k) to update maxBitPlane(tile) by maxBitPlane(tile)=max(maxBitPlane(tile), length(i,j,k))

Last, store the value maxBitPlane(tile) in the cache (121).

As for handling subband tiles located at the boundaries. A solution sets to zero subband coefficients that are not associated with the actual image, but only with a padded portion. To do this the amount of padding is taken into account together with the parameters maxFilterSizeXY and maxFilterSizeZ. The motivation for this procedure of the removal of these coefficients is coding efficiency.

In step 2304 the coefficients that were quantized in the previous step are variable length encoded and stored in the cache 121. If maxBitPlane(tile)=0 no data is written, else an iteration is performed over the coefficient groups {coef(2i+x,2j+y,k),x∈[0,1],y∈[0,1]}. For each such group the group's variable length length(i,j,k) is first written using $\log_2$(maxBitPlane(tile)) bits. Then for each coefficient in the group length(i,j,k)+1 bits are written representing the coefficient's value. The least significant bit represents the coefficient's sign. For example, if it is 1 then the variable length encoded coefficient is assumed to be negative. The HalfBit subband coefficients are written last using one bit per coefficient.

In step 2305 the low pass coefficients are inserted into the pyramidal frame buffer data structure at the appropriate location. If the size of the subband tile is [tileLength, tileLength,tileHeight], then the size of the low pass sub-tile is [tileLength/2,tileLength/2,tileHeight] for the HHX_Subbands type decomposition and [tileLength,tileLength,tileHeight/2] for XXH_Subbands type, as explained herein above in reference to FIG. 4. Denoting the size of the sub-tile by [sizeX,sizeY,sizeZ], if the coordinates of the tile are (t_x,t_y,t_z,t_resolution), then the coefficients are copied into the frame buffer t_resolution−1 at the virtual location described by the following Eq. 13.

$$\text{Location} = [\text{t\_x} \times tileSizeX, (\text{t\_x}+1) \times tileLength] \times \quad \text{(Eq. 13)}$$
$$[\text{t\_y} \times tileSizeY, (\text{t\_y}+1) \times tileLength] \times$$
$$[\text{t\_z} \times tileSizeZ, (\text{t\_z}+1) \times tileHeight]$$

As explained herein above, these coefficients will be merged into a bigger tile of low resolution pixels and processed later.

Step 2202 is the decoding of the request stream. This is the inverse step 1703. Once the request stream arrives at the server, it is decoded back to a data block request list. Each data structure defined by Eq. 11 and representing a group of requested data blocks is converted to the sub-list of these data blocks.

Figure 25:
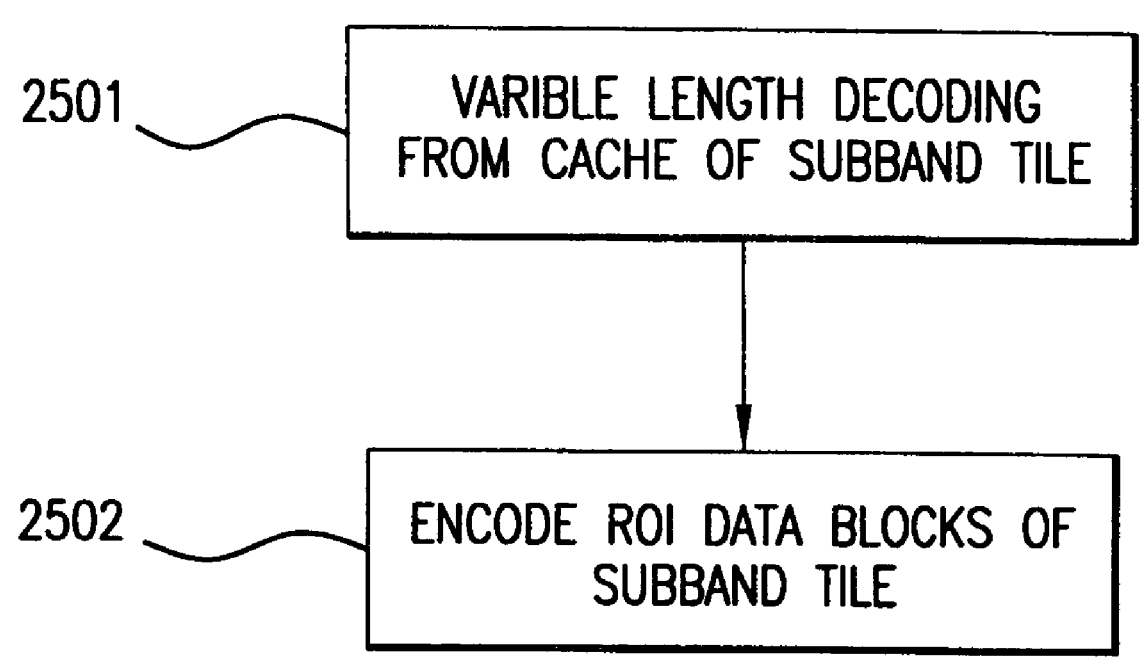
FIG. 25 is a flowchart illustrating the low resolution encoding function of the present invention.

Reference is now made to FIG. 25 describing step 2203 in detail. This step is only performed whenever the data blocks associated with low resolution subband tile are not available in the server cache 121.

Step 2501 is the inverse step of step 2304. In the preprocessing algorithm subband tiles of low resolution, that is resolutions lower than numberOfResolutions−jumpSize, were stored in the cache using a variable length type algorithm. For such a tile the variable length representation is first decoded, and then the algorithm uses the stored value maxBitPlane(tile).

If maxBitPlane(tile)=0, then all the coefficients are set to zero including the HalfBit subband for lossless case, else and in the lossy case following decoding algorithm if performed. For each group of four coefficients $\{coef(2\times i+x, 2\times j+y, k)\}_{x,y=0,1}$, $\log_2$(maxBitPlane(tile)) bits are read representing the variable length of the group.

Assuming the variable length is length(i,j,k), and for each of the four coefficients length(i,j,k)+1 bits are then read. The least significant bit represents the sign. The reconstructed coefficient takes the value defined by Eq. 14

$$\text{value} = \text{threshold} \times (\textit{readBits} \gg 1) \times \begin{cases} -1, \textit{readBits} \ \& \ 1 = 1 \\ 1, \textit{readBits} \ \& \ 1 = 0 \end{cases} \quad \text{(Eq. 14)}$$

In the lossless case threshold=1, and a special treatment should be made if maxBitPlane(tile)=1. In this case all the coefficients are set to zero, and the HalfBit subband coefficient are read bit by bit from cache. If maxBitPlane(tile)>1 then the HalfBit subband coefficient are read bit by bit from cache, and then the decoding algorithm is performed as in the lossy case.

In step 2502 the encoding algorithm described in reference to Table 1 encodes the requested data blocks associated with the extracted subband tile.

In case that a jumpSize greater than zero is used in step 2201 and the resolution of the ROI is greater than numberOfResolutions−jumpSize the following is the calculation. It is a variation on the preprocessing step described in reference to FIG. 23. Whenever the server receives a request list of data blocks its checks the following. If a data block has been previously computed (present in the cache 121), or if it is associated with a low resolution subband tile data block, then it is either read from the cache or handled in step 2203. Else, the coordinates of the data block are used in the same manner as in step 1704 described herein above to find the minimal portion of the ROI that needs to be processed. A local version of the preprocessing algorithm is then performed for this local portion. The difference between this variation and the description in reference to FIG. 23 is that the subband coefficients of ROI are directly encoded by arithmetic encoder described in reference to Table 1 and not by Variable Length encoder as in step 2304 and step 2305 of the preprocessing algorithm.

In the final step, the encoded data tiles are sent to the client, in the order they were requested. In many cases data blocks will be empty. For example, for a region of the original image with a constant pixel value all of the corresponding data blocks will be empty, except for the first one, which will contain only one byte with the value zero representing maxBitPlane(tile)=0. For a region of the image of low information content only the last data blocks representing higher accuracy will contain any data. Therefore, to avoid unnecessary communications, cubes of empty data blocks are collectively reported to the client using a structure of the type defined by Eq. 11 under the restriction that they are reported in the order in which they were requested. For blocks containing actual data we need only report the data block's size in bytes, since the client already knows which data blocks to expect and in which order.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for transmitting three dimensional (x, y, z axis) digital source images over a communication network, comprising:
   a storage device for storing three dimensional digital source images;
   a client computer coupled to the communication network, said client computer operative to generate and transmit to a server computer a request for interaction with the three dimensional source image stored on said image storage device, said request for interaction comprising an ordered request list specifying data blocks for progressive rendering of a given region of interest (ROI) within said three dimensional source image; and
   said server computer coupled to the communication network and said image storage device, the server computer comprising means for preprocessing said three dimensional source image through a three dimensional wavelet transform wherein resultant three dimensional subband coefficient data comprises interslice correlation information, receiving said ordered request list from the client computer and progressively transmitting to said client computer three dimensional subband coefficient data blocks corresponding to said given region of interest in accordance with said ordered request list.

2. The system according to claim 1, wherein:
   the request generated by the client computer specifies a resolution; and
   the server computer provides a number of three dimensional data blocks corresponding to said resolution.

3. The system according to claim 1, wherein said three dimensional wavelet transform comprises the steps of:
   performing two dimensional subband transform decompositions in x-axis and y-axis directions on said three dimensional image to yield a two-dimensionally transform-decomposed digital image; and
   performing a one dimensional subband decomposition in a z-axis direction on a portion of said two-dimensionally transform-decomposed three dimensional image.

4. The system according to claim 1, further comprising the step of transmitting to said client computer data representing thumbnail resolution images.

5. The system according to claim 1, wherein said ordered request list generated by said client computer specifies a quality threshold and said server computer comprises means for sending three dimensional subband coefficient data blocks corresponding to said quality threshold.

6. The system according to claim 1, wherein said client computer comprises means for requesting fewer quality layers if an image is mapped in accordance with a luminance mapping function to a viewing device having fewer bits per pixel than that of said image.

7. The system according to claim 1, wherein said three dimensional subband coefficient data block comprises x, y, z and quality layer information.

8. The system according to claim 1, wherein said three dimensional subband coefficient data block comprises x, y, z, resolution and quality layer information.

9. A method for transmitting a sequence of digital source images as a three dimensional image from a server computer to a client computer over a communication network, said method comprising the steps of:

storing a sequence of digital source images on a storage device;

a client computer coupled to said communication network generating and transmitting to a server computer a request for interaction with an image sequence stored on said storage device, said request for interaction comprising an ordered request list specifying data blocks for progressive rendering of a given region of interest (ROI) within said image sequence; and said server computer coupled to said communication network and said image storage device performing two dimensional subband transform decompositions in x-axis and y-axis directions on each image within said sequence to yield a two-dimensionally transform-decomposed digital image;

said server computer performing a one dimensional subband transform decomposition in a z-axis direction on a portion of said two-dimensionally transform-decomposed digital image to generate three dimensional subband coefficient data comprising inter-image correlation information; and said server computer progressively transmitting to said client computer three dimensional subband coefficient data blocks corresponding to said given region of interest in accordance with said ordered request list.

10. The method according to claim 9, further comprising the steps of:

including in the request generated by the client computer a specified resolution; and providing one or more three dimensional data blocks from the server computer that correspond to said resolution.

11. The method according to claim 9, further comprising the step of said server computer transmitting to said client computer data representing thumbnail resolution images.

12. The method according to claim 9, wherein said ordered request list generated by said client computer specifies a quality threshold and said server computer sends three dimensional subband coefficient data blocks corresponding to said quality threshold.

13. The method according to claim 9, wherein said server computer progressively transmits said three dimensional subband coefficient data blocks to said client computer using one of the three progressive modes: progressive by accuracy, progressive by resolution or progressive by spatial order.

14. The method according to claim 9, wherein said client computer requesting fewer quality layers if an image is mapped in accordance with a luminance mapping function to a viewing device having fewer bits per pixel than that of the image.

15. The method according to claim 9, wherein said three dimensional data block comprises x, y, z and quality layer information.

16. The method according to claim 9, wherein said three dimensional data block comprises x, y, z, resolution and quality layer information.

17. A server for progressive streaming of sequences of digital source images as a three dimensional image to a client over a communications network, comprising:

an image storage device for storing a sequence of digital source images;

a memory cache;

a processor in communication with said image storage device, said processor comprising means for:

preprocessing the image sequence through a three dimensional forward wavelet transform to yield three dimensional wavelet coefficient data comprising inter-image correlation information;

storing said three dimensional wavelet coefficient data in said memory cache;

receiving an ordered request list for one or more three dimensional data blocks from said client, each three dimensional data block corresponding to a given region of interest;

checking if a requested three dimensional data block is present in said memory cache, and if not, computing three dimensional subband coefficient data blocks corresponding to said data block and storing said coefficient data in said memory cache; and transmitting to said client three dimensional subband coefficient data blocks corresponding to said given region of interest.

18. The server according to claim 17, wherein said three dimensional wavelet transform comprises the steps of:

performing two dimensional subband transform decompositions in x-axis and y-axis directions on said image sequence to yield two-dimensionally transform-decomposed digital images; and performing a one dimensional subband decomposition in a z-axis direction on a portion of said two-dimensionally transform-decomposed image sequence.

19. The server according to claim 17, wherein said processor further comprises means for transmitting to said client computer data representing thumbnail resolution images.

20. The server according to claim 17, wherein said ordered request list received from the said client computer specifies a quality threshold and said processor comprises means for transmitting three dimensional subband coefficient data blocks corresponding to said quality threshold in response thereto.

21. The server according to claim 17, wherein said processor comprises means for progressively transmitting said three dimensional subband coefficient data blocks to said client computer using one of the following three progressive modes: progressive by accuracy, progressive by resolution or progressive by spatial order.

22. The server according to claim 17, wherein said processor comprises means for receiving from said client computer a request for fewer quality layers if an image is mapped in accordance with a luminance mapping function to a viewing device having fewer bits per pixel than that of the image.

23. The server according to claim 17, wherein said three dimensional data block comprises x, y, z and quality layer information.

24. The server according to claim 17, wherein said three dimensional data block comprises x, y, z, resolution and quality layer information.

25. A computer readable recording medium that stores a computer program for progressively streaming sequences of digital source images as a three dimensional image to a client over a communications network, said computer program including instructions, which when executed, cause a computer to execute:

preprocessing said source image sequence through a three dimensional forward wavelet transform to yield three dimensional subband coefficient data comprising inter-image correlation information;

storing said three dimensional subband coefficient data in a memory cache;

receiving an ordered request list for one or more three dimensional data blocks from said client, each data block corresponding to a given region of interest;

checking if a requested three dimensional data block is present in said memory cache, and if not, computing three dimensional subband coefficient data blocks corresponding to said data block and storing said coefficient data in said memory cache; and transmitting to the client three dimensional subband coefficient data blocks corresponding to said given region of interest.

26. The computer readable recording medium according to claim 25, further comprising transmitting to said client data representing thumbnail resolution images.

27. The computer readable recording medium according to claim 25, further comprising sending three dimensional subband coefficient data blocks corresponding to a quality threshold to said client in response to an ordered request list received therefrom.

28. The computer readable recording medium according to claim 25, wherein transmitting comprises progressively transmitting said three dimensional subband coefficient data blocks to said client using one of the following three progressive modes: progressive by accuracy, progressive by resolution or progressive by spatial order.

29. The computer readable recording medium according to claim 25, wherein said three dimensional data block comprises x, y, z and quality layer information.

30. The computer readable recording medium according to claim 25, wherein said three dimensional data block comprises x, y, z, resolution and quality layer information.

* * * * *